US008790621B2

(12) United States Patent
Zhao

(10) Patent No.: US 8,790,621 B2
(45) Date of Patent: Jul. 29, 2014

(54) NANOPARTICLES AND NANOPARTICLE COMPOSITIONS

(75) Inventor: Yan Zhao, Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 22 days.

(21) Appl. No.: 13/640,698

(22) PCT Filed: Apr. 8, 2011

(86) PCT No.: PCT/US2011/031736
§ 371 (c)(1),
(2), (4) Date: Dec. 18, 2012

(87) PCT Pub. No.: WO2011/130114
PCT Pub. Date: Oct. 20, 2011

(65) Prior Publication Data
US 2013/0101516 A1 Apr. 25, 2013

Related U.S. Application Data

(60) Provisional application No. 61/323,072, filed on Apr. 12, 2010.

(51) Int. Cl.
A61B 5/055 (2006.01)
A61K 9/14 (2006.01)
A61B 5/00 (2006.01)
A01N 25/00 (2006.01)
C07D 403/00 (2006.01)
C07C 319/00 (2006.01)

(52) U.S. Cl.
USPC ............. 424/9.3; 424/489; 424/9.6; 514/772; 548/255; 568/38

(58) Field of Classification Search
CPC .............. A61K 9/1075; A61K 9/1272; A61K 47/48815; C08L 2666/02
See application file for complete search history.

(56) References Cited

U.S. PATENT DOCUMENTS

| | | | |
|---|---|---|---|
| 3,201,467 A | 8/1965 | Oakes | |
| 3,242,094 A | 3/1966 | Oakes | |
| 3,358,011 A | 12/1967 | Elliott | |
| 3,748,343 A | 7/1973 | Yu et al. | |
| 3,819,357 A | 6/1974 | Yu et al. | |
| 4,948,782 A | 8/1990 | Omura et al. | |
| 5,008,249 A | 4/1991 | Omura et al. | |
| 5,175,150 A | 12/1992 | Omura et al. | |
| 5,459,127 A * | 10/1995 | Felgner et al. | 424/450 |
| 5,705,270 A * | 1/1998 | Soon-Shiong et al. | 428/402.2 |
| 2003/0153001 A1 * | 8/2003 | Soane et al. | 435/7.1 |
| 2003/0230818 A1 * | 12/2003 | Chopra et al. | 264/4 |
| 2006/0057423 A1 | 3/2006 | Steudel et al. | |
| 2008/0213377 A1 | 9/2008 | Bhatia et al. | |
| 2009/0011002 A1 | 1/2009 | Zabicky et al. | |
| 2009/0162424 A1 | 6/2009 | Cai et al. | |
| 2009/0202620 A1 | 8/2009 | Turnell et al. | |
| 2010/0036061 A1 | 2/2010 | Emrick et al. | |

FOREIGN PATENT DOCUMENTS

| | | |
|---|---|---|
| BE | 660565 | 9/1965 |
| FR | 1393451 | 3/1965 |
| JP | 2009-019176 A | 1/2009 |
| WO | WO-2008111239 A1 | 9/2008 |
| WO | WO-2009162424 A1 | 6/2009 |
| WO | WO-2011130114 A1 | 10/2011 |

OTHER PUBLICATIONS

"International Application Serial No. PCT/US2011/031736, International Preliminary Report on Patentability mailed Oct. 26, 2012", 12 pgs.
Gai, Yeong-Soon, "A highly conjugated polymer from tetrapropargylammonium bromide". *Journal of Macromolecular Science, Part A: Pure and Applied Chemistry*, vol. 32 (Suppl. 1&2), (1995), 55-63.
Khiat, A., et al., "Identification of the motilide pharmacophores using quantitative structure activity", *Journal of Peptide Research*, 52(4), (1998), 321-328.
"Chemical Substructures", American Chemical Society, (2009), 15 pgs.
"International Application Serial No. PCT/US2011/031736, International Search Report mailed Jun. 17, 2011", 2 pgs.
"International Application Serial No. PCT/US2011/031736, Written Opinion mailed Jun. 17, 2011", 13 pgs.
Cho, Hongkwan, et al., "Environmental Effects Dominate the Folding of Oligocholates in Solution, Surfactant Micelles, and Lipid Membranes", J. Am. Chem. Soc., vol. 132, No. 28, (2010), 9890-9899.
Cho, Hongkwan, et al., "Environmental Effects Dominate the Folding of Oligocholates in Solution, Surfactant Micelles, and Lipid Membranes", J. Am. Chem. Soc. vol. 132, No. 28, (2010), 9892-9899.
Cho, Hongkwan, et al., "Environmental Effects Dominate the Folding of Oligocholates in Solution, Surfactant Micelles, and Lipid Membranes", J. Am. Chem. Soc., (2010), A-J.
Gai, Y.-S., "A highly conjugated polymer from tetrapropargylammonium bromide", Macromolecular Reports, A32 (Suppl. 1&2), (1995), 55-63.
Jiang, X., et al., "Fabrication of Two Types of Shell-Cross-Linked Micelles with "Inverted" Structures in Aqueous Solution from Schizophrenic Water-Soluble ABC Triblock Copolymer via Click Chemistry", Langmuir, 25(4), (2009), 2046-2054.
Jiang, Xiaoze, et al., "Fabrication of Two Types of Shell-Cross-Linked Micelles with "Inverted" Structures in Aqueous Solution from Schizophrenic Water-Soluble ABC Triblock Copolymer via Click Chemistry", Langmuir, (2009), 2045-2054.

(Continued)

*Primary Examiner* — Michael G Hartley
*Assistant Examiner* — Sun Y Kim
(74) *Attorney, Agent, or Firm* — Schwegman Lundberg & Woessner, P.A.

(57) ABSTRACT

The invention provides multivalent surface-crosslinked micelle (SCM) particles, crosslinked reverse micelle (CRM) particles, and methods of making and using them. The SCM particles can be used, for example, to inhibit a virus or bacteria from binding to a host cell. The inhibition can be used in therapy for the flu, cancer, or AIDS. The CRM particles can be used, for example, to prepare metal nanoparticles or metal alloy nanoparticles, or they can be used in catalytic reactions.

12 Claims, 23 Drawing Sheets

(56) References Cited

OTHER PUBLICATIONS

Joralemon, M. J., et al., "Shell Click-Crosslinked (SCC) Nanoparticles. A New Methodology for Synthesis and Orthogonal Functionalization", J. Am. Chem. Soc., 127, (2005), 16892-16899.

Joralemon, Maisie J., et al., "Shell Click-Crosslinked (SCC) Nanoparticles. A New Methodology for Synthesis and Orthogonal Functionalization", J. Am. Chem. Soc., (2009), 16892-16899.

Peer, D., et al., "Nanocarriers as an emerging platform for cancer therapy", Nature Nanotechnology, 2, (Dec. 2007), 751-760.

Peer, Dan, et al., "Nanocarriers as an emrging platform for cancer therapy", Nature Nanotechnology, vol. 2, Dec. 2007, 751-760.

Zhang, Shiyong, et al., "Facile Preparation of Organic Nanoparticles by Interfacial Cross-Linking of Reverse Micelles and Template Synthesis of Subnanometer Au-Pt Nanoparticles", ACS Nano., (Mar. 2011), 10 pgs.

Zhang, Shiyong, et al., "Facile Preparation of Organic Nanoparticles by Interfacial Cross-Linking of Reverse Micelles and Template Synthesis of Subnanometer Au-Pt Nanoparticles", ACS Nano, vol. 5, No. 4, (2011), 2637-2646.

Zhang, Shiyong, et al., "Facile Synthesis of Multivalent Water-Soluble Organic Nanoparticles via "Surface Clicking" of Alynylated Surfactant Micelles", Macromolecules, (2010), 4020-4022.

Zhang, Shiyong, et al., "Rapid Release of Entrapped Contents from Multi-Functionalizable, Surface Cross-Linked Micelles upon Different Stimulation", J. Am. Chem. Soc. vol. 132, No. 31, (2010), 10642-10644.

Zhang, Shiyong, et al., "Rapid Release of Entrapped Contents from Multi-Functionizable, Surface Cross-Linked Micelles upon Different Stimulation", J. Am Chem. Soc., vol. 132, No. 31, (2010), 10642-10644.

Zhao, Yan, "Water-Soluble Nanoparticles for Green Catalysis in Water", White Paper submitted to DOE_BES, (2010), 1-4.

\* cited by examiner

NANOPARTICLES AND NANOPARTICLE COMPOSITIONS

CLAIM OF PRIORITY

This application is a nationalization under 35 U.S.C. 371 of PCT/US2011/031736, filed 8 Apr. 2011 and published as WO 2011/130114 A1 on 20 Oct. 2011, which claims the benefit of U.S. Provisional Application Ser. No. 61/323,072, filed 12 Apr. 2010, entitled "Nanoparticles and Nanoparticle Compositions " which application is incorporated herein by reference in its entirety.

GOVERNMENT FUNDING

This invention was made with Government support under CHE0748616 awarded by The National Science Foundation. The Government has certain rights in the invention.

FIELD OF THE INVENTION

This invention relates stable nanoparticles and nanoparticle compositions. The nanoparticles and nanoparticle compositions are prepared using surface crosslinked micelles (SCM) and are capable of incorporating materials such as pharmaceuticals and metal atoms.

BACKGROUND

With more than 12 million new cases of cancer each year, development of new and more effective anticancer therapies is a major priority of pharmaceutical researchers. Targeted delivery of therapeutic agents is particularly important in chemotherapy because anticancer drugs tend to have severe side effects, and anticancer drugs often kill healthy cells.

Both passive and active targeting have been employed in the delivery of anticancer drugs. Passive targeting relies on the enhanced permeability and retention (EPR) effect of cancerous tissues, a result of leaky blood vessels and poor lymphatic drainage. Active targeting depends on functionalizing the surface of the drug carrier with molecules that bind to overexpressed receptors on cancerous cells. Despite the benefits of active and passive targeting, compositions and methods with increased effectiveness are needed to further improve current cancer therapy.

Multivalent interactions frequently occur between biological entities. When strong binding is not possible with a single receptor-ligand pair, multivalency, or simultaneous binding between multiple receptors and ligands, can be an effective strategy to enhance the binding. Multivalent interactions are involved in many diseases, such as the common flu, cancer, and AIDS. Researchers have sought to develop multivalent ligands that can inhibit the binding of host cells by viruses and bacteria. Two of the most widely used scaffolds in multivalency are dendrimers and gold nanoparticles protected with multiple functionalized thiols. However, few clinical applications have been developed from these approaches.

Accordingly, there is a need for improved therapies for conditions that involve multivalent interactions. Multivalent ligands that can inhibit the binding of host cells by viruses, bacteria, and the like, are needed for such therapy. There is also a need for improved methods to prepare multivalent ligands, such as multivalent ligands in the form of nanoparticles.

SUMMARY

The invention provides stable nanoparticles and methods for the facile preparation of such nanoparticles. New methods to crosslink surfactants to afford multivalent organic nanoparticles are described herein. Micelles and reversed micelles can be prepared from various surfactants, and the micelles can be surface functionalized. The micelle nanoparticles can be either water soluble, or organic-soluble, and they can encapsulate "cargo" molecules that can be released upon exposure to specific stimuli. The nanoparticles can be used for a variety of purposes, including biomedical and chemical applications. The nanoparticles can be used as drug delivery vehicles, for example, by encapsulating suitable drugs. The drugs can be released at, for example, the site of an inflammation or a tumor.

The invention also provides new scaffolds for multivalent ligands. Water-soluble organic nanoparticles were prepared by crosslinking alkyne-containing surfactant micelles using highly efficient "click" reactions. Tens of ligands were attached to surface-crosslinked micelles (SCMs). Hydrophobic guests can be encapsulated inside the SCMs. When reversible crosslinkers are used, the hydrophobic guest molecules can be released upon cleavage of the crosslinkers, making the SCMs suitable for use as drug-delivery systems. The micelles can be prepared from surfactants that can be synthesized in a few simple steps from readily available and inexpensive starting materials. The self-assembling approach, crosslinking strategy, and post-modification employed in preparing the SCMs can also be used to prepare organic-soluble crosslinked reversed micelles (CRMs).

Accordingly, the invention provides an organic particle comprising surface crosslinked non-polymeric organic amphiphiles, wherein polar head groups of the amphiphiles are covalently crosslinked to each other at the surface of the particle through triazole groups or thioethers groups, and tail groups of the amphiphiles are arranged toward the interior of the particle; and the particle is water-soluble. The particle can include one or more cargo molecules, such as drug molecules, within the particle or at the surface of the particle. The invention also provides a delivery system comprising a plurality of particles described herein, and a pharmaceutically acceptable diluent or carrier.

The invention further provides an organic particle comprising non-polymeric crosslinked amphiphiles; where the amphiphiles comprise one or more nonpolar alkyl or fluoroalkyl chains and one or more polar head groups; the nonpolar chains are located on the exterior of the particle and the polar head groups are oriented toward the interior of the particle; and the amphiphiles are covalently crosslinked to each other near the head groups through triazole groups or thioether groups. These particles can be crosslinked reverse micelle (CRM) particles, and the particles can include one or more metal salts or metal particles in the core of the particle.

The invention also provides methods for preparing a surface-crosslinked organic particle. The method can include (a) combining a plurality of non-polymeric amphiphiles and water to form a noncovalently associated self-assembled micellar structure; where the non-polymeric amphiphiles have polar head groups and non-polar tail groups, and the polar head groups comprise two or more alkynyl groups or azido groups; (b) combining the self-assembled structure with a plurality of crosslinking agents, wherein the crosslinking agents comprise two or more azido groups or two or more alkynyl groups; and (c) inducing cycloaddition between the alkynes and azides, thermally or with a suitable catalyst, to covalently crosslink the amphiphiles to each other near the head groups through formation of triazole groups.

In preparing the micelles, the amphiphiles can self-assemble through hydrophobic interactions among the hydrophobic groups. The particles can be formed in the presence of cargo molecules so that the amphiphiles encapsulate the cargo molecules. The cargo can be, for example, one or more drugs, organic nanoparticles, inorganic nanoparticles, fluorophores, diagnostic agents, catalysts, or a combination thereof. The surface of the crosslinked particles can readily be functionalized using click chemistry reactions. For example, the surface-crosslinked particle can be contacted with one or more azido-containing or alkynyl-containing compounds such as water-soluble polymers, fluorophores, biological ligands, nucleic acids or analogues thereof, or a combination thereof; followed by inducing cycloaddition between alkynes or azides on the surface of the particle with the azido-containing or alkynyl-containing compounds, where the cycloaddition is induced thermally or with a suitable catalyst; to provide a water soluble multivalent particle that has a plurality of water-soluble polymers, fluorophores, biological ligands, nucleic acids or analogues thereof, or a combination thereof, linked to the surface of the particle through triazole groups.

The invention additionally provides a method for preparing a surface-crosslinked particle that includes (a) combining a plurality of non-polymeric amphiphiles and water to form a noncovalently associated self-assembled structure; where the non-polymeric amphiphiles have polar head groups and nonpolar tail groups, and the polar head groups comprise two or more alkenyl groups; (b) combining the self-assembled structure with a plurality of crosslinking agents, wherein the crosslinking agents comprise two or more thiol groups; and (c) inducing thiol-ene addition between the alkenes of the amphiphiles and the thiol groups of the crosslinkers photochemically to covalently crosslink the amphiphiles to each other near the head groups through the formation of thioether groups.

The invention further provides a method for preparing an organic particle that includes (a) combining a plurality of non-polymeric amphiphiles, water, and one or more nonpolar organic solvents, where the amphiphiles comprise one or more alkyl or fluoroalkyl chains and one or more polar head groups, to provide a noncovalently associated self-assembled structure; where the amphiphiles comprise two or more alkenyl groups near the head group of the amphiphile, the alkyl or fluoroalkyl chains of the amphiphiles are oriented on the exterior of the self-assembled structure, and the polar head groups are oriented toward the interior of the self-assembled structure; and (b) irradiating the self-assembled structures, in the presence of a plurality of crosslinking agents comprising two or more thiol groups, and a photoinitiator, to induce crosslinking at the interior of the structure; to provide an organic particle comprising amphiphilic moieties crosslinked by thioether groups.

The invention also provides a method of forming a metal nanoparticle comprising (a) contacting a metal salt and a plurality of particles described herein, for example, those that have nonpolar chains located on the exterior of the particle and polar head groups oriented toward the interior of the particle, in an aqueous/organic solvent mixture, thereby extracting metal ions of the metal salt into the organic solvent, wherein the metal ions migrate to the interior of the particle, to provide a crosslinked organic particle encapsulating metal ions; and (b) contacting the crosslinked organic particle encapsulating metal ions with a reducing agent, thereby reducing the metal ions in the interior of the crosslinked organic particle, to provide the metal nanoparticle.

The invention yet further provides a therapeutic method comprising administering to a patient in need of therapy an effective amount of the delivery system described herein, where the surface crosslinking of the particles encapsulate one or more drugs, the surface crosslinking of the particles is cleaved in vivo, and the drug of the particles is released into the body of the patient, thereby providing the drug to the patient.

The invention thus provides for the use of the compositions described herein for medical therapy. The medical therapy can be, for example, treating inflammation, treating a viral infection, treating a bacterial infection, or treating cancer, such as breast cancer, lung cancer, pancreatic cancer, or colon cancer. The invention also provided for the use of a composition described herein for the manufacture of a medicament to treat such conditions. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

Disclosed herein is a simple method to capture the micelles of alkynylated surfactants such as amphiphile 1 by covalent crosslinking. Crosslinking is readily achieved by the highly efficient alkyne-azide click reaction in the presence of 1 equiv 2 and a catalytic amount of Cu(I). The alkyne-azide click reaction was well described by Rostovtsev, Green, Fokin, and Sharpless (*Angew. Chem. Int. Ed.* 2002, 41, 2596), as well as Tornoe, Christensen, and Meldal (*J. Org. Chem.* 2002, 67, 3057). Sodium ascorbate (25 mol %) and $CuCl_2$ (5 mol %) and were found to work well in the reaction mixture to facilitate the crosslinking. After covalently crosslinking amphiphile 1, the resulting surface-crosslinked micelles (SCMs), typically 8-10 nm in diameter, have numerous residual alkynes on the surface. Multivalent post-modification can be readily accomplished by the same click reaction by adding desired azide-functionalized polymers or ligands after the crosslinking.

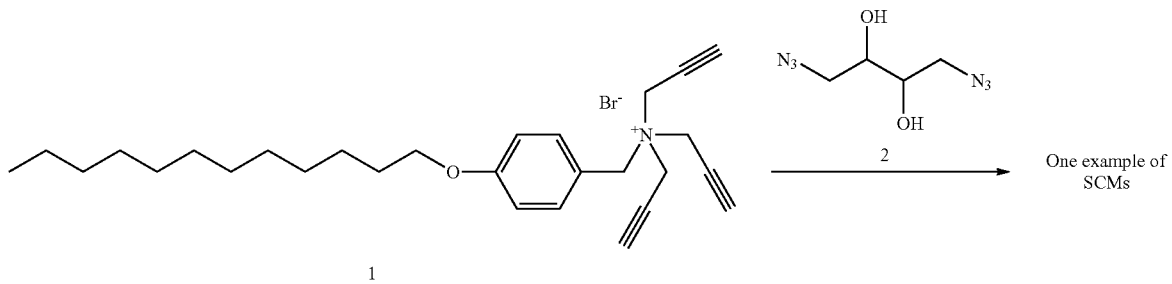 [SMILES: C#CC[N+](CC#C)(CC#C)Cc1ccc(OCCCCCCCCCCCC)cc1 ; [Br-] ; [N-]=[N+]=NCC(O)C(O)CN=[N+]=[N-]]

Figure 21:
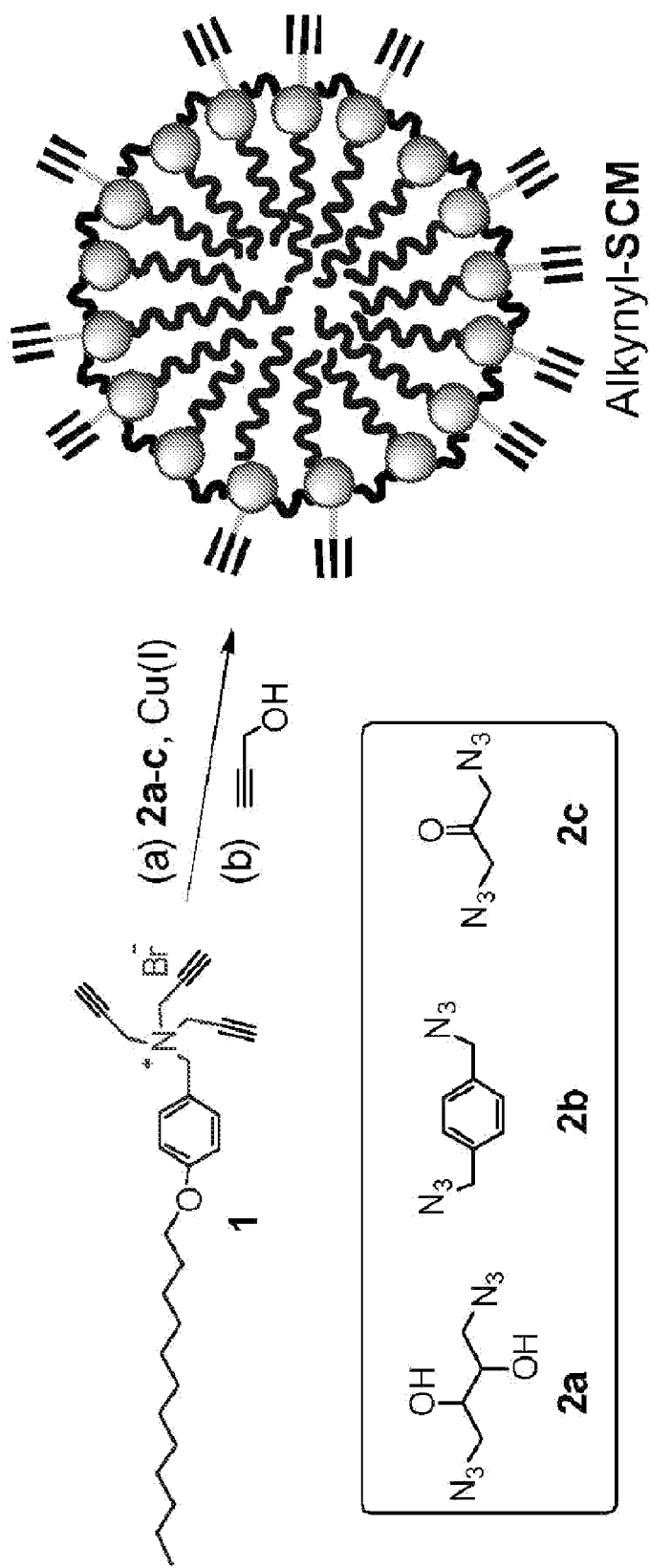

FIG. 21 illustrates the preparation of alkynyl-SCM.

Figure 22:
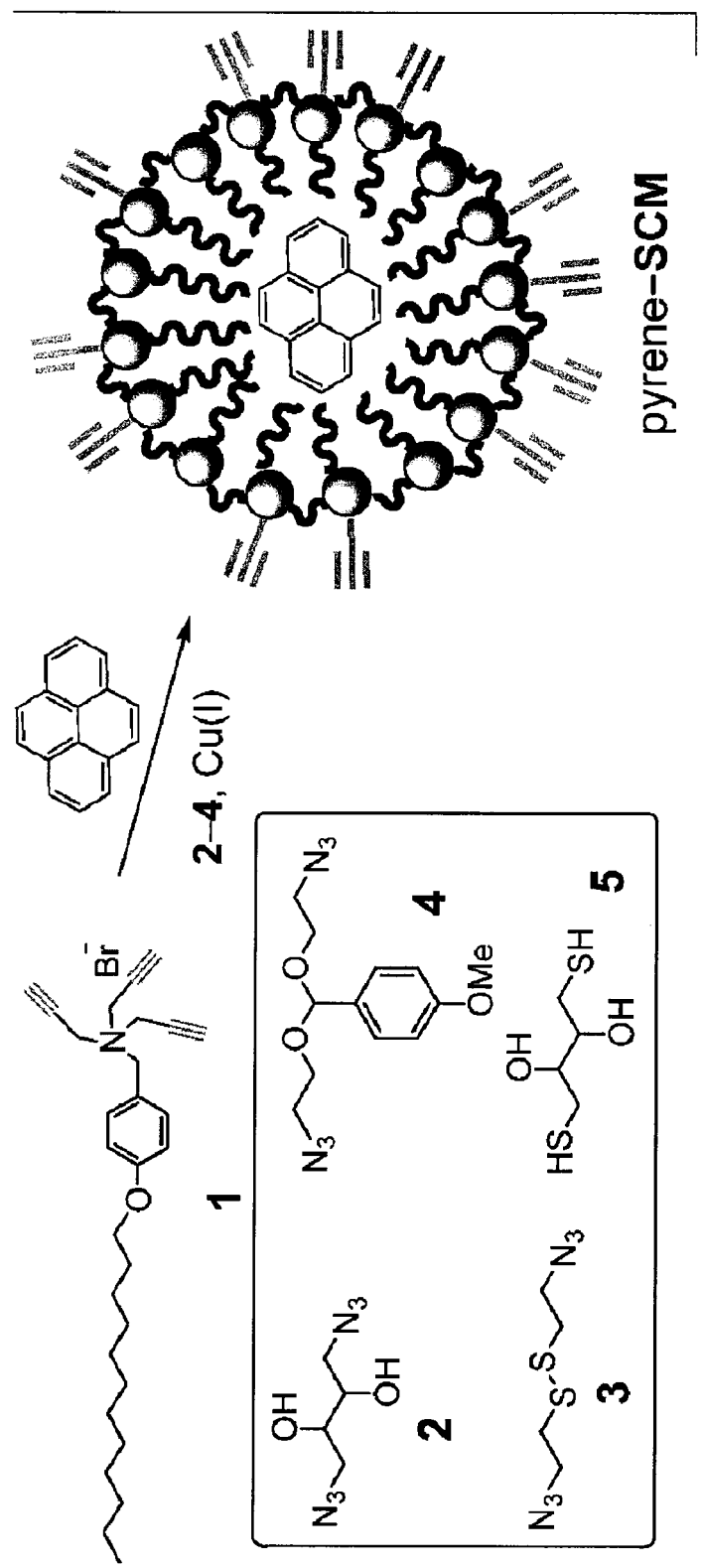

FIG. 22 illustrates the preparation of the pyrene-containing SCM

Figure 23:
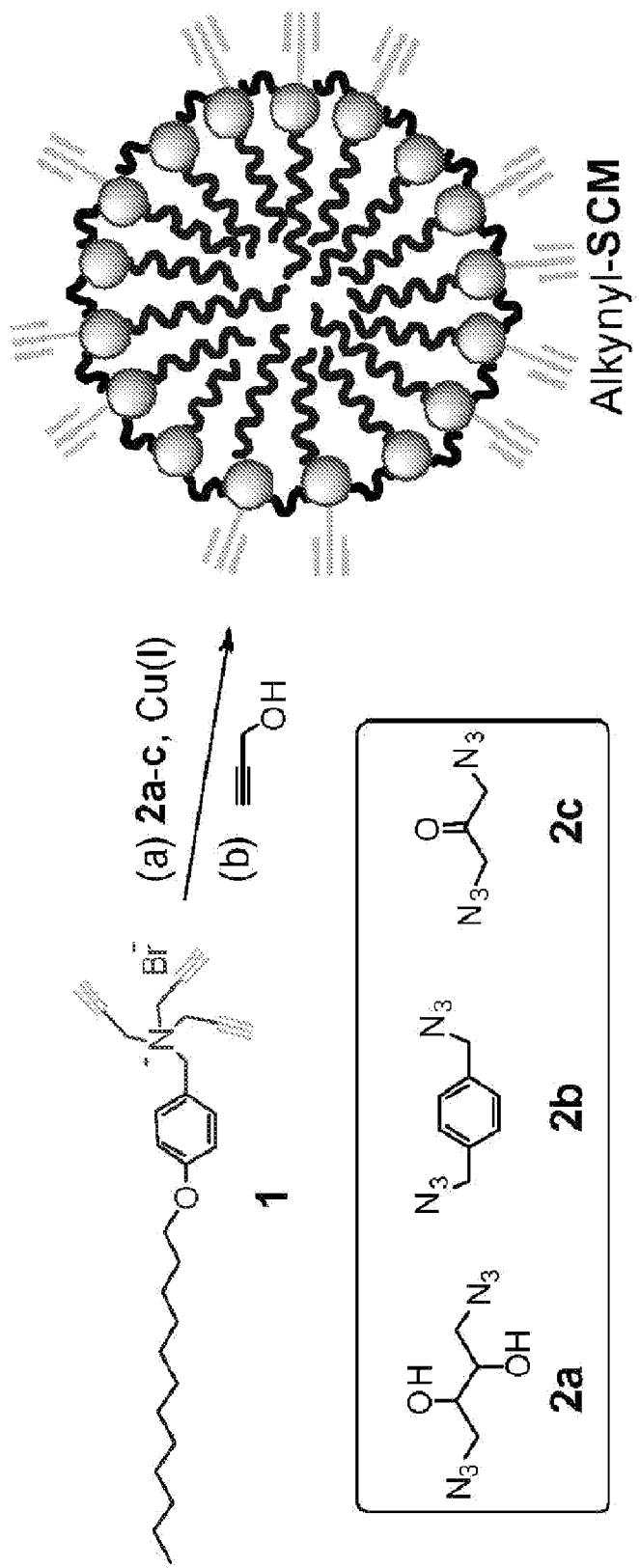

FIG. 23 illustrates the preparation of the alkynyl-SCMs

DETAILED DESCRIPTION

About half of potential drug candidates identified in high throughput screening have poor water solubility. These potential drug candidates are often denied further chance of development because of such solubility problems. Although surfactant micelles can solubilize hydrophobic agents in water, their use is drug delivery is often hampered by high critical micelle concentration (CMC), low thermodynamic stability, and the exceedingly dynamic nature of the assembly.

Polymeric micelles represent significant improvements over surfactant micelles because macromolecular amphiphiles tend to aggregate at concentrations orders of magnitude lower than their small molecule counterparts and they produce micelles with greater thermodynamic stability. A hydrophobic drug may be physically trapped inside the hydrophobic core of a polymeric micelle or covalently attached to the macromolecular amphiphile. The latter Accordingly, the invention provides multivalent surface-crosslinked micelle (SCM) particles, as well as crosslinked reverse micelle (CRM) particle, and methods of making and using them. The SCMs can be used to, for example, inhibit a virus or bacteria from binding to a host cell, such as in therapy used to treat the flu, cancer, or AIDS. The CRMs can be used, for example, to prepare metal nanoparticles or metal alloy nanoparticles.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a micelle composition described herein, or an amount of a combination of micelles described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "multivalent" refers to the capacity of a ligand, e.g., a micelle, to simultaneous bind multiple receptors.

The term "drug" refers to a therapeutic organic compound that can treat a disease or condition. Examples of drugs suitable for encapsulation in the micelles or liposomes described herein include doxorubicin, daunorubicin, vincristine, paclitaxel, neocarzinostatin, calicheamicin, cisplatin, carboplatin, oxaliplatin, satraplatin, picoplatin, lurtotecan, annamycin, docetaxel, tamoxifen, epirubicin, methotrexate, vinblastin, vincristin, topotecan, and nucleic acids such as DNA, RNA, small interfering RNA (siRNA), or their analogues. An example of a water-insoluble drug is camptothecin. An example of a water-soluble drug is doxorubicin. The classification of drugs as hydrophobic or water soluble is well known to those of skill in the art.

The term "diagnostic agent" refers to a compound that can be used to aid the presence, location, or severity of a condition in a cell, tissue, or patient. Examples of diagnostic agents suitable for encapsulation in the micelles, vesicles or liposomes described herein include quantum dots, gadolinium-(III) complexes for magnetic resonance imaging (MRI), magnetic nanoparticles, gold or silver nanoclusters, and organic fluorophores.

As used herein, term "crosslinked amphiphile" refers to an amphiphile that has an alkyne or alkene group, or alternatively, an azido or thio group, that has undergone a click reaction with a corresponding an azido, thio, alkyne, or alkene group. Non-limiting examples of amphiphiles suitable for crosslinking are illustrated in Schemes 5, 7-10, and 12-14.

As used herein, the term "crosslinking moiety" refers to a di-functionalized group that can, by use of a click reaction, covalently bond to an appropriately functionalized amphiphile. Non-limiting examples of crosslinking agents, or "crosslinkers", suitable for crosslinking with amphiphiles are illustrated in Schemes 6 and 11.

The term "non-polar hydrocarbon or fluorocarbon tail group" refers to a straight or branched alkyl chain that is attached to a head group of an amphiphile. The hydrocarbon or fluorocarbon tail can include about 6 to about 50 carbon atoms, or the tail can have a carbon atoms total of any integer between about 6 and about 20. Other chain lengths can be used, as described below. The non-polar hydrocarbon or fluorocarbon tail group can be any length of carbons that allows for the amphiphile to self assemble to form micelles.

The term "non-polymeric organic amphiphiles" refers to any amphiphile that does not include repeating monomer units, such as in polypeptides, to form the amphiphile. The term also excludes amphiphilic block copolymers.

The term "metal salt" refers to a compound that includes a metal cation and one or more anions. Examples of metal salts include, for example, $HAuCl_4$, $NaAuCl_4$, $Pd(NO_3)_2$, $PdSO_4$, $AgNO_3$, $H_2PtCl_6$, or $PdX_2$ wherein X is Cl, Br, or I, and the like.

Figure 1:
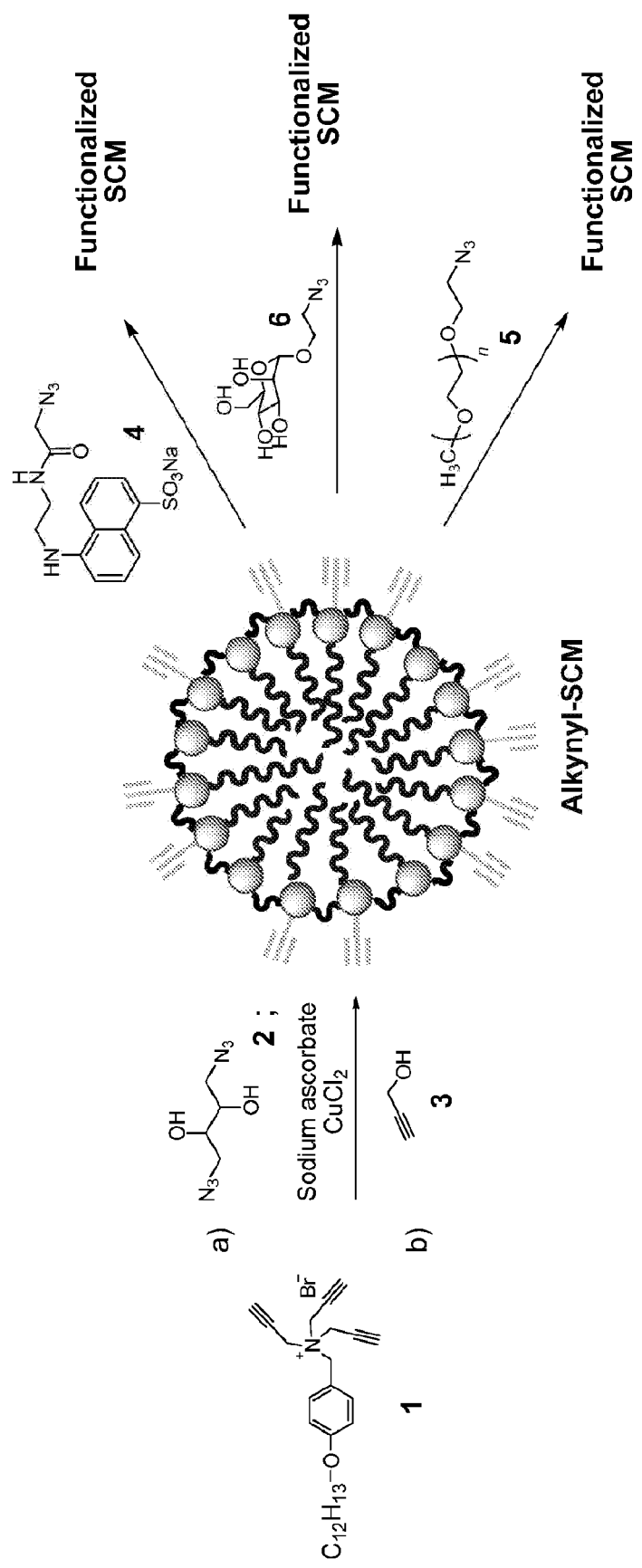
FIG. 1 illustrates the preparation of Surface Crosslinked Micelles (SCMs) and post-functionalization by click chemistry, according to an embodiment.

As used herein, in connection with the surface of a micelle particle, the term "functional group" refers to the portion of a compound that can be covalently bonded to the exterior of a micelle particle. Examples of functional groups include cell targeting agents, water soluble polymers, such as PEG and its derivatives (e.g., as illustrated in FIG. 1, wherein n is about 10 to about 500), sugars, including modified sugars and saccharides, fluorophores, and cell ligands such as biotin, folate, and the like. The functional groups can be linked to the micelle particles using click chemistry, for example, by modifying the compound to include a —$CH_2CH_2$—$N_3$ group or —$CH_2CH_2$—SH group, at any suitable location.

The click reaction between alkynes and azides can be catalyzed by, for example, various copper(I) catalysts. The copper (I) catalysts often are prepared from a copper(II) salt such as $CuSO_4$, $CuCl_2$, $CuBr_2$, or $Cu(OAc)_2$ and a suitable reducing agent such as sodium ascorbate, copper metal, or hydrazine. Alternatively, copper(I) salts such as CuI, CuCl, or CuBr may be used directly, in the presence or absence of another reducing agent.

Suitable photoinitiators for thiol-ene reactions include photoinitiators well known to those of skill in the art for thiol-ene reactions, such as 2,2'-dimethoxy-2-phenylacetophenone, 1-hydroxy-cyclohexylphenylketone, benzophenone, 2-hydroxy-2-methyl-1-phenyl-1-propanone, and 2-benzyl-2-(dimethylamino)-1-[4-(4-morpholinyl)phenyl]-1-butanone.

Development of Micelles and Formulations

Two widely used scaffolds in multivalency are dendrimers and gold nanoparticles protected with functionalized thiols. The methods of producing multivalent nanoparticles described herein are significantly less expensive than the procedures for preparing dendrimers and gold particles. The preparative methods described herein do not require iterative synthesis (required for dendrimer preparation) and they do not require rare metals, such as gold. Additionally, surface-functionalization of the nanoparticles described herein can be carried out in "one-pot" after crosslinking, and stimuli-triggered release mechanisms can be engineered into the nanoparticle system. The methods are applicable to, for example, the preparation of micelles, organic or inorganic nanoparticles, liposomes, and/or globular or rod-like reversed micelles.

An ideal carrier system for anticancer drugs should have several of the following features: (a) encapsulation of either water-soluble or water-insoluble drugs, (b) suitable nanodimension (50-200 nm) for maximal exploitation of the EPR effect (for passive targeting), (c) a surface architecture that allows for facile multivalent surface functionalization (e.g., with ligands or antibodies for active targeting), (d) high encapsulating capacity, (e) good stability prior to release, (f) fast release of encapsulated contents under appropriate stimulation (e.g., pH change), (g) simple preparation from readily available starting materials, and (h) good biocompatibility and low toxicity. These stringent requirements make it extremely challenging to develop effective delivery systems for anticancer drugs. The compositions and methods described can fulfill most, if not all, of these criteria, to create efficient drug delivery vehicles for both water-insoluble and water-soluble drugs, for example, anticancer drugs.

Micelles and Preparative Techniques

Radical polymerization of polymerizable surfactants (sufmers) is a common method to prepare organic nanoparticles from micelles. Previous procedures typically employ free radical polymerization of surfactant with polymerizable groups in the head or tail. However, the resulting nanoparticles are exclusively linked by carbon-carbon bonds. Therefore, these nanoparticles lack many of the features, such as encapsulation, reversibility, controlled release, and surface functionalization, needed for a suitable drug delivery system. Condensation polymerization may be used to crosslink a micelle, but this technique has significant drawbacks. For example, it is difficult to obtain high yields in amide or ester condensation reactions at room temperature in water. Further surface functionalization is also difficult.

The methods described herein solve these problems by using specially designed "clickable" surfactants taking advantage of highly efficient and water-compatible thiol-ene "click reaction". They differ from the conventional crosslinking methods described above in several important ways, to provide novel crosslinked micelles.

The invention therefore provides delivery vehicles for either water-soluble or water-insoluble drugs, controlled release devices, protective coatings for organic or inorganic nanoparticles, "nanoreactors" for templated synthesis of nanoparticles or nanowires, and/or a "housing" for catalytic metal nanoparticles.

The compositions and methods described herein also allow for targeted drug delivery and controlled release of hydrophobic or hydrophilic cargo molecules, such as anticancer drugs. The size, surface-functionality, and release-mechanism of this new class of materials can be controlled by varying the methods, as described below.

The invention provides novel approach to crosslink surfactant micelles by a "covalent-capture" strategy. Surfactants, such as compound 1, can be prepared in a few steps from simple, inexpensive starting materials (Scheme 1). The hydrophobic tail and the ammonium headgroup of compound 1 allow its formation into micelles spontaneously in water above its critical micelle concentration of $1.4 \times 10^{-4}$ M. The three alkynyl groups on the ammonium allow the surface of the micelle to be readily crosslinked with azido-containing crosslinkers (e.g., 2) by highly efficient click reactions (FIG. 1).

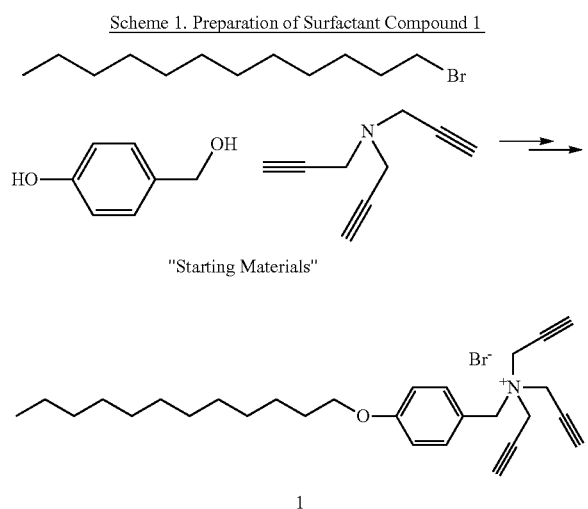

Scheme 1. Preparation of Surfactant Compound 1

Click chemistry (e.g., the 1,3-dipolar cycloaddition of an alkyne and an azide) is characterized by mild reaction conditions, nearly quantitative conversion, and tolerance of a variety of functional groups (Scheme 2).

Scheme 2. An example of a Click Reaction, according to an embodiment is

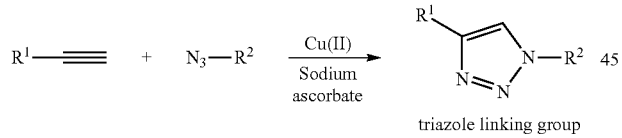

wherein $R^1$ is a portion of an amphiphilic surfactant and $R^2$ is a portion of a crosslinker or surface modifying functional group, or vice versa, or various groups as described herein.

Crosslinking of micelles is known, but previous procedures typically employ free radical polymerization of surfactant with polymerizable groups in the head or tail. The methods described herein differ from this conventional crosslinking in several important ways, to provide novel crosslinked micelles.

We found several advantages in using the thiol-ene click reaction in preparing RMs.

The reaction is extremely efficient, even in highly demanding situations such as the synthesis of dendrimers and selective functionalization of proteins.

Figure 2:
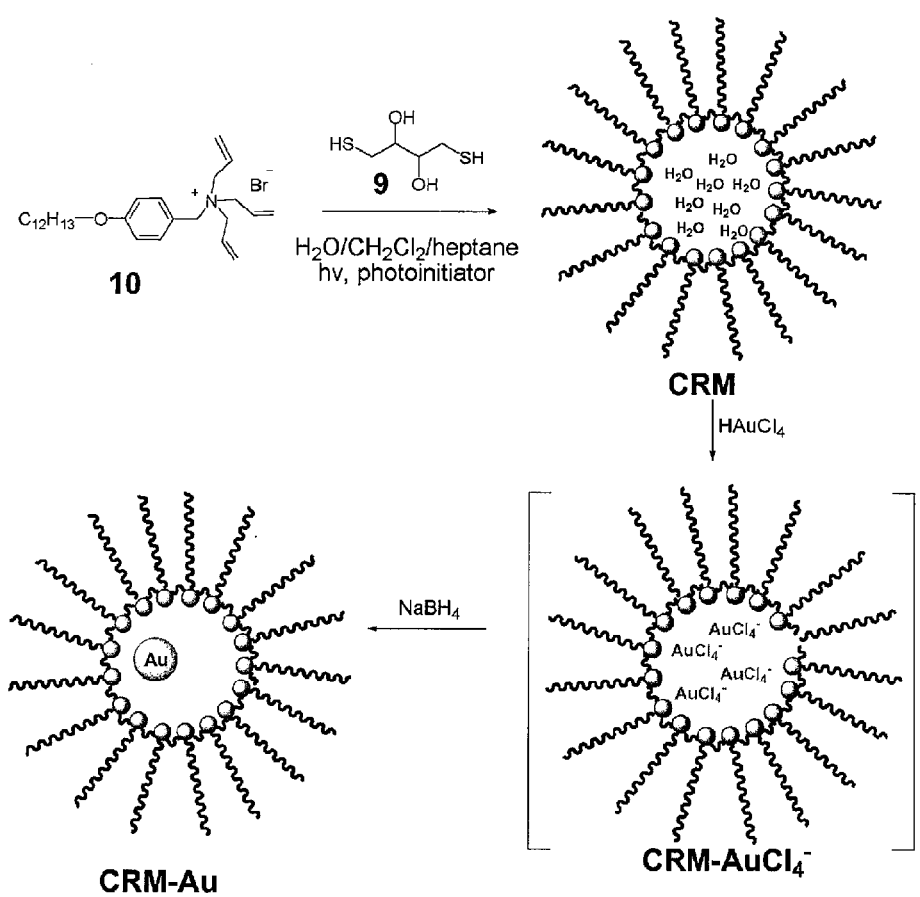
FIG. 2 illustrates the preparation of Crosslinked Reversed Micelles (CRMs) and templated synthesis of gold nanoparticles, according to an embodiment.

Incorporation of vinyl (i.e., ene) groups is extremely simple in a surfactant. Cationic surfactant 10 (FIG. 2), for example, contains three vinyl groups in the headgroup and can be prepared easily from commercially available materials. Having three cross-linkable groups in a concentrated fashion enhances the cross-linking density at the core and is advantageous to the stability of the cross-linked micelle.

There is great flexibility in the structure of thiol cross-linkers. In particular, if the distance between the thiol groups matches reasonably well with the average distance between the surfactant headgroups in the RM, cross-linking should cause minimal disturbance to the packing of the surfactants. Free radical polymerization of vinyl monomers, on the other hand, tends to make the structure more compact.

The reaction has excellent tolerance for functional groups. A wide range of commercially available thiol cross-linkers may be used, and introduction of additional functional groups to the RM is straightforward.

The crosslinker may be tuned in length. The loss of order that often occurs in radical polymerization can thus be avoided. After crosslinking and termination (of any unreacted azide groups, e.g., by propargyl alcohol 3, step (b) of FIG. 1), the Alkynyl-SCM obtained is about 8-10 nm in diameter, as determined by dynamic light scattering. A variety of other crosslinkers are illustrated in Schemes 6 and 11. The crosslinkers of Scheme 11 can be used, for example, when crosslinkable amphiphiles such as the POPC mimic or the Lyso-PC mimic are used (Schemes 7-11).

Because a 1:1 stoichiometry can be used for 1 and 2 in the crosslinking step, the Alkynyl-SCM on average can contain approximately one unreacted alkynyl group per surfactant molecule after crosslinking. For a typical micelle that contains 50-100 surfactant molecules, the Alkynyl-SCM has tens of alkynyl groups for post-functionalization through further click chemistry. For example, fluorophore 4, sugar 5, and water-soluble polymers 6 have been attached to the water-soluble organic nanoparticles (FIG. 1) to provide various surface-functionalized SCMs. Because click chemistry was used in both crosslinking and post-functionalization, the procedures can be carried out in "one-pot" at room temperature (~23° C.). Although multifunctionalization is also possible with dendrimers and gold nanoparticles, the methods described herein are advantageous for a number of reasons, including the spontaneous formation of surfactant micelles. The spontaneous micelle formation obviates the need for stepwise synthesis, such as in dendrimer preparation. A further advantage is the avoidance of expensive metals, such as rare metal catalysts and gold nanoparticles, which translates to lower overall costs for particle preparation, particularly on a large scale.

Reversible crosslinkers (e.g., 7 or 8, below) can be employed so that the SCMs can be destroyed after cleaving the disulfide or ketal bonds. For example, pyrene, a model hydrophobic guest, has been successfully trapped inside the SCMs. Pyrene's different fluorescence in hydrophobic and hydrophilic environments allows for monitoring breakage of the SCMs by fluorescence. For SCMs prepared using reversible crosslinkers 7 or 8, experiments showed that entrapped pyrene was released completely within 1 minute after the addition of $HIO_4$, or thiol 9, respectively. $HIO_4$ was used to cleave the 1,2-diol in the crosslinker derived from 2, and thiol 9 was used to cleave the disulfide bond in the crosslinker derived from 7, to the corresponding SCMs. Crosslinking moieties derived from acid-sensitive crosslinker 8 can be similarly cleaved in suitably acidic environments.

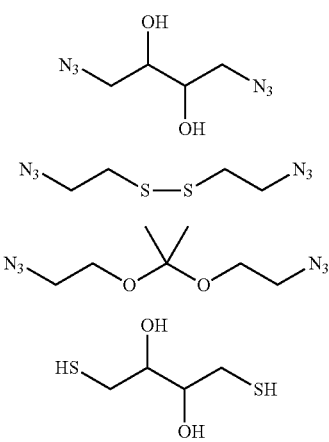

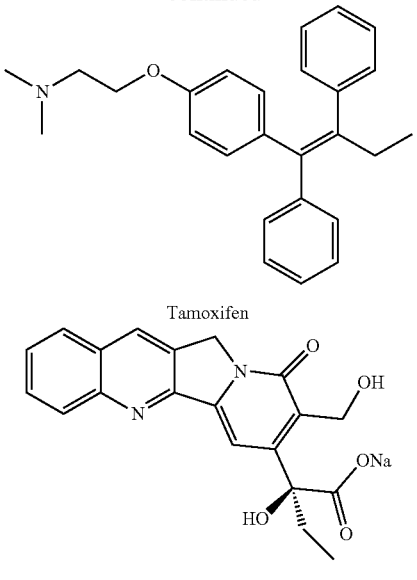

Tamoxifen

CAM-Na

Crosslinking occurs exclusively at the micelle interface because of the alkynyl group locations. The interfacial crosslinking is applicable to other systems as well. For example, crosslinked reversed micelles (CRMs) have been prepared by "thiol-alkene" addition reactions, also known as thiol-ene click chemistry. See Scheme 3 and FIG. 2. Unlike the SCMs that are soluble in water, the CRMs are soluble in nonpolar organic solvents because the hydrocarbon tails face outward.

Scheme 3. An example of a thiol-ene "click" reaction

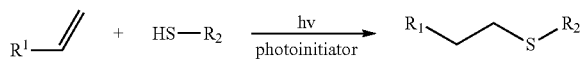

The CRMs can also extract metal ions, such as aurate ions (e.g., $AuCl_4^-$), from an aqueous solution into the organic phase as a result of the multiple ammonium headgroups in the interior. The entrapped aurate was easily reduced by sodium borohydride to afford gold nanoparticles.

A distinct advantage of this approach is the ability to prepare extremely small metal nanoparticles (for example, if not all bromide anions are exchanged into aurate) and metal alloy nanoparticles (if two or more metal precursors such as $AuCl_4^-$ and $PtCl_6^{2-}$ are used). Such metal nanoparticles are extremely difficult to prepare using other methods. The metal nanoparticles have a variety of applications in catalysis and separation technology.

Encapsulation and Release of Camptothecin

Virtually any hydrophobic drug or reagent can be encapsulated within the crosslinked micelles and nanoparticles described herein. Examples of two specific drugs that can be encapsulated in the micelles include, for example, camptothecin and tamoxifen.

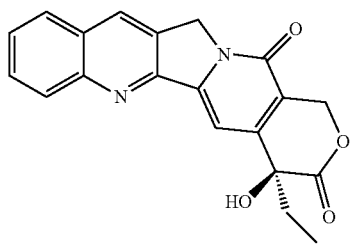

Camptothecin

Camptothecin (CAM) was isolated from a Chinese tree, *Camptotheca acuminate*, in 1966. Its high antitumor activity against a broad range of experimental tumors quickly made it a prominent lead in anticancer drug development. Because of its poor water-solubility, CAM entered clinical trials as the water-soluble sodium salt (CAM-Na). However, CAM-Na has only one-tenth of the biological activity of the parent drug. The severe dose-dependent toxicities including vomiting, diarrhea, hemorrhagic enterocolitis, leucopenia, and thrombocytopenia, stopped the development of the original drug at phase-I trials. In the late 1980s, elucidation of the mechanism of CAM activity prompted renewed interest in this drug.

An effective carrier for CAM should enhance its water-solubility, protect it from hydrolysis into the inactive carboxylate form, have high selectivity for cancerous cells using both passive and active targeting, and release the drug under acidic conditions. The crosslinking methods described herein are especially suitable to meet these challenges.

CAM is a very hydrophobic molecule, having similar water insolubility to pyrene. Because the interior of the SCMs is hydrophobic, CAM was readily solubilized in water using SCMs. Both the hydrophobic environment and the surface crosslinking protect the drug from hydrolysis. To take advantage of the EPR effect, the size of the drug carrier should ideally be about 50-200 nm. Several SCRs were prepared as described herein and were determined to have diameters of about 8-10 nm. Encapsulation of camptothecin can increase the size of the particle.

The reprecipitation method was first reported by Nakanishi and co-workers to prepare nanoparticles of water-insoluble organic compounds (*Jpn. J. Appl. Phys.* 1996, 35, L221-L223; *J. Am. Chem. Soc.* 2006, 128(50), 15944-15945). In this method, a water-insoluble compound is first dissolved in a water miscible solvent, such as acetone, alcohol, or DMSO. The organic solution is then added to an aqueous solution via a syringe under rapid stirring. Large numbers of microcrystalline seeds (typically 20-30 nm in diameter) form immediately upon mixing. Within 0.5-1 hours, these seeds typically aggregate and grow into larger nanoparticles, often hundreds of nanometers in diameter. Reprecipitation has been applied to many organic compounds, and has been scaled-up industrially, as a suitable method to prepare nanosized organic particles.

Figure 3:
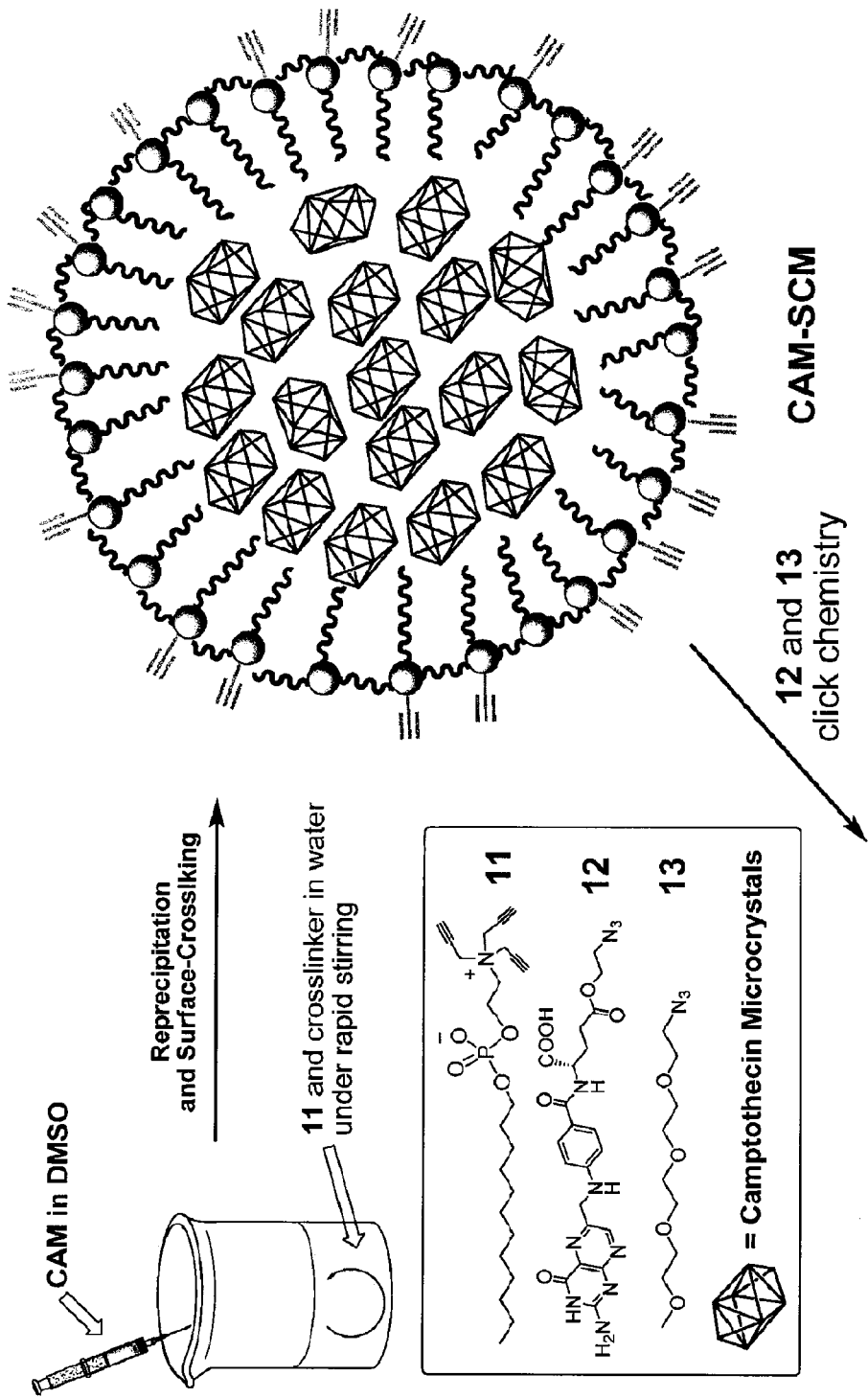
FIG. 3 illustrates preparation of surface-crosslinked camptothecin nanoparticles by precipitation and click reaction, according to an embodiment.

Preparation of CAM nanoparticles can be carried out in a similar manner, and as illustrated in FIG. 3. In the reprecipitation method, a stabilizer is typically used to protect the surface of the organic nanoparticles from further growth. The stabilizer can be a water-soluble polymer or surfactant. Although surfactant 1 may be used for this purpose, other surfactants, such as crosslinkable surfactant 11, with a phosphocholine-like headgroup, may also be used. An additional advantage is that phosphocholine lipids are the major components of mammalian cell membranes, indicating that 11 is likely to be biocompatible. The hydrophobic tail of 11 has high affinity for the nonpolar surface of CAM nanoparticles in water. Once the nanoparticles are coated with surfactant 11, further particle size growth is prohibited and a significant increase in colloidal stability is achieved.

The concentration of CAM in the organic solvent can be varied. DMSO is one suitable choice, although other solvents, such as acetone/ethanol, may be also used. The rate of stirring, the incubation time, the amount of surfactant, temperature, and the timing of crosslinking (e.g., by addition of the crosslinker and/or the copper catalyst), may also be varied. These parameters influence the size and the crystallinity of the CAM nanoparticles, which affect their bioavailability and biodistribution. The stability of the surface crosslinked nanoparticles can be varied by altering the crosslinking density and can be controlled by the amount of crosslinker (e.g., 7 and 8) and by the reaction kinetics used in preparing the nanoparticles.

For biological applications, it may be desirable to employ a catalyst other than copper ions. Copper power or wire can be suitably employed to catalyze the click chemistry reactions and it can be easily removed after reactions are complete. Alternatively, reprecipitation may be carried out at temperatures around 90° C., a temperature at which click chemistry occurs readily without catalysts.

Poly(ethylene glycol), or "PEG", can be clicked onto the surface of the micelles to avoid nonselective adsorption of proteins. PEGylation of SCMs has been performed, for example, using azido PEG derivatives 6 (see FIG. 1). The same procedure can be used to protect the surface of the CAM-SCMs.

At this stage of preparation, a single CAM particle has hundreds to thousands of drug molecules in the interior, and high loading efficiency is therefore achieved. Surface-crosslinking with a water-soluble surfactant can ensure good solubility and stability. The dimensions of the nanoparticles (50-200 nm) allows their accumulation at the cancerous sites based on the EPR effect. Surface PEGylation can ensure long circulation time of the CAM-SCMs in the blood.

Folate receptors are overexpressed on the surface of cancerous cells. Active targeting can be achieved by functionalizing the micelle surface with targeting agents, such as folate, with the use of click chemistry. After crosslinking, azido-derivatives 12 and 13 can be clicked onto the CAM-SCM surface to afford the CAM-SCM Folate (FIG. 3). The 12/13 ratio can be varied to adjust the surface-property of the nanoparticles. The short PEG derivative 13, or similar ligands, can be used instead of the polymeric version 6 to make the folate ligands more accessible to cellular receptors.

Cancerous tissues are known to be more acidic than normal tissues. Acid-triggered release is therefore a suitable release mechanism for delivery of encapsulated drugs. The acid-sensitive diazido compound 8 can be used as an acid-sensitive crosslinker.

CAM is fluorescent, thus the release of CAM from the CAM-SCMs can be monitored by fluorescence spectroscopy. Both aggregation and environmental polarity are known to affect the fluorescence of CAM. The stability of the CAM-SCMs can be readily tuned by using a combination of different crosslinkers. Crosslinking moieties derived from crosslinker 2 are completely stable under physiological conditions, whereas the disulfide bond of a crosslinking moiety derived from crosslinker 7 can be cleaved under reducing conditions provided to a cell. Mixing of 2, 7, and 8 allows for fine-tuning of the stability of the CAM-SCMs both outside and inside the cell.

Encapsulation and Release of Doxorubicin.

The crosslinking strategy may be used in liposomes, which can encapsulate hydrophilic drugs or agents. Examples of three specific drugs that can be encapsulated in crosslinked liposomes include doxorubicin (Dox), lurtotecan, and methotrexate.

Dox is currently used to treat a wide range of cancers, including acute lymphoblastic leukemia, acute myeloblastic leukemia, Wilms' tumor, neuroblastoma, soft tissue and bone sarcomas, breast carcinoma, ovarian carcinoma, transitional cell bladder carcinoma, thyroid carcinoma, gastric carcinoma, Hodgkin's disease, malignant lymphoma, and bronchogenic carcinoma. Unlike CAM, Dox is completely water-soluble. The FDA's information website for Dox states that the initial distribution half-life of approximately 5 minutes suggests rapid tissue uptake . . . while its slow elimination from tissues is reflected by a terminal half-life of 20 to 48 hours. Bioavailability is therefore not a concern, however improved methods of active targeting and controlled release are needed for Dox delivery.

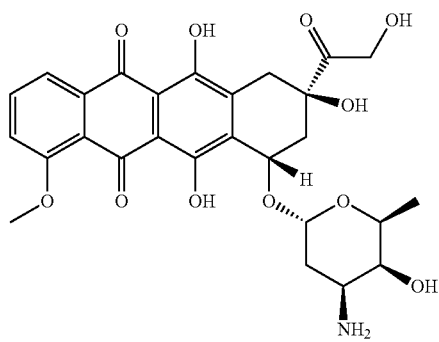

Doxorubicin

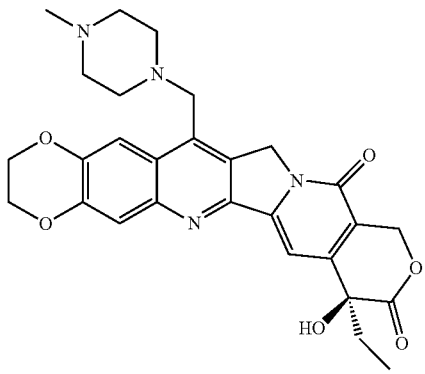

Lurtotecan

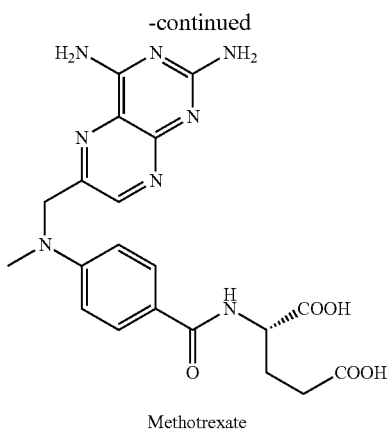

Methotrexate

A Dox delivery strategy was developed using the crosslinking methods described herein, combined with liposomal delivery. One benefit of this approach is the facile integration of the micelle technology with commercial products. Dox liposomes are currently used commercially. The Dox liposomes are well suited for targeted drug-delivery because the liposome membranes are made of the same lipids of biomembranes and surfaces decorated with receptor-specific ligands. PEGylation of the dox liposome surfaces increases the circulation time and reduces protein adsorption. However, premature leakage is a problem for the Dox liposomes because of the non-covalent liposome structure. Additionally, controlling the release of liposomal cargo is difficult.

The crosslinking methods described herein address both of these challenges concurrently. Instead of single-tailed surfactant, alkyne-functionalized phosphocholine derivative 14 can be prepared using standard synthetic techniques. Lipid 14 may be used with the common phospholipid POPC (palmitoyl-oleoyl phosphatidylcholine, 15) to form negatively charged liposomes.

Carboxyfluorescein (CF) is a water-soluble dye. To investigate controlled release of liposomal content, CF was used as a model drug for hydrophilic chemotherapeutic agent. CF-leakage assays are well known and are widely used in liposomal chemistry. In this assay, large unimolecular vesicles (LUVs) are first prepared in the presence of a self-quenching concentration (>50 mM) of CF. The external, untrapped CF can then be removed by gel permeation chromatography. If CF leaks out of the LUVs, it becomes diluted and then fluoresces more intensely.

Figure 20:
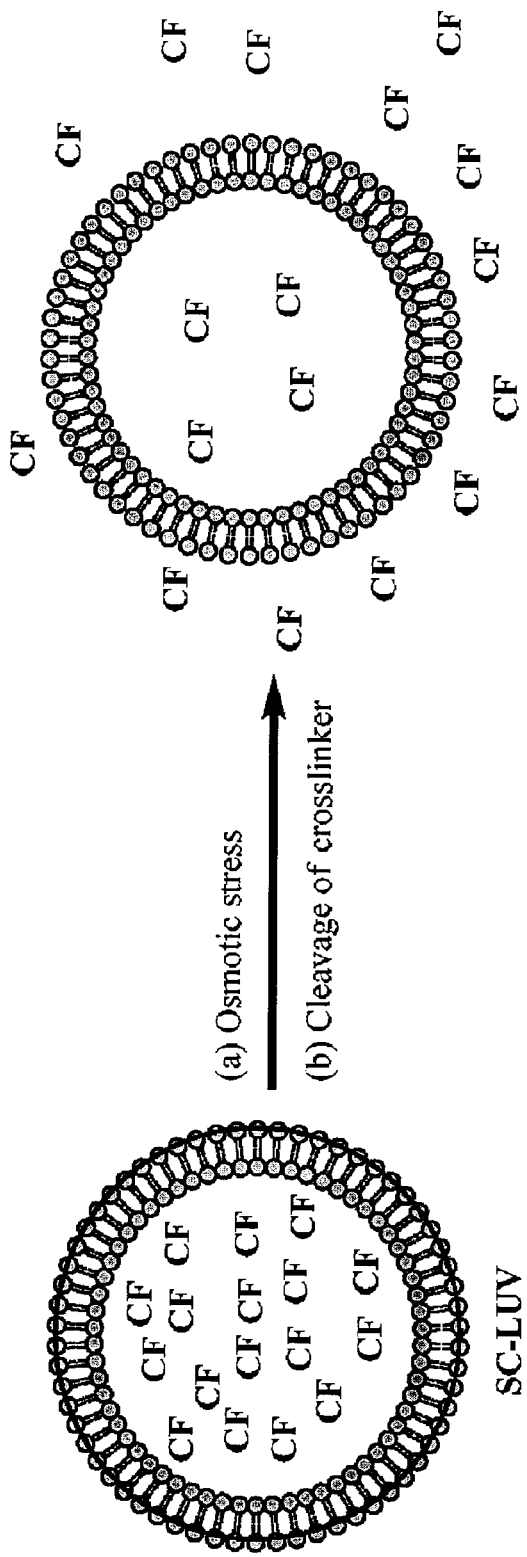
FIG. 20 illustrates the release of carboxyfluoroscein (CF) from osmotically stressed SC-LUV approach enables controlled release of drugs by specific stimuli and is more effective at preventing premature drug-release than physical entrapment-features of particular importance in the delivery of drugs with high cytotoxicity. It has been reported, for example, that physically entrapped anticancer drugs display as high cytotoxicity as the small molecule versions (Y. Bae, K. Kataoka, *Adv. Drug. Deliv. Rev.* 2009, 61, 768). Nonetheless, covalent linking between the drug and the delivery vehicle puts significant constraints on the structure of both components and adds considerable complexity to the production and formulation of the therapeutic package.

Controlled release of CF from the LUVs is illustrated in FIG. 20. CF-containing LUVs can be prepared with either 14, or a mixture of 14 with other non-crosslinkable lipids (e.g., POPC/POPG). Click reactions with redox-sensitive 7 can crosslink mainly the outer leaflet of the lipid bilayer. When the surface crosslinked LUV (SCL-LUV) is placed in a concentrated salt solution (e.g., 5 M NaCl), the liposomes experience osmotic stress. With a sufficiently high crosslinking density, the SCL-LUV can withstand the osmotic pressure and keep CF inside. Upon cleavage of the crosslinker under reducing conditions, the noncovalently linked LUV ruptures easily, releasing the entrapped contents. The same method may be used with acid-sensitive 8 as the crosslinker, but the CF assay is not suitable under acid conditions. Other assays such as ANTS/DPX assay may be more suitable to monitor the controlled release.

The relationship between liposomal stability and crosslinking density can be studied systematically by varying the 14/15 in the lipid formation. Highest crosslinking, and thus highest stability, can be achieved for the SCL-LUV with 14 as the only lipid, whereas no crosslinking is achieved if only 15 is employed. Stability of the SCL-LUV can be measured by either the maximum osmotic pressure it can tolerate without leakage, or by the percent leakage of CF over time under a given osmotic pressure.

The basic strategies for the passive and active targeting are the same in the CAM-SCMs (FIG. 3). Briefly, passive target-

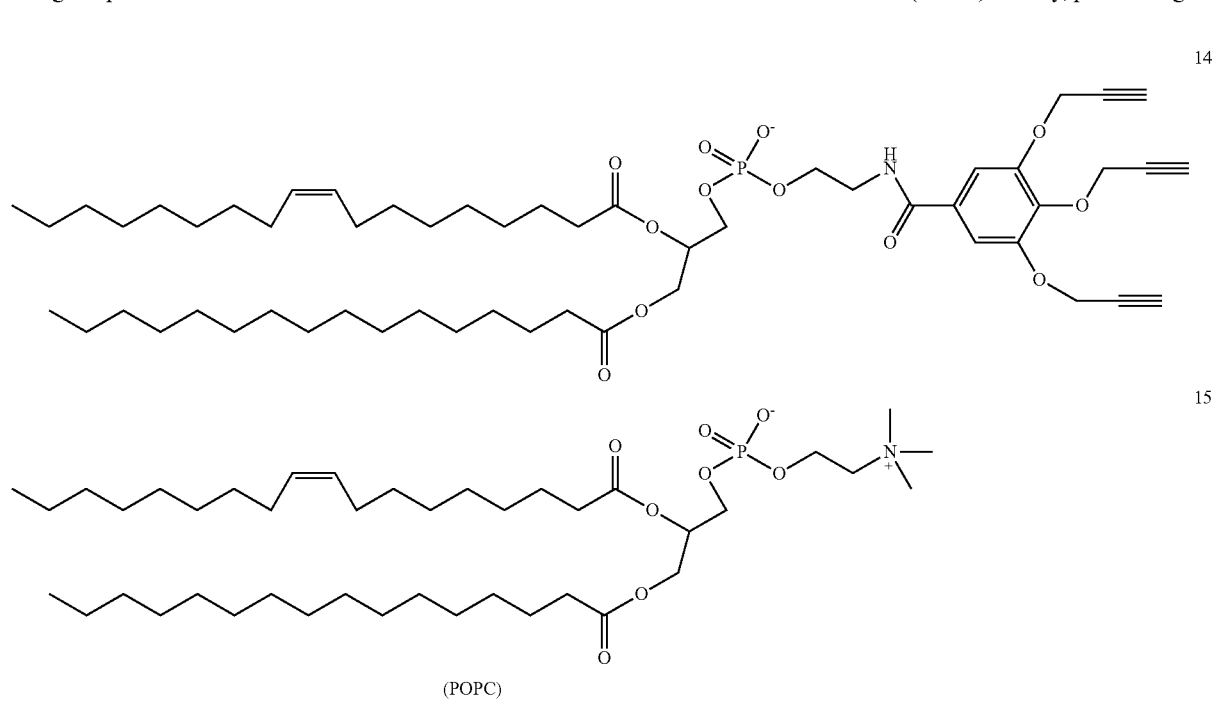

ing is achieved by controlling the size of the liposomes (100-200 nm) and PEGylation (to avoid protein adsorption), and active targeting by post-functionalization by folate derivative 12. These procedures provide the ability to control the size, stability, surface-functionalization of the particles, and the release of both water-insoluble and water-soluble anticancer drugs from the particles.

Micelle Embodiments

The invention therefore provides a variety of novel organic particle. In some embodiments, the particle can have surface crosslinked non-polymeric organic amphiphiles. Polar head groups of the amphiphiles can be covalently crosslinked to each other at the surface of the particle through triazole groups or thioethers groups. The tail groups of the amphiphiles can then be arranged toward the interior of the particle. These particles can be water-soluble.

Amphiphiles Used to Prepare the Particles. In some embodiments, the particles are spheroid and comprise about 10 to about 150 crosslinked amphiphiles and about 10 to about 150 crosslinking moieties. In other embodiments, the particle can include larger amounts of amphiphiles and crosslinking moieties, such as 20 to about 200, to about 250, to about 500, or to about 1000. When the particles are prepared as rod-like shaped particles, the particles are typically prepared from a larger number of amphiphiles, such as about 100 to about 1000, or about 500 to about 5000 amphiphiles. The ratio of amphiphiles to crosslinking moieties can be from about 1:10 to about 10:1, or any integer ratio in between those ratios.

The tail groups of the amphiphiles can be non-polar groups such as alkyl groups, fluoroalkyl groups, or a combination thereof. The alkyl or fluoroalkyl groups can contain any suitable number of carbons such that the amphiphiles self-assemble and form micelles. Accordingly, in some embodiments the tail group can include about 6 to about 50 carbon atoms in a chain, wherein the chain can be straight or branched. The groups can also be ($C_{20}$-$C_{50}$) alkyl groups or fluoroalkyl groups, ($C_6$-$C_{25}$) alkyl groups or fluoroalkyl groups, ($C_6$-$C_{22}$) alkyl groups or fluoroalkyl groups, ($C_6$-$C_{20}$) alkyl groups or fluoroalkyl groups, or ($C_8$-$C_{18}$) alkyl groups or fluoroalkyl groups. The tail groups can optionally include a group that links the tail to the head group of the amphiphile or that links the tail group to another section of the tail group. The linking group can be, for example, an ester, imine, boronate, or disulfide group. The linking group can also be a salt bridge, such as a guanidinium-carboxylate or guanidinium-phosphate salt bridge.

In some embodiments, the tail groups are non-polar alkyl or fluoroalkyl chains on the interior of the particle and the head groups are polar groups at the surface of the particle. In such embodiments, the particle has a hydrophobic core and a hydrophilic exterior. A non-polar tail may be removed by hydrolysis if it is connected to the head group by ester, imine, boronate, or other hydrolyzable linkage, to provide a polar tail. The tail may be partly or completely destroyed if it consists of functional groups that can be degraded. For example, an unsaturated hydrocarbon tail may be degraded by oxidation, or the tail may be removed by reduction if it is connected to the head group by disulfide bonds. The tail may also be removed if it is connected to the head group by noncovalent bonds such as guanidinium-carboxylate or guanidinium-phosphate salt bridges. Thus, in other embodiments, such as when interior tail groups are non-polar and a hydrolyzable linking group is hydrolyzed to provide a polar tail moiety, the tail groups of the amphiphiles are polar and the particle has a hydrophilic core and a hydrophilic exterior. Accordingly, the tail groups of the amphiphiles arranged toward the interior of the particle can be non-polar hydrocarbon or fluorocarbon tail groups, polar tail groups, or a combination thereof.

Properties and Forms of the Organic Particles. The organic particle can be in the form of spheres or rods. The particles can also be in the form of a liposome or vesicle having a bilayer of amphiphiles, where the bilayer includes one or more water compartments between the bilayer of amphiphiles. The preparation of vesicles is described in Example 5 below.

Particle Cargo and Appendages. The organic particle can include one or more cargo molecules within the particle or at the surface of the particle. The cargo can be free within the interior of the particle or covalently bonded to a tail group of an amphiphile. The cargo can also be bonded to the surface of the particle though electrostatic interactions, or the cargo molecules can be optionally covalently bonded to the surface of the particle, for example, through a linking group such as a group that has been bonded to a surface functional group (e.g., an alkyne, azide, alkene, or thiol moiety) through a click reaction.

The cargo molecules can be a drug, an organic nanoparticle, an inorganic nanoparticle, a fluorophore, a diagnostic agent, and/or a catalyst. The catalyst can be an organic molecule catalyst, an organometallic catalyst, or a transition metal catalyst. In some embodiments, the catalysts are phosphine-stabilized rhodium catalysts for catalytic hydrogenation and/or hydroformylation. In some embodiments, the catalysts are phosphine-stabilized palladium catalysts for metal-catalyzed cross-coupling. In other embodiments, the catalysts are metallosalen complexes for catalytic epoxidation or other reactions.

The surface of the particle can include one or more surface groups such as alkynes, alkenes, azides, aldehydes, or alcohols, or attached groups such as water-soluble polymers, fluorophores, biological ligands, nucleic acids, nucleic acid analogues, catalysts, or a combination thereof. The biological ligands can be active targeting agents, sugar or peptide moieties, or analogues thereof. The surface groups can be receptors for ligands on a biological host, or ligands for receptors on a biological host. The biological host can be a bacterium, a virus, or a eukaryotic cell. The surface functional groups can be attached to the surface of the particle by using click reactions with appropriately functionalized groups above. The surface of the particle can be functionalized with about 10 to about 150 functionalized surface groups; or about 100 to about 5000 functionalized surface groups.

The surface crosslinking can be reversible or degradable. For example, in some embodiments the surface crosslinking can be cleaved by heat, by a change in pH, by a reducing agent, or by a combination thereof. Accordingly, the cleavage can be under chemical conditions including contacting the particle with a reducing agent, an acid, or a periodate compound, and the like.

Crosslinked Reverse Micelle Particles. In some embodiments, the organic particles can be considered crosslinked reverse micelle particles. The amphiphiles used to prepare these particles can be the same as used for the surface crosslinked micelle particles described above, however the particles are prepared differently, thereby providing different physical and chemical properties to the particles. Thus, the invention provides an organic particle comprising non-polymeric crosslinked amphiphiles; where the amphiphiles comprise one or more nonpolar alkyl or fluoroalkyl chains and one or more polar head groups; the nonpolar chains are located on the exterior of the particle and the polar head groups are oriented toward the interior of the particle; and the amphiphiles are covalently crosslinked to each other near the head groups through triazole groups or thioether groups. The particles can be a crosslinked reverse micelle (CRM) particle and the particle can be soluble in organic solvents.

The organic particle can contain one or more metal salts or metal particles within the particle. The particle can have one or more catalytically active groups oriented toward the interior of the particle, such as on a polar head group. The catalytically active groups can be one or more of carboxylic acids, sulfonic acids, amines, or thiols, where the catalytically active groups are covalently bonded to one or more of the amphiphiles.

Surface Crosslinked Organic Particles Prepared by Azide-Alkyne Click Reactions. The invention provides methods for preparing surface-crosslinked organic particles, as described in the summary above, by inducing cycloaddition between the alkynes and azides, thermally or with a suitable catalyst, to covalently crosslink the amphiphiles to each other near the head groups through formation of triazole groups. The amphiphiles can self-assemble through hydrophobic interactions among the hydrophobic groups. In some embodiments, the amphiphiles include one or more non-polar alkyl tails and a tripropargylammonium head group or a dipropargyl(alkyl)ammonium head group. The surface-crosslinked particle can be water soluble. The catalyst used to facilitate the click reaction can be a copper catalyst, such as a Cu(I) salt or a Cu(II) salt reduced in-situ to Cu(I).

In some embodiments, the crosslinking agents comprise two or more azido groups when the polar head groups comprise alkynyl groups, or two or more alkynyl groups when the polar head groups comprise azido groups. When preparing the particles, the amphiphiles and water can be in the presence of one or more cargo molecules. The cargo molecules are thereby encapsulated in the hydrophobic core upon formation of the self-assembled structure. In some embodiments, the cargo molecules are hydrophobic. In other embodiments, hydrophobic tails of the amphiphiles at the interior of the particle are hydrolyzed from esters to carboxylic acid or hydroxyl groups, and the cargo molecules are hydrophilic. In some embodiments, the amphiphiles and water are in the presence of one or more cargo molecules, the particles are in the form of vesicles, and the cargo molecules are encapsulated in water compartments of the vesicles.

In preparing the particles, the methods can further include contacting the surface-crosslinked particle with one or more azido-containing or alkynyl-containing compounds that are water-soluble polymers, fluorophores, biological ligands, nucleic acids or analogues thereof, or a combination thereof. Cycloaddition can be induced between alkynes or azides on the surface of the particle with the azido-containing or alkynyl-containing compounds. The cycloaddition can be induced thermally or with a suitable catalyst to provide a water soluble multivalent particle that has a plurality of water-soluble polymers, fluorophores, biological ligands, nucleic acids or analogues thereof, or a combination thereof, linked to the surface of the particle through triazole groups.

Surface Crosslinked Organic Particles Prepared by Thiol-ene Click Reactions. The invention provides methods for preparing surface-crosslinked organic particles, as described in the summary above, by inducing thiol-ene addition between alkenes of the amphiphiles and thiol groups of the crosslinkers photochemically to covalently crosslink the amphiphiles to each other near the head groups through the formation of thioether groups. In some embodiments, the amphiphiles include one or more non-polar alkyl tails and a triallylammonium head group, to provide a self-assembled water soluble micelle. The induction of the thiol-ene addition between the alkenes of the amphiphiles and the thiol groups can be carried out in the presence of a photoinitiator.

The particles can be prepared such that the amphiphiles and water are in the presence of one or more cargo molecules. The cargo molecules are thereby encapsulated in the hydrophobic core upon formation of the self-assembled structure. In some embodiments, the cargo molecules are hydrophobic, and in other embodiments, the cargo molecules are hydrophilic. In other embodiments, the amphiphiles and water are in the presence of one or more cargo molecules, the particles are in the form of vesicles, and the cargo molecules are encapsulated in water compartments formed within the vesicles. As discussed above, the cargo molecules can be one or more of drugs, organic nanoparticles, inorganic nanoparticles, fluorophores, diagnostic agents, and catalysts.

In some embodiments, the method further includes contacting the surface-crosslinked particle with one or more thiol-containing compounds comprising water-soluble polymers, fluorophores, biological ligands, nucleic acids or analogues, or a combination thereof. Thiol-ene addition reactions can be induced between the thiol groups of the thiol-containing compounds and alkene groups at the surface of the surface-crosslinked particle to provide a water soluble multivalent particle that has a plurality of surface functional group compounds linked to the surface of the particle through thioether groups. These surface groups can be water-soluble polymers, fluorophores, biological ligands, nucleic acids or analogues thereof, or a combination thereof, linked to the surface of the particle through thioether groups. The biological ligands can include sugar or peptide moieties, or analogues thereof.

Additional Methods of the Invention. The invention also provides methods to form metal nanoparticles. A metal salt and a plurality of particles described above, such as a particle with a hydrophilic interior, can be contacted in an aqueous/organic solvent mixture, thereby extracting metal ions of the metal salt into the organic solvent. The metal ions then migrate to the interior of the particle, to provide a crosslinked organic particle encapsulating metal ions. The crosslinked organic particle encapsulating metal ions can be contacted with a reducing agent, thereby reducing the metal ions in the interior of the crosslinked organic particle, to provide the metal nanoparticles. The metal salt can include metals such as $AuX_4^-$, $PtX_6^{2-}$, $PdX_4^{2-}$, where X is a halogen, for example, $AuCl_4^-$, $PtCl_6^{2-}$, $PdCl_4^{2-}$, or a combination thereof. More than one type of metal salt can contacted with the crosslinked organic particle in order to form alloys. In some embodiments, the metal nanoparticle formed has a diameter of 1 nm (or about 3-4 atoms) to about 100 nm, or about 1.5 nm to about 10 nm, or about 2 nm to about 5 nm.

The invention further provides a therapeutic method comprising administering to a patient in need therapy an effective amount of the delivery system that includes a plurality of particles described above, where the surface crosslinking of the particles encapsulate one or more drugs, the surface crosslinking of the particles is cleaved in vivo, and the drug of the particles is released into the body of the patient, thereby providing the drug to the patient. In some embodiments, a crosslinked micelle is used for the delivery of hydrophobic drugs. In other embodiments, a crosslinked vesicle is used for the delivery of hydrophilic drugs.

While various embodiments of the invention have been described above, the invention also provides the following embodiments. In one embodiment, the invention provides a multivalent surface-crosslinked micelle (SCM) particle comprising about 10 to about 150 crosslinked amphiphiles and about 10 to about 150 crosslinking moieties. The crosslinkiner moieties, such as those derived from the compounds illustrated in Schemes 6 and 11 below, can link one amphiphile to another, thereby stabilizing the micelle by the formation of triazole linkages, or thioether linkages, resulting from the click chemistry reactions used to crosslink the amphiphiles.

The amphiphiles include non-polar alkyl chains, such as $(C_{10}$-$C_{20})$alkyl chains, on the interior of the particle and polar head groups at the surface of the particle. The head groups can be tripropargylammonium groups or tryallylammonium groups that are covalently crosslinked to each other by the crosslinkers, thereby forming triazole groups or thioether groups. The head groups orient themselves at the surface of the particle, thereby making the particle water soluble.

The particle can have one or more drugs or diagnostic agents encapsulated within the particle. Examples of such drugs include camptothecin and doxorubicin. Accordingly, the encapsulated agents, i.e., the drug or diagnostic agent, can be hydrophobic or hydrophilic.

The surface of the particle can have functionalized with about 10 to about 150 alkyne or alkene groups available for linking to surface modifying groups that include various functional groups. The functional groups can be water-soluble polymers, sugars, fluorophores, active targeting agents, or a combination thereof. The functional groups can be binding sites for a bacteria, virus, or tumor cell.

Any of the crosslinked micelles described herein may be crosslinked with reversible crosslinkers. For example, when the surface of the micelle crosslinked with reversible crosslinkers is contacted with an appropriate acid, reducing agent, or diol cleaving agent, the crosslinkers are cleaved, thereby eliminating the crosslinking and allowing encapsulated agents to be released from the micelle. Thus the particles can be used for the controlled release of drugs, such as camptothecin or doxorubicin, among other agents. Accordingly, the invention provides a deliver system that includes a plurality of multivalent particles described herein, and a pharmaceutically acceptable diluent or carrier.

The invention also provides a crosslinked reverse micelle (CRM) particle that includes about 10 to about 150 crosslinked amphiphiles and about 10 to about 150 crosslinking moieties. The amphiphiles of the micelle have non-polar alkyl chains, such as $(C_{10}$-$C_{20})$alkyl chains, facing the exterior of the particle and polar head groups at the interior of the particle. The head groups at the interior of the particle are covalently crosslinked to each other by crosslinkers through triazole groups or thioether groups, and the particle is soluble in organic solvents, such as alkane solvents, acetone, DMSO, and the like.

Crosslinked reverse micelle particle can include one or more metal salts or metal particles within the particle. Examples of such particles include gold nanoparticles, palladium nanoparticles, or alloys thereof.

The invention also provides a method for preparing a surface-crosslinked micelle (SCM) particle. The method can include combining a plurality of amphiphilic organic compounds and water, wherein the amphiphilic organic compounds comprise one or more non-polar alkyl tails and a tripropargylammonium head group, to provide water soluble micelles. The micelles can be contacted with a suitable copper catalyst and a diazido-functionalized crosslinking agent, to provide the surface-crosslinked micelle particle. The contacting, which results in a click reaction, can be aided by the addition of a salt, such as sodium ascorbate. The resulting particle typically includes about 10 to about 150 crosslinked amphiphiles and about 10 to about 150 crosslinking moieties. The non-polar alkyl chains are oriented to the interior of the particle and polar head groups are at the surface of the particle. The head groups at the surface of the particle are covalently crosslinked to each other by crosslinkers through triazole groups, and the surface-crosslinked micelle has about 10 to about 150 alkyne groups at the surface of the particle.

The amphiphilic organic compounds can form micelles in the presence of a hydrophobic drug or diagnostic agent. The resulting particles can therefore include a hydrophobic drug or diagnostic agent encapsulated by the surface-crosslinked micelle.

The method can also include functionalizing the surface of the particle by contacting the surface-crosslinked micelle particle with a suitable copper catalyst and one or more azido-containing functional group compounds to form linkages to the functional groups using click chemistry. The functional groups can include, for example, water-soluble polymers, sugars, fluorophores, active targeting agents, or a combination thereof. The resulting particles are water soluble multivalent surface-crosslinked micelle particles that have a plurality of functional group compounds linked to the surface of the surface-crosslinked micelle particle through triazole groups.

In another embodiment, the invention provides a method for preparing a surface-crosslinked micelle (SCM) particle by combining a plurality of amphiphilic organic compounds and water, wherein the amphiphilic organic compounds comprise one or more non-polar alkyl tails and a triallylammonium head group, to provide water soluble micelles. The micelles can then be irradiating the micelles in the presence of a photoinitiator and a dithio-functionalized crosslinking agent, to provide surface-crosslinked micelle particles. The surface-crosslinked micelle particle typically include about 10 to about 150 crosslinked amphiphiles and about 10 to about 150 crosslinking moieties. The non-polar alkyl chains are oriented to the interior of the particle and polar head groups are at the surface of the particle, the head groups at the surface of the particle are covalently crosslinked to each other by crosslinkers through thioether groups, and the surface-crosslinked micelle particle has about to about 150 alkene groups at the surface of the particle.

The amphiphilic organic compounds can form micelles the presence of a hydrophobic drug or diagnostic agent. The hydrophobic drug or diagnostic agent is thereby encapsulated by the surface-crosslinked micelle.

The method can further include irradiating the surface-crosslinked micelle particle in the presence of a photoinitiator and one or more thiol-containing functional group compounds to modify the surface of the particle. The functional groups can include water-soluble polymers, sugars, fluorophores, active targeting agents, or a combination thereof. The resulting particle is a water soluble multivalent surface-crosslinked micelle particle that has a plurality of functional group compounds linked to the surface of the surface-crosslinked micelle particle through thioether groups.

In yet another embodiment, the invention provides a method for preparing a crosslinked reverse micelle (CRM) particle. The method can include combining a plurality of amphiphilic organic compounds, water, and a suitable organic solvent mixture. The organic solvent mixture can include a halogenated organic solvent, such as methylene chloride and/or chloroform, and a $(C_6$-$C_{12})$alkane solvent, such as hexane, heptane, or octane. The amphiphilic organic compounds can include one or more non-polar alkyl tails and a triallylammonium head group, thereby providing the reverse micelles; wherein the reverse micelles comprise amphiphiles that have non-polar alkyl chains on the exterior of the particle and polar head groups at the interior of the particle. The particles can be irradiated in the presence of a photoinitiator and a dithio-functionalized crosslinking agent, to provide the crosslinked reverse micelle particles. The particle typically includes about 10 to about 150 crosslinked amphiphiles, about 10 to about 150 crosslinking moieties linking the amphiphiles together. The non-polar ($C_{10}$-$C_{20}$) alkyl chains are oriented to the exterior of the particle and polar head groups are at the surface of the particle, the head groups at the surface of the particle are covalently crosslinked to each other by crosslinkers through thioether groups, and the particle is soluble in organic solvents.

The crosslinking agent used in any of the methods above can be reversible crosslinking agent, which can be cleaved in the presence of, for example, a reducing agent, an acid, or a periodate compound.

In another embodiment, the invention provides a method of forming a metal nanoparticle. The method can include contacting a metal salt and a plurality of reversed micelle particles, in an aqueous/organic solvent mixture, thereby extracting the metal cation of the metal salt into the organic solvent, to provide crosslinked reverse micelles encapsulating metal cations. After separation from the aqueous solvent, the crosslinked reverse micelles encapsulating metal cations can be contacted with a reducing agent, thereby reducing the metal cation in the interior of the crosslinked reverse micelles, to provide the metal nanoparticle. The metal salt can include, for example, $AuCl_4^-$, $PdCl_4^{2-}$, or a combination thereof. More than one type of metal salt can be present in the aqueous/organic solvent mixture that is contacted with the crosslinked reverse micelles, resulting in the formation of a metal nanoparticle that is an alloy of two or more different metals.

The invention further provides a therapeutic method that includes administering to a patient in need therapy an effective amount of drug or diagnostic agent encapsulating particles described herein. The particles can be a deliver system as described above, wherein the surface crosslinking of the micelles encapsulate one or more drugs, the surface crosslinking of the micelles is reversible, the surface crosslinking is reversed in vivo, and the drug of the micelle is released into the body of the patient, thereby providing therapy to the patient.

In some embodiments, the amphiphiles used to form the micelles described herein can be a compound of formula I:

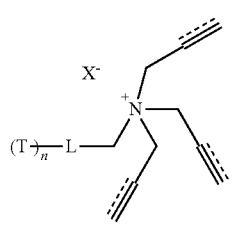

(I)

wherein T is a hydrophobic ($C_{10}$-$C_{20}$)alkyl tail connected to L through a covalent linkage such as an ether, ester, amine, amide, siloxane, imine, carbamate, urea, disulfide, thiother, or a direct bond;

L is a linking group, wherein the linking group comprises -Ph-, >N—C(O)—, —O—C(O)—, one to six methylene groups, or a combination thereof, or L is a direct bond;

n is one, two, or three;

the dashed lines are optional bonds, which form alkynes when present or alkenes when absent; and X is a suitable counter ion, such as halo, for example, F, Cl, Br, or I. Examples of suitable crosslinker compounds of Formula I are illustrated in Scheme 5 below.

Scheme 5. Examples of Crosslinkable Amphiphiles

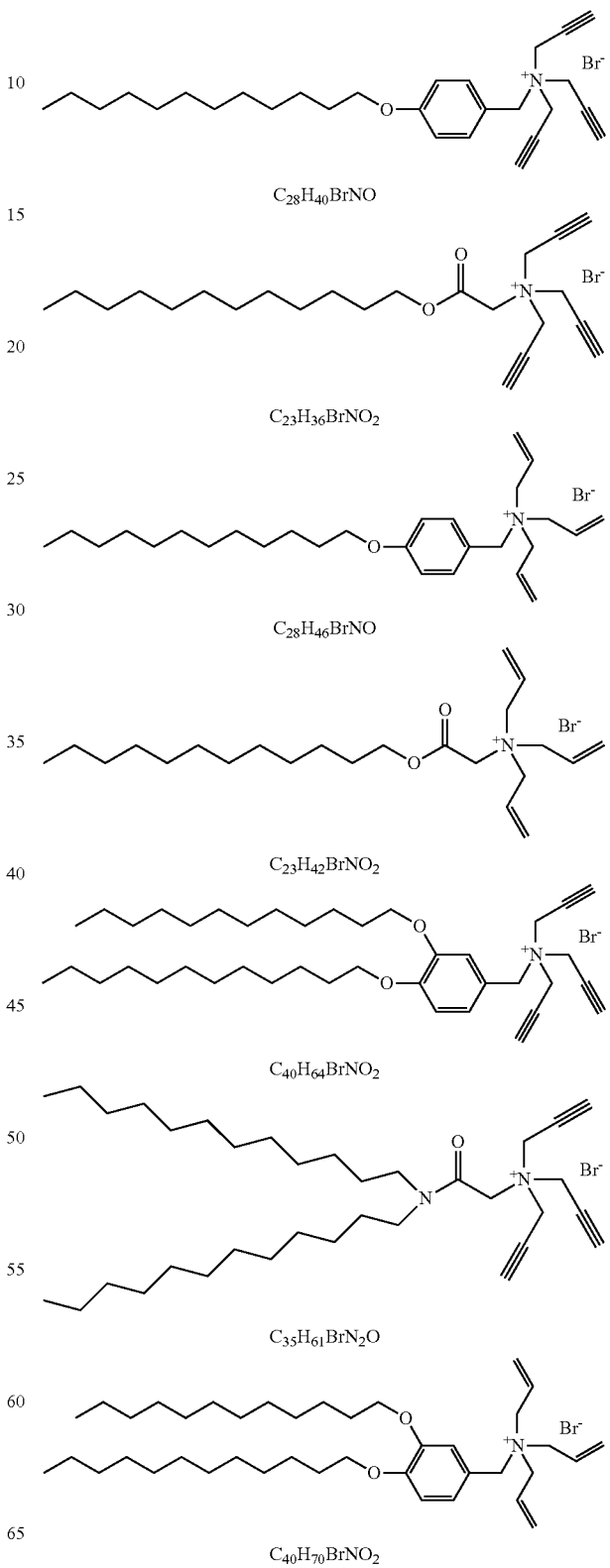

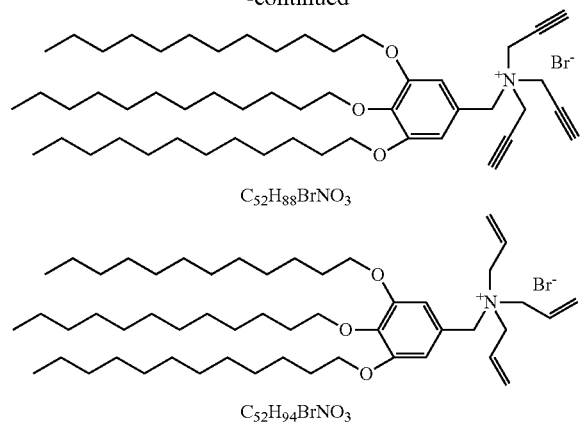
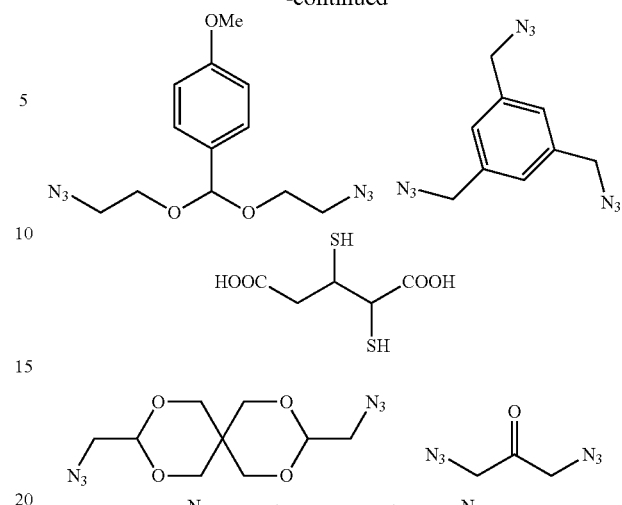
Crosslinkers can be crosslinked by click reactions using crosslinking agents, such as those illustrated in Scheme 6.
Scheme 6. Examples of Crosslinking Agents
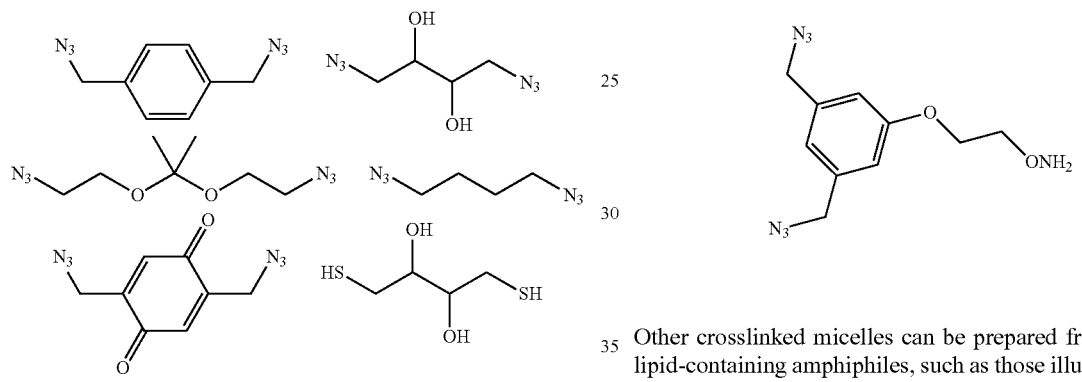
Other crosslinked micelles can be prepared from phospholipid-containing amphiphiles, such as those illustrated below in Schemes 7-10.
Scheme 7. Example of a Phospholipid-containing Amphiphile
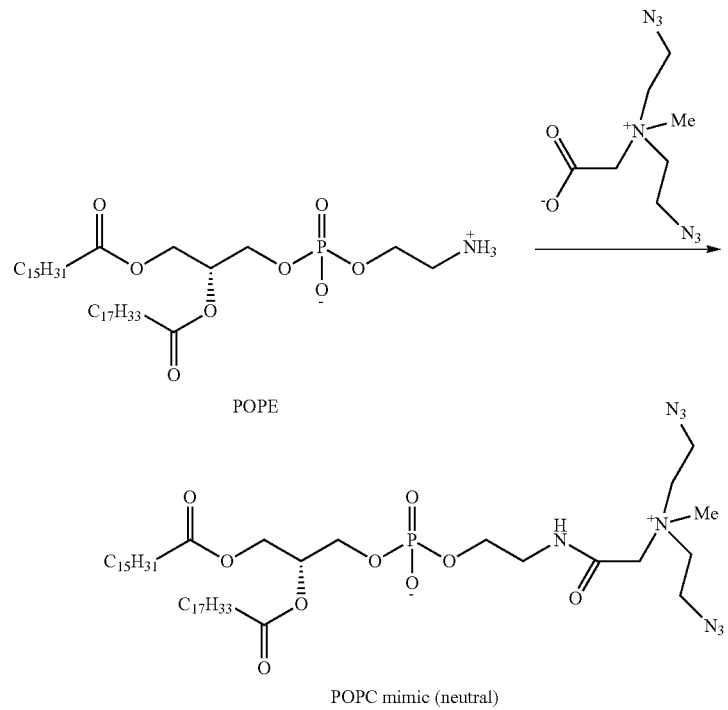

Scheme 8. Example of a Phospholipid-containing Amphiphile
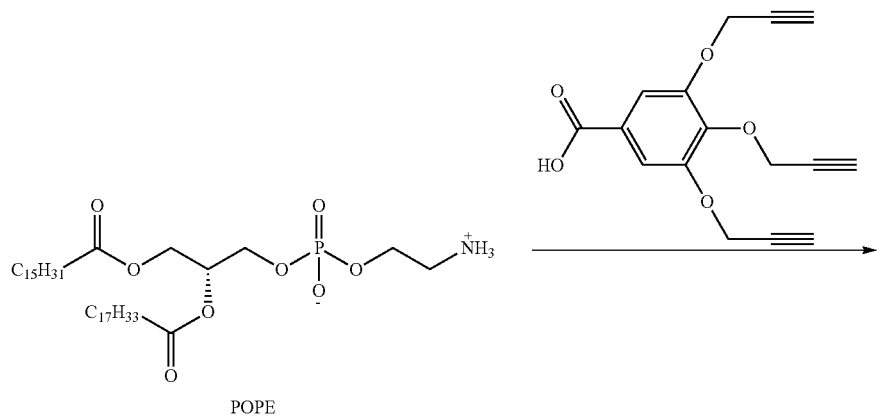
POPE
POPA mimic (Anionic)
Scheme 9. Example of a Phospholipid-containing Amphiphile
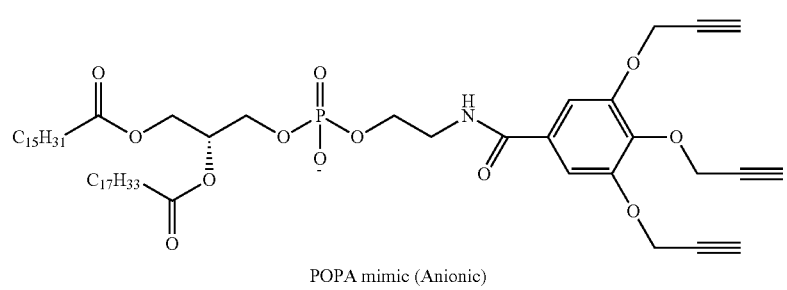
POPE
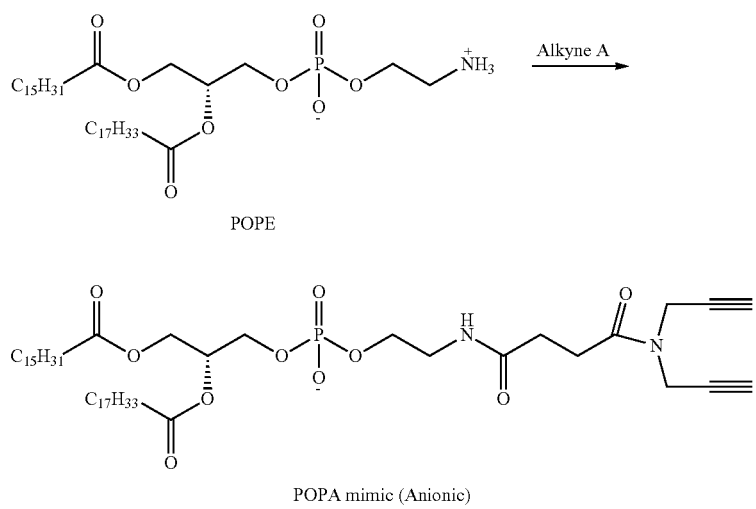
POPA mimic (Anionic)
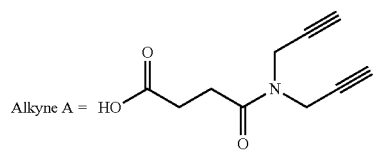
Alkyne A =

Scheme 10. Example of a Phospholipid-containing Amphiphile
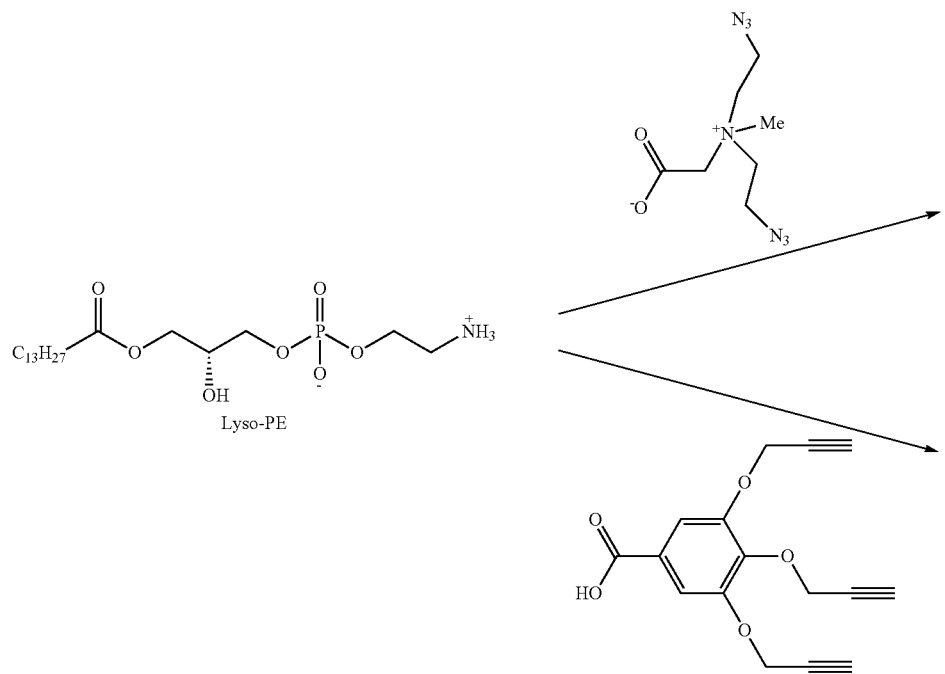
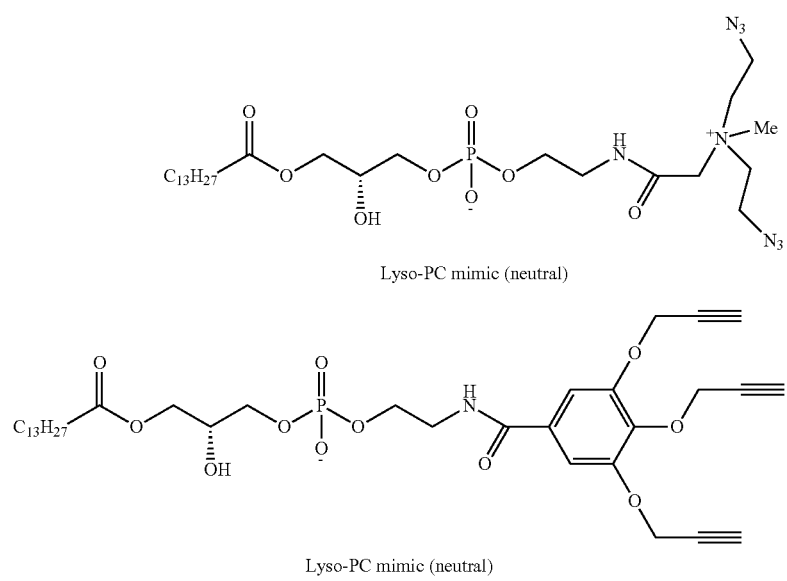
Lyso-PC mimic (neutral)

In some embodiments, the amphiphiles can have two or three azido groups and the crosslinkers can include two or three alkyne groups, such as those illustrated in Scheme 11.

Scheme 11. Examples of Alkyne-Containing Crosslinkers

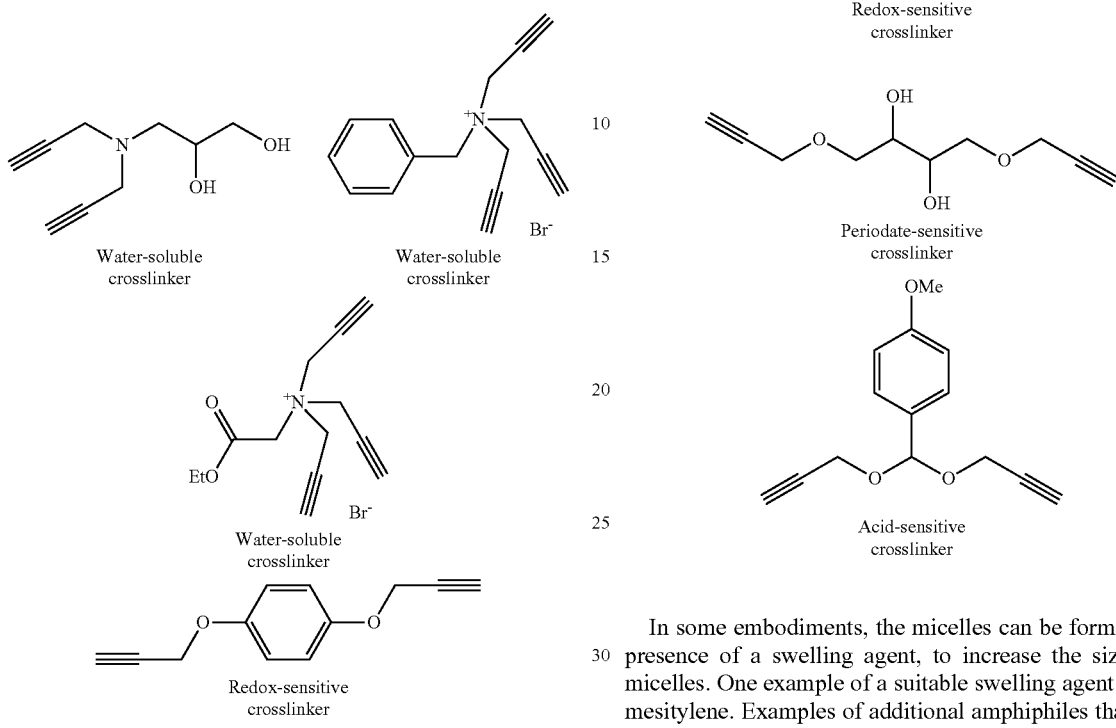

In some embodiments, the micelles can be formed in the presence of a swelling agent, to increase the size of the micelles. One example of a suitable swelling agent includes mesitylene. Examples of additional amphiphiles that can be crosslinked are illustrated in Schemes 12-14 below.

Scheme 12. Examples of Cationic Amphiphiles with Multiple Alkynyl or Azido Groups

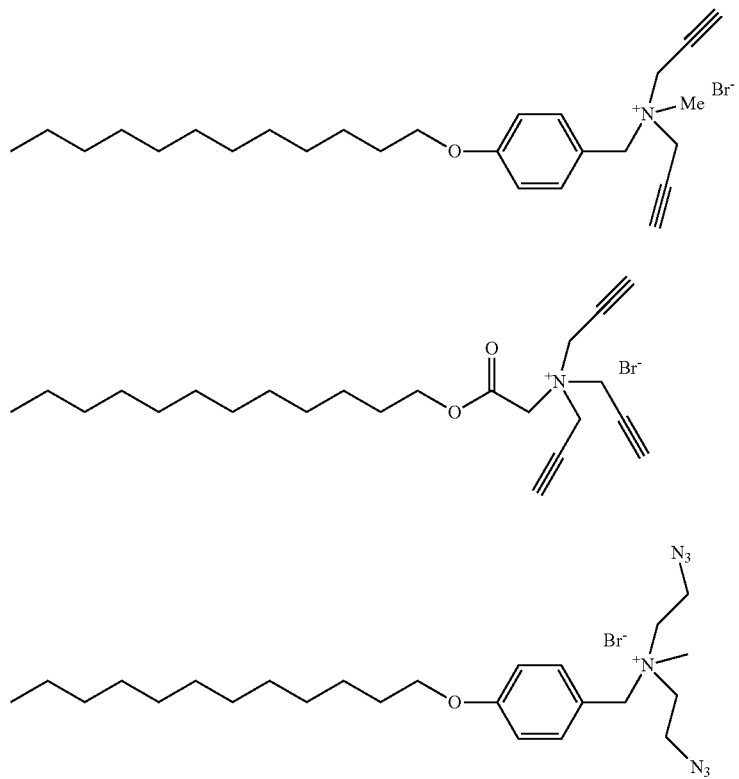

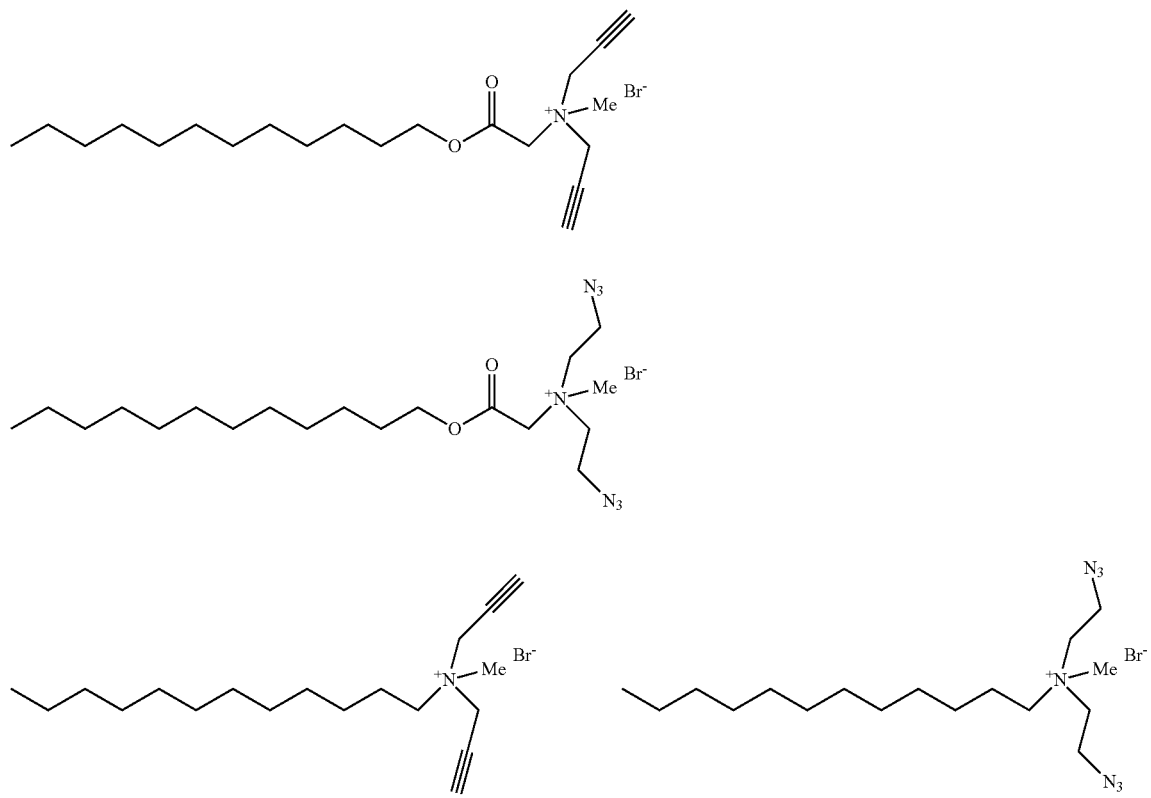
Scheme 13. Examples of Neutral Amphiphiles with Multiple Alkynyl or Azido Groups
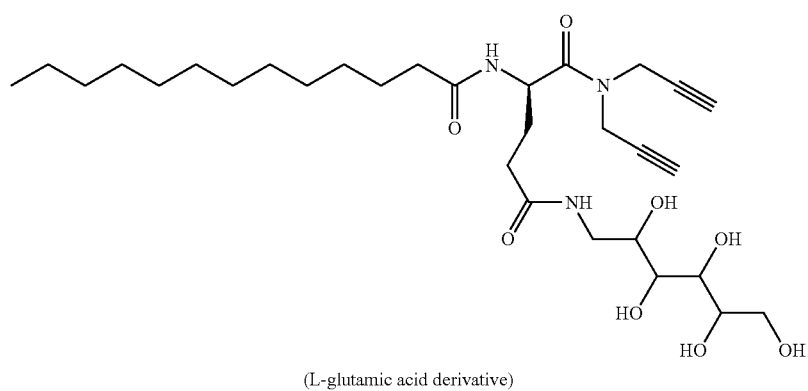
(L-glutamic acid derivative)
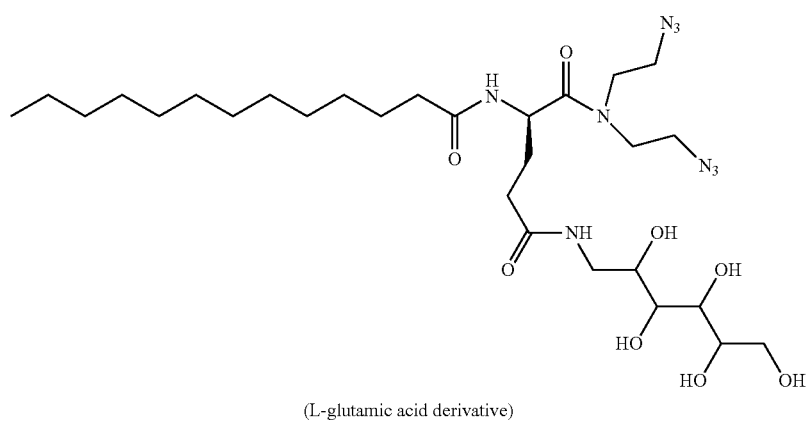
(L-glutamic acid derivative)

-continued
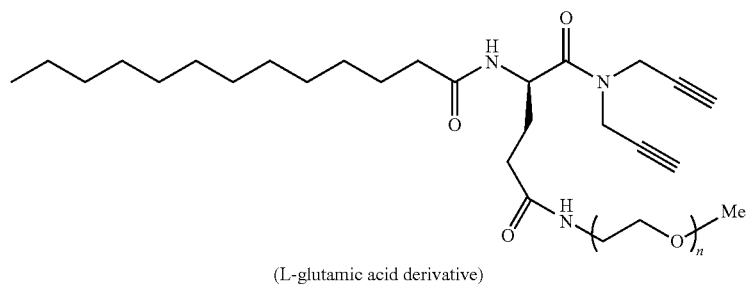
(L-glutamic acid derivative)
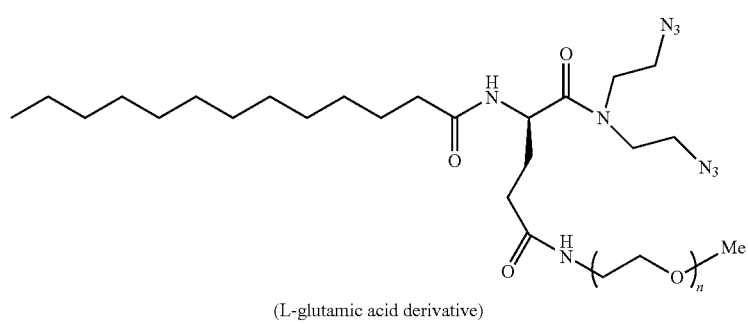
(L-glutamic acid derivative)
where "n" is 1 to about 100.
Scheme 14. Examples of Anionic Amphiphiles with Multiple Alkynyl or Azido Groups
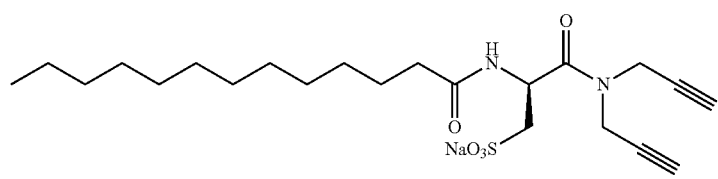
(L-cysteine derivate)
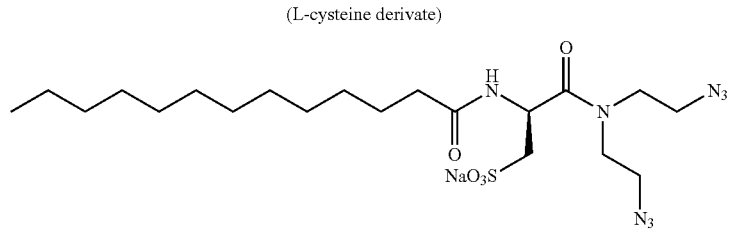
(L-cysteine derivate)
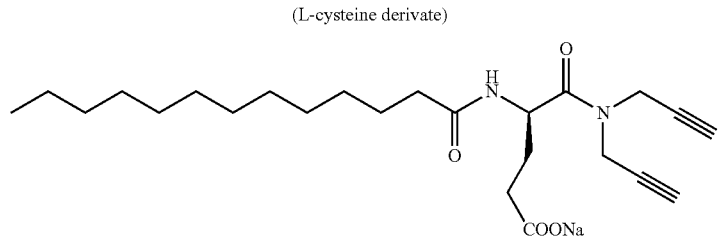
(L-glutamic acid derivate)
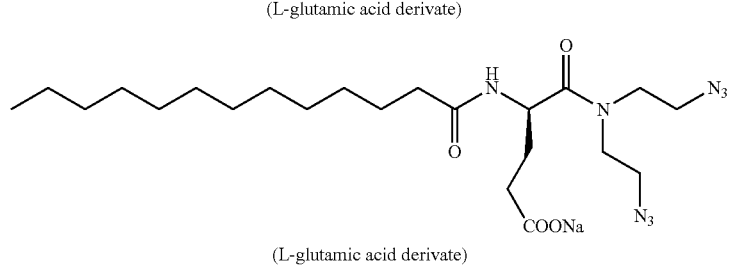
(L-glutamic acid derivate)

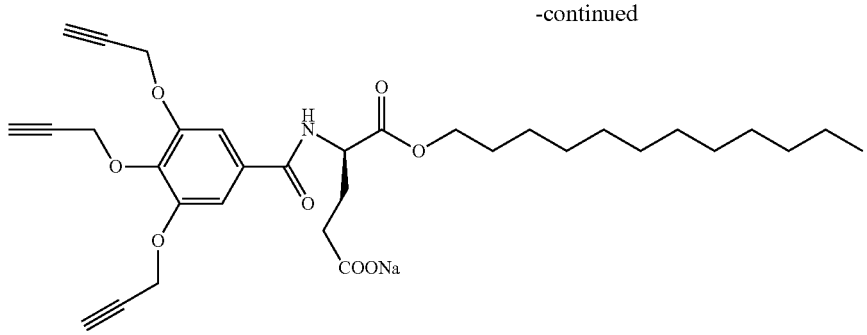
(L-glutamic acid derivative)

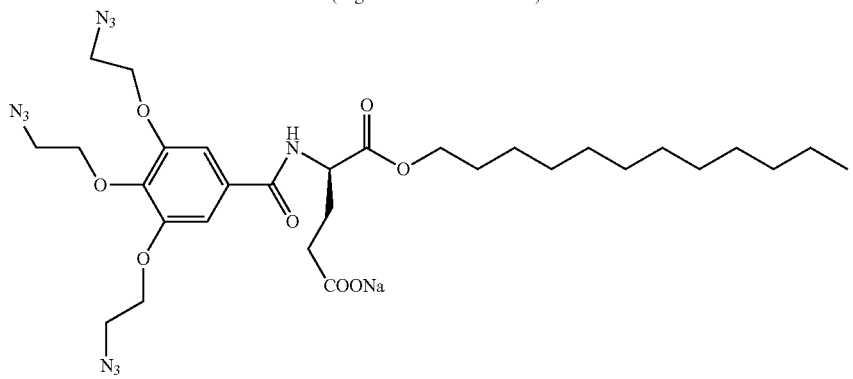
(L-glutamic acid derivative)

Anti-Cancer Formulations

The micelles described herein can be used to encapsulate anticancer drugs, such as camptothecin and doxorubicin. The micelles provide for a controlled release of the drugs under mild acidic conditions. Acid-triggered release is ideal for anticancer drugs because cancerous tissue is more acidic than normal tissue. The size of the drug carrier can be tuned to maximize the accumulation of the drugs at cancerous sites. Active targeting ligands, such as folate groups, can be attached to the surface of the drug carriers to provide improved therapeutic effectiveness.

Pharmaceutical Formulations

The crosslinked micelles or liposomes described herein, for example, those that include an encapsulated drug or diagnostic agent, can be used to prepare therapeutic pharmaceutical compositions. The crosslinked micelles or liposomes can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The crosslinked micelles or liposomes may be systemically administered in combination with a pharmaceutically acceptable vehicle, such as an inert diluent or an assimilable edible carrier. For oral administration, the crosslinked micelle or liposome compositions can be enclosed in hard or soft shell gelatin capsules, compressed into tablets, or incorporated directly into the food of a patient's diet. The crosslinked micelles or liposomes may also be combined with one or more excipients and used in the form of ingestible tablets, buccal tablets, troches, capsules, elixirs, suspensions, syrups, wafers, and the like. Such compositions and preparations typically contain at least 0.1% of active agent. The percentage of the compositions and preparations can vary and may conveniently be from about 2% to about 60% of the weight of a given unit dosage form. The amount of active agent in such therapeutically useful compositions is such that an effective dosage level can be obtained.

The tablets, troches, pills, capsules, and the like may also contain one or more of the following: binders such as gum tragacanth, acacia, corn starch, or gelatin; excipients such as dicalcium phosphate; a disintegrating agent such as corn starch, potato starch, alginic acid and the like; and a lubricant such as magnesium stearate. A sweetening agent such as sucrose, fructose, lactose, or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose, or fructose as a sweetening agent, methyl and propyl parabens as preservatives, a dye, and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

Drug encapsulating micelles or liposomes may be administered intravenously or intraperitoneally by infusion or injection. Solutions of the micelles or liposomes can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the micelles in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of micelles required for use in treatment will vary not only with the particular drug encapsulated but also with the route of administration, the nature of the condition being treated, and the age and condition of the patient, and will be ultimately at the discretion of an attendant physician or clinician.

The micelles or liposomes can be conveniently administered in a unit dosage form, for example, containing 5 to 1000 mg/m$^2$, about 10 to 750 mg/m$^2$, or about 50 to 500 mg/m$^2$ of micelle per unit dosage form. The desired dose may conveniently be presented in a single dose or as divided doses administered at appropriate intervals, for example, as two, three, four, or more sub-doses per day. The sub-dose itself may be further divided, e.g., into a number of discrete loosely spaced administrations.

The invention thus provides therapeutic methods of treating cancer in a mammal, which involve administering to a mammal having cancer an effective amount of a micelle composition described herein. Mammals include primates, humans, rodents, canines, felines, bovines, ovines, equines, swine, caprines, and the like. Cancer refers to any various type of malignant neoplasm, for example, colon cancer, breast cancer, melanoma and leukemia, or other cancerous conditions recited herein, and in general is characterized by an undesirable cellular proliferation, e.g., unregulated growth, lack of differentiation, local tissue invasion, and metastasis.

The ability of a micelle or liposomes described herein to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Surface-crosslinked micelles were prepared as described herein. Post-functionalization, encapsulation, and controlled release studies were carried out, as further described below.

Example 1

Figure 4:
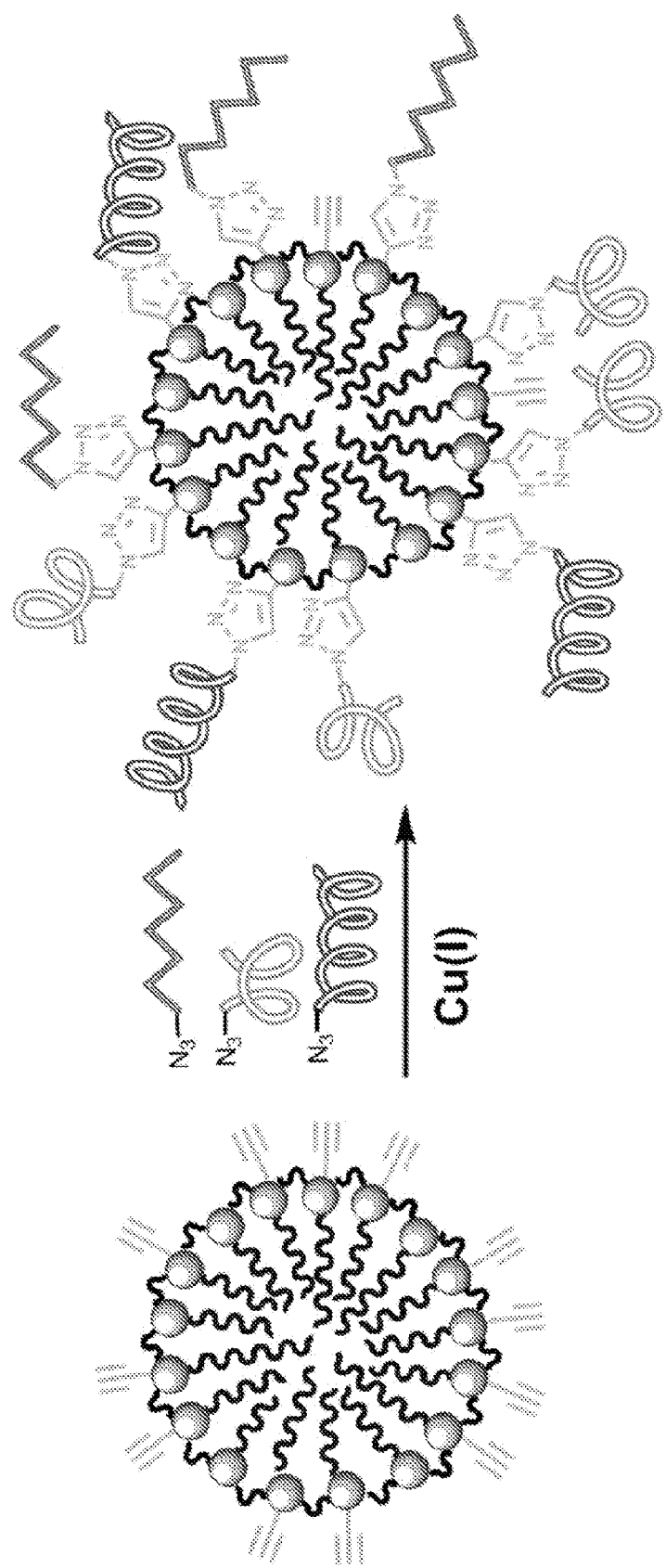
FIG. 4 illustrates post-functionalization of water-soluble nanoparticles, catalyzed by a Cu(I) catalyst in solution, by addition of azide-functionalized polymers or ligands, according to an embodiment. The azide-functionalized polymers or ligands can be, for example, compounds 4, 5, or 6, illustrated in FIG. 1, compounds 12 or 13, illustrated in FIG. 3, or a combination thereof.

Facile Synthesis of Multivalent Water-Soluble Organic Nanoparticles Via "Surface-Clicking" of Alkynylated Surfactant Micelles Crosslinking of alkyne-functionalized surfactants by azido crosslinkers through the highly efficient click reaction afforded surface-crosslinked micelles (SCMs). Post-functionalization of these water-soluble nanoparticles was conveniently catalyzed by the residual Cu(I) catalyst in the solution after addition of azide-functionalized polymers or ligands (FIG. 4). The simplicity of the method, the extremely easy synthesis of the starting materials, and the utility of click reaction, make these materials an excellent platform for synthetic multivalent ligands.

Multivalent interactions occur frequently between biological entities. When strong binding is not possible with a single receptor-ligand pair, multivalency, or simultaneous binding between multiple receptors and ligands, becomes an effective strategy to enhance the binding. Significant efforts have been devoted in recent years to synthetic multivalent ligands and their interactions with biological hosts. Two of the most widely used scaffolds in multivalency are dendrimers and gold nanoparticles protected with functionalized thiols.

An extremely simple method to prepare water-soluble organic nanoparticles as a new platform for multivalent ligands is described herein. The highly efficient "click reaction" (Rostovtsev; Green; Fokin; and Sharpless; *Angew. Chem., Int. Ed.* 2002, 41, 2596-2599; Tornøe et al., *J. Org. Chem.* 2002, 67, 3057-3064) was used to crosslink the surface of alkynylated surfactant micelles. The resulting nanoparticles are completely water-soluble and contain numerous alkynyl groups on the surface, and can be readily decorated with desired ligands. Although crosslinking of surfactant micelles has been reported as early as in the 1970s, the commonly utilized free radical polymerization offers no easy way to functionalize the resulting nanoparticles.

Cationic surfactant 1 was prepared in a few simple steps from commercially available 4-hydroxybenzaldehyde, 1-bromododecane, and tripropargyl amine. With an ammonium head group and a long hydrocarbon tail, it forms micelles above $1.5 \times 10^{-4}$ M in water. The design of the surfactant puts numerous alkynyl groups on the surface of the micelles, which are readily crosslinked by azido derivatives, such as 2a-2c, in the presence of Cu(I) catalyst (FIG. 21). The combination of $CuSO_4$ and sodium ascorbate quickly produced precipitates from a 10 mM micellar solution of 1. Replacement of the $CuSO_4$ with $CuCl_2$, on the other hand, afforded a nearly transparent solution.

Choice of the crosslinker has a significant effect on the resulting micelles. Water-soluble crosslinker 2a readily afforded surface-crosslinked micelles (SCMs) 8-10 nm in diameter, according to dynamic light scattering (DLS). Even though DLS also confirmed the formation of SCMs with 2b, much of this water-insoluble crosslinker remained unconsumed even after prolonged reaction time, presumably because the two reactants were located in different phases. The reaction was typically performed with a 1:1 mixture of 1 and 2a (typically at 1-10 mM in water) with 2.5 mol % of $CuCl_2$ and 25 mol % of sodium ascorbate at room temperature (~23° C.) for 24 hours. Propargyl alcohol was added at the end to terminate the click reaction by consuming residual azido groups left on the SCMs.

Figure 5:
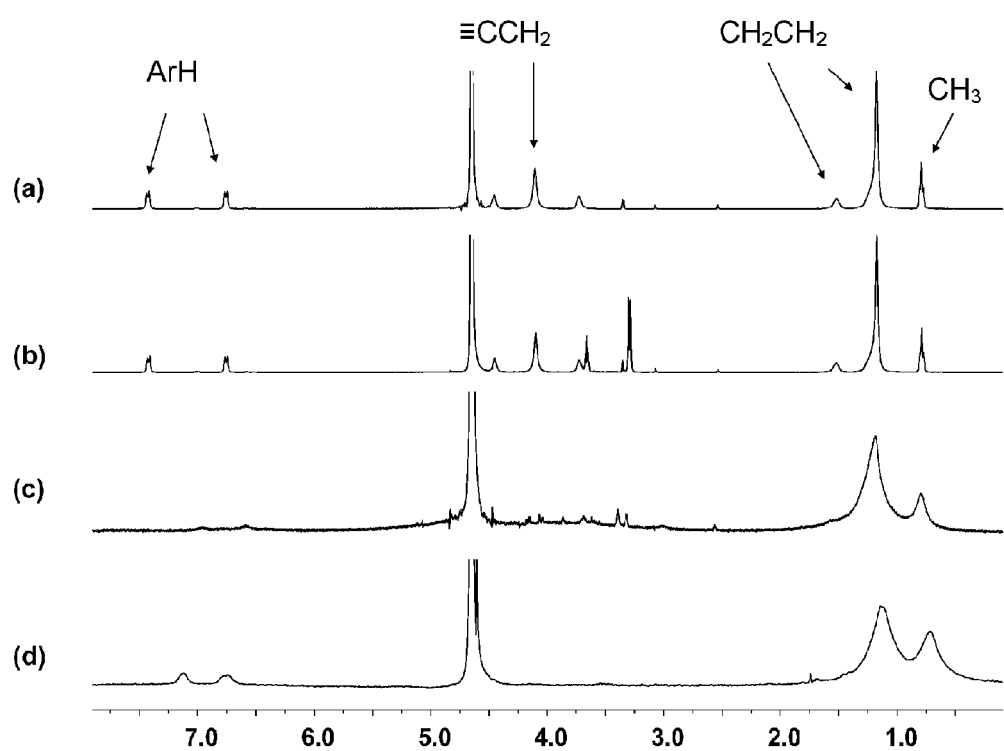
FIG. 5 illustrates $^1$H NMR spectra of a 10 mM micellar solution of 1: (a) in $D_2O$, (b) after addition of 1 equiv of 2a, (c) after crosslinking, and (d) after dialysis to remove water-soluble impurities.

In addition to DLS, formation of SCMs can be monitored by $^1H$ NMR spectroscopy. The proton signals for a 10 mM solution of 1 in $D_2O$ (FIG. 5a) were slightly broader than in $CDCl_3$. The peak broadening is an indication for micellization. Addition of 2a caused no change to the signals of 1 (FIG. 5b), but, after 24 hours in the presence of a Cu(I) catalyst, afforded extremely broad methyl and methylene peaks ($\delta$=1.0-1.3 ppm) of the dodecyl chain and nearly completely suppressed the signals from the protons near the ammonium head group (FIG. 5c). These effects were not caused by the paramagnetic copper, because extensive dialysis of the sample against water removed the impurities and clarified the spectrum near $\delta$=3-4 ppm, however the spectrum looked comparable (FIG. 5d).

Crosslinking thus brought significant changes to the intensity of different protons in the surfactant. In comparison to the proton signals prior to crosslinking (FIG. 5a or 5b), the loss of signal intensity followed the order of terminal $CH_3$<dodecyl $CH_2$<aromatic ArH<benzylic $CH_2$. In other words, the farther the proton is from the crosslinking site, the more its NMR signal was preserved. This result is expected because the ends of the dodecyl chains maintain a fair level of mobility inside the SCM, making them more visible in NMR spectroscopy than those that are restricted by the crosslinking. Note that the aromatic peaks of the SCM shifted upfield slightly, as a result of the proximity of the aromatic groups after crosslinking.

Additional insights on the crosslinking were obtained by cleaving the geminal diol group in the crosslinker. After treatment with an excess of periodic acid, the alkylnyl-SCMs were subjected to ESI-MS analysis. Although many species were detected, the base peak was ammonium cation 3, in line with the 1:1 stoichiometry between 1 and 2a used in the reaction. A smaller amount of 4 was also found, suggesting that, in some of the surfactants, all three triple bonds underwent the cycloaddition.

3

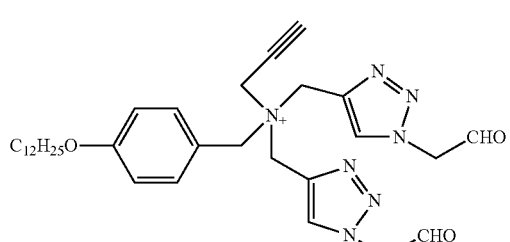

4

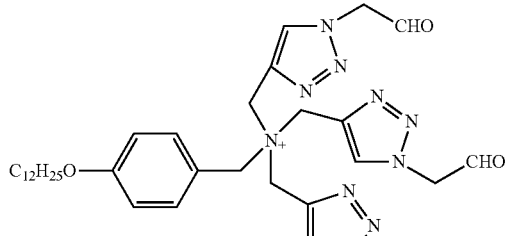

5

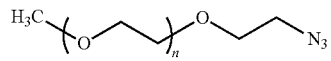

6

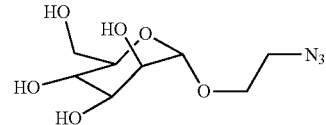

The presence of multiple alkynyl groups on the surface of the SCMs makes it easy to functionalize these nanoparticles. After crosslinking, an azido PEG derivative (5, m.w.=2000) was added directly to the alkynyl-SCM solution. Since both crosslinking and post-functionalization utilize the same click reaction, PEGylation of the SCM could be catalyzed by the residual catalyst in the solution. Additional catalyst (e.g., $CuCl_2$ and/or sodium ascorbate) can optionally be added to increase the speed of the reaction. Termination by propargyl alcohol is unnecessary in the post-functionalization because the surface of the nanoparticles is fully protected by the hydrophilic polymer. After reaction, excess 5 and other impurities were easily removed by dialysis against water. DLS revealed a significant increase in the particle size to about 100 nm in diameter, consistent with the attachment of the PEG chains.

Figure 6:
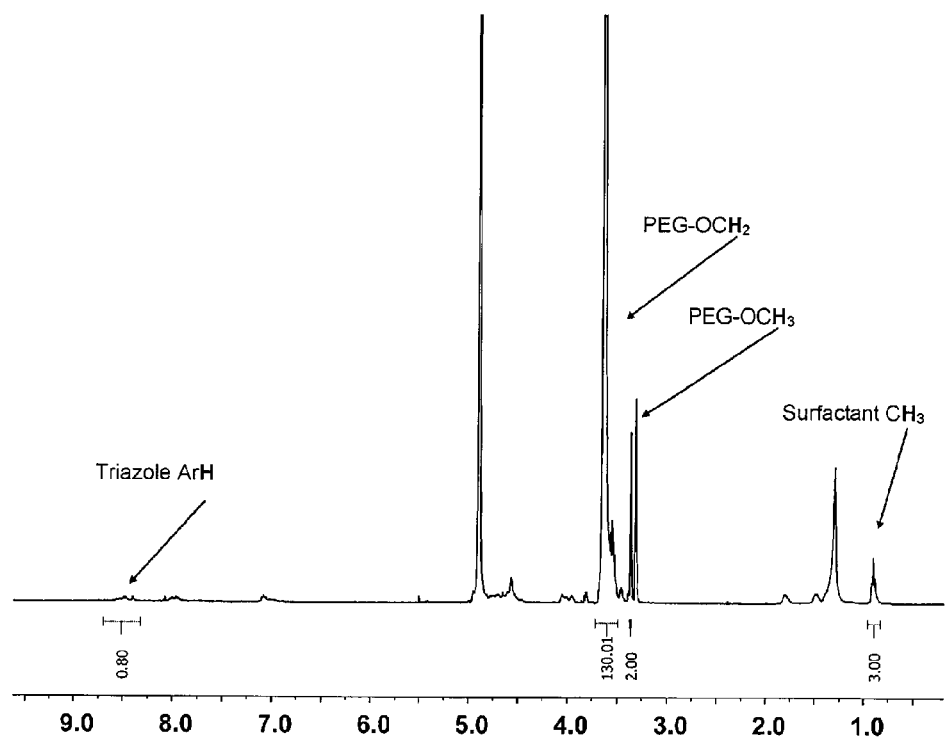
FIG. 6 illustrates a $^1$H NMR spectrum of PEG-SCMs after treatment with an excess of $HIO_4$, overnight at room temperature.

Cleavage of the geminal diol groups enabled a determination of the degree of functionalization in the PEG-SCMs. Integration of the methyl protons from the surfactant and PEG in the cleaved nanoparticles indicated that, on average, one surfactant was functionalized with 0.6-0.8 PEG chains (FIG. 6). The level of functionalization is in line with the number of residual triple bond left on the alkynyl-SCM. If the aggregation number of 1 in the micelle is 50, about 30-40 PEG chains would be present on the surface of a single nanoparticle. Considering the crowded environment that the PEG chains may experience on the surface of an SCM, the level of post-functionalization is quite remarkable. Dodecyltrimethyl ammonium bromide has a micellar aggregation number of 55 in water at 20° C. The aggregation number increases with longer chain length and decreases with larger head group (see Rosen, M. J., *Surfactants and Interfacial Phenomena*, $2^{nd}$ Ed.; Wiley: New York, 1989; p 116).

The SCMs have also been functionalized with a mannose derivative, 6, for its many interesting biological properties. The resulting particles had a hydrodynamic diameter of 25-40 nm, larger than the parent alkynyl-SCMs but smaller than the PEG-SCMs. Periodate-digestion was not performed because the additional geminal diols on the sugar are incompatible with the analysis.

Figure 7:
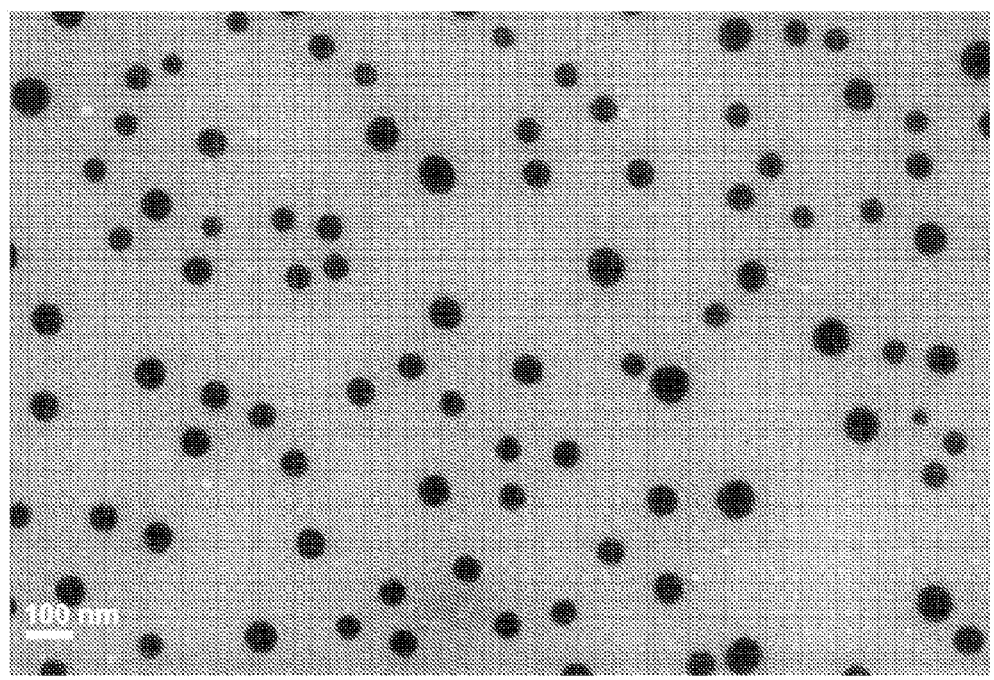
FIG. 7 illustrates a TEM micrograph of PEG-SCMs, stained with 2% phosphotungstic acid aqueous solution.

Transmission microscopy allowed us to visualize the SCMs directly. The samples were stained with 2% phosphotungstic acid. The parent alkynyl-SCMs gave the smallest nanoparticles in the micrograph, averaging about 10 nm in diameter. The mannose-SCMs are larger, with their size mostly ranging from 15-25 nm. The size increase is reasonable with the surface-functionalization. The PEG-SCMs are much larger, showing spherical particles mostly 40-60 nm in diameter and some as large as 80 nm (FIG. 7). Interestingly, the PEG-SCMs are positively stained (i.e., particles appear dark) by phosphotungstic acid whereas the alkynyl- and mannose-SCMs are negatively stained. For the functionalized mannose- and PEG-SCMs, the particle size determined from TEM is smaller than that from DLS. The result is reasonable because DLS measures the hydrodynamic diameter of fully hydrated nanoparticles in solution whereas TEM measures the stained, dry particles in the collapsed state.

mass spectrometer and MALDI-TOF mass was recorded on a Thermobioanalysis Dynamo mass spectrometer. Fourier-Transform Infrared (FTIR) Spectra were recorded on a BRUKER IFS 66V spectrometer. Transmission electron microscopy (TEM) studies were carried out on a PHILIPS CM 30 instrument, operating at 150 kV. The TEM samples were stained with 2% phosphotungstic acid (pH=6.2).

The preparation of compound 1 was carried out by methods analogous to know procedures, as well as by a standard ammonium bromide formation procedure (Scheme 1-2). For example, see Brun et al., *Synthesis* 2002, 1385-1390; Percec et al., *J. Am. Chem. Soc.* 1998, 120, 8619-8631; and Tanabe et al., *Org. Lett.* 2007, 9, 4271-4274.

Scheme 1-2. Synthesis of compound 1

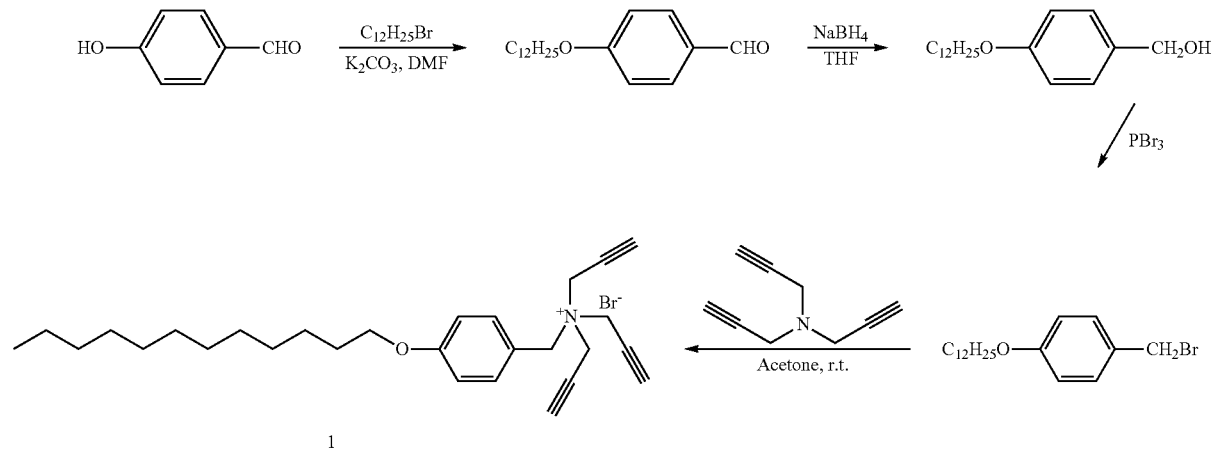

1

Additional functional groups can be added by selecting from various options for the crosslinker. For example, when azido ketone 2c was employed as the crosslinker, the nanoparticles gave both carbonyl (1745 cm$^{-1}$) and triple bond (2111 cm$^{-1}$) stretches in the FT-IR spectroscopy, whereas the particles prepared with 2a only showed the triple bond stretch (2132 cm$^{-1}$).

In conclusion, the creation of a new platform for synthetic multivalent ligands by surface-crosslinking of alkynylated surfactant micelles has been described. The synthesis of the starting materials and the preparation of the nanoparticles are simple. The click chemistry used in both crosslinking and post-functionalization ensures unparalleled functional group compatibility and allows the final functionalized materials to be prepared in a one-pot reaction at room temperature in water. Additional functional groups (e.g., ketones) may be introduced through selection of the corresponding crosslinker, enabling post-modifications orthogonal to the 1,3-dipolar cycloaddition. These features represent significant advantages and cost benefits over other multivalent platforms, such as dendrimers and gold nanoparticles, that typically involve multistep synthesis or expensive metals. The SCMs are useful in both chemical and biological applications. These particles can be used for controlled release and delivery applications.

General Experimental Methods. $^1$H and $^{13}$C NMR spectra were recorded on a BRUKER DRX-400 or on a VARIAN VXR-400 spectrometer. Dynamic light scattering (DLS) was performed on a PD2000DLS$^{PLUS}$ dynamic light scattering detector. ESI-MS was performed on a FINNIGAN TSQ700

4-(Dodecyloxy)benzaldehyde. Potassium carbonate (24.8 g, 180 mmol) was added to a solution of 4-hydroxybenzaldehyde (3.66 g, 30 mmol) in DMF (90 mL) at room temperature. After the mixture was stirred at 60° C. for 1 h, 1-bromooctane (8.7 mL, 36 mmol) was added slowly. The reaction mixture was stirred overnight at 80° C. under N$_2$, cooled to room temperature, and poured over 200 mL of icy water. The mixture was extracted with EtOAc (3×50 mL). The combined organic phase was washed with brine (100 mL), dried over MgSO$_4$, and concentrated in vacuo to give a yellow oil (13.67 g). $^1$H NMR (400 MHz, CDCl$_3$, δ): 9.88 (s, 1H), 7.84 (d, J=8.7 Hz, 2H), 7.00 (d, J=8.7 Hz, 2H), 4.06 (t, J=6.6 Hz, 2H), 1.83-1.76 (m, 2H), 1.62-1.23 (m, 18H), 0.90 (t, J=8.8 Hz, 3H).

4-(Dodecyloxy)benzyl Alcohol. A solution of 4-(dodecyloxy)-benzaldehyde (10 g, 35 mmol) in THF (80 mL) was added dropwise to a stirred suspension of NaBH$_4$ (2.7 g, 70 mmol) in dry THF (70 mL) at 0° C. The reaction mixture was stirred at room temperature overnight and was quenched with a small amount of water (5 mL). The solid formed was removed by filtration and the filtrate was concentrated in vacuo. The residue was dissolved in CHCl$_3$ (50 mL). The resulting solution was washed with brine (3×20 mL), dried over anhydrous Na$_2$SO$_4$, and concentrated in vacuo to give a white powder (9.56 g, 94%). $^1$H NMR (400 MHz, CDCl$_3$, δ): 7.29 (d, J=8.4 Hz, 2H), 6.90 (d, J=8.8 Hz, 2H), 4.62 (d, J=6.0 Hz, 2H), 3.97 (t, J=6.8 Hz, 2H), 1.79-1.51 (m, 2H), 1.51-1.26 (m, 19H), 0.90 (t, J=6.4 Hz, 3H).

4-(Dodecyloxy)benzyl bromide. A solution of PBr$_3$ (2.0 mL, 20 mmol) in anhydrous CH$_2$Cl$_2$ (25 mL) was added slowly to a stirred solution of 4-(dodecyloxy)benzyl alcohol (3.0 g, 10 mmol) in $CH_2Cl_2$ (50 mL) at 0° C. The reaction mixture was stirred for 3 h at room temperature and slowly poured into a large amount of water (ca. 600 mL). The product was extracted with $CHCl_3$ (3×50 mL). The combined organic phase was washed with brine (3×20 mL), dried over anhydrous $Na_2SO_4$, and concentrated in vacuo to give a yellow solid (3.01 g, 90%). $^1$H NMR (300 MHz, $CDCl_3$, δ): 7.32 (d, J=6.6 Hz, 2H), 6.86 (d, J=6.6 Hz, 2H), 4.50 (s, 2H), 3.97 (t, J=6.6 Hz, 2H), 4.05-4.00 (m, 6H), 1.79-1.72 (m, 2H), 1.45-1.21 (m, 12H), 0.90 (t, J=6.3 Hz, 3H).

4-(Dodecyloxy)benzyltripropargylammonium bromide (1). Tripropargylamine (0.85 mL, 9 mmol) in acetone (6 mL) was slowly added to a solution of 4-(dodecyloxy)benzyl bromide (3.01 g, 8.5 mmol) in acetone (10 mL). After 3 d at room temperature, acetone was removed in vacuo and the residue purified by column chromatography over silica gel with $CH_2Cl_2$/MeOH=20/1 to 10/1 as the eluents to give a white powder (2.1 g, 61%). $^1$H NMR (400 MHz, $CDCl_3$, δ): 7.56 (d, J=8.4 Hz, 2H), 7.08 (d, J=8.4 Hz, 2H), 4.62 (s, 2H), 4.32 (s, 6H), 4.22 (s, 3H), 4.02 (t, J=6.4 Hz, 2H), 1.73-1.68 (m, 2H), 1.40-1.24 (m, 18H), 0.87 (t, J=5.6 Hz, 3H); $^{13}$C NMR (100 MHz, $CDCl_3$, δ) 161.6, 134.2, 130.4, 117.2, 115.5, 114.7, 76.6, 75.3, 68.3, 68.0, 63.5, 49.7, 41.9, 29.6, 29.4, 29.3, 29.1, 26, 22.7, 14.1; ESI-MS (m/z): $[M-Br]^+$ calcd for $C_{28}H_{40}NO^+$ 406, found 406.

Crosslinkers 2a-c can be prepare by techniques analogous to those described by Glacon et al. (*Carbohydr. Res.* 2004, 23, 95-110); Haridas et al. (*Org. Lett.* 2008, 10, 1645-1647); and Dave et al. (*Tetrahedron Lett.* 2004, 45, 2159-2162), or as illustrated in Scheme 1-3 below.

Compound 2b. Sodium azide (3.9 g, 60 mmol) was added to a solution of p-xylylene dibromide (4.0 g, 15 mmol) in dry acetone (20 mL). The reaction mixture was heated to reflux under $N_2$ for 12 h. The solid was removed by filtration and the filtrate was concentrated in vacuo to give a yellow oil (2.56 g, 91%). $^1$H NMR (400 MHz, $CDCl_3$, δ): 7.35 (s, 4H), 4.36 (s, 4H).

Compound 2c. Sodium azide (2.60 g, 40.0 mmol) was added to a solution of 1,3-dichloroacetone (1.016 g, 8.0 mmol) in acetone (15 mL). The mixture was stirred at room temperature for 12 h. The solid was removed by filtration and the filtrate was concentrated in vacuo to give a yellow oil (1.075 g, 96%). $^1$H NMR (400 MHz, $CD_3Cl_3$, δ): 4.09 (s, 4H).

Azido PEG compounds can be prepared using techniques analogous to those described by Rivera et al. (*Can. J. Chem.* 2003, 81, 1076-1082) and Parrish et al. (*J. Am. Chem. Soc.* 2005, 127, 7404-7410), or as illustrated below in Scheme 1-4. The value of n in the repeating unit of PEG can be such that the molecular weight of the PEG groups is about 100 to about 10,000.

Scheme 1-4. Synthesis of compound 5

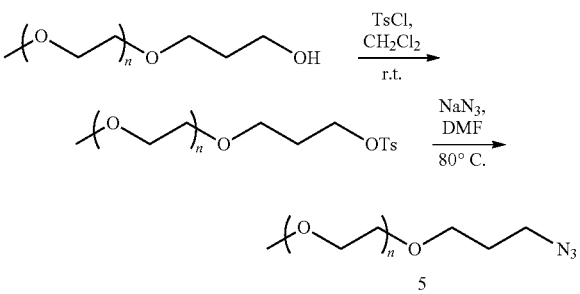

PEG-OTs. Poly(ethylene glycol) monomethyl ether (M.W. 2000, 4.0 g, 2.0 mmol) and p-toluenesulfonyl chloride (0.76 g, 4.0 mmol) were dissolved in dry $CH_2Cl_2$ (20 mL). Pyridine (0.33 mL, 2.0 mmol) was added under $N_2$. The reaction mixture was stirred at 25° C. under $N_2$ for 24 h. After addition of 1 M HCl aqueous solution (10 mL), the mixture was extracted with $CH_2Cl_2$ (3×20 mL). The combined organic phase was dried over $MgSO_4$, filtered, and concentrated in vacuo. The residue was purified by column chromatography over silica gel with $CH_2Cl_2$/MeOH=10/1 as the eluent to give a white solid (4.3 g, 99%). $^1$H NMR (400 MHz, $CD_3Cl_3$, δ): 7.80 (d, J=8 Hz, 2H), 7.35 (d, J=8 Hz, 2H), 3.82-3.45 (m, 172H), 3.37 (s, 3H).

Scheme 1-3. Synthesis of compounds 2a-c

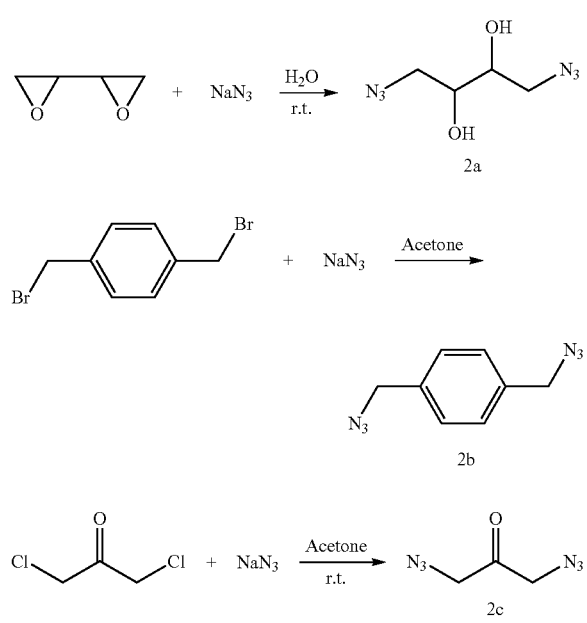

Compound 2a. Sodium azide (2.52 g, 38.7 mmol) was added to a solution of 2,2'-bioxirane (0.5 ml, 6.45 mmol) in water (10 mL). After 12 h at room temperature, the reaction mixture was extracted with ethyl ether (3×50 mL). The combined organic phase was washed with brine (3×20 mL), dried over anhydrous $Na_2SO_4$, and concentrated in vacuo to give a colorless oil (0.75 g, 67%). $^1$H NMR (400 MHz, $D_2O$, δ): 3.69-3.64 (m, 2H), 3.31 (d, J=5.6 Hz, 4H).

Compound 5. Sodium azide (0.39 g, 6.0 mmol) was added to a solution of PEG-OTs (4.3 g, 2.0 mmol) in DMF (40 mL). The reaction mixture was stirred at 80° C. for 12 h, diluted with water (200 mL), and extracted with ethyl ether (3×50 mL). The combined organic phase was washed with water (3×30 mL) and concentrated in vacuo to give a white solid (3.51 g, 86%). $^1$H NMR (400 MHz, $CD_3Cl_3$, δ): 3.82-3.38 (m, 172H); 3.37 (s, 3H).

Modification of saccharides can be carried out by the methods of Watt et al. (*Org. Biomol. Chem.* 2005, 3, 1982-1992); Hayes et al. (*Tetrahedron* 2003, 59, 7983-7996); Rivera et al. (*Can. J. Chem.* 2003, 81, 1076-1082); and Kleinert et al. (*Eur. J. Org. Chem.* 2004, 18, 3931-3940); or as illustrated in Scheme 1-5 below.

Scheme 1-5. Synthesis of compound 6

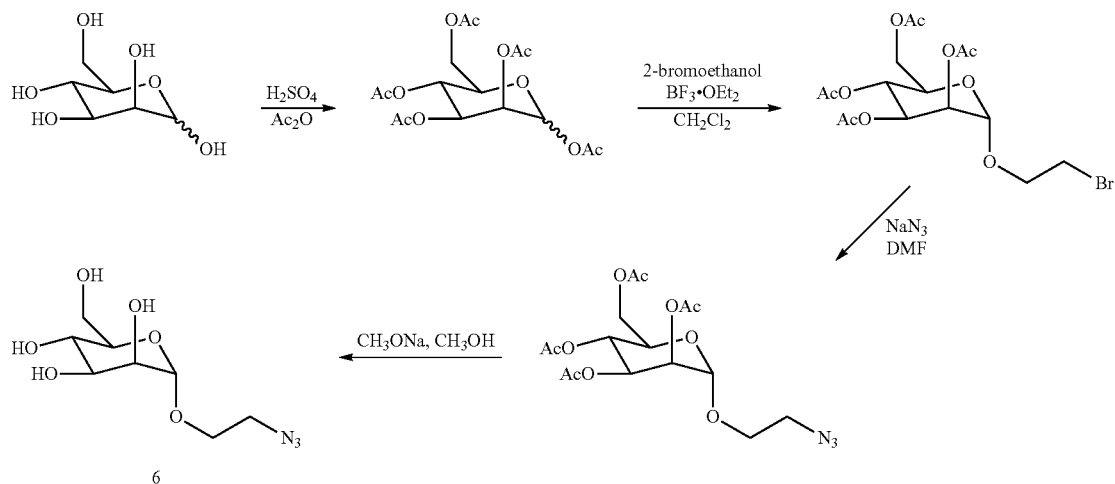

1,2,3,4,6-Penta-O-acetyl-D-mannopyranoside. Sulfuric acid (2 drops) was added to a stirred mixture of D-mannose (4.98 g, 27.8 mmol) and acetic anhydride (27 mL) at 0° C. The reaction mixture was allowed to warm to room temperature after 10 min. After 30 min, the mixture was poured into icy water (100 mL) and extracted with EtOAc (100 mL). The organic layer was washed with water (3×100 mL) and saturated $NaHCO_3$ aqueous solution (3×50 mL), dried over $MgSO_4$, and concentrated in vacuo to give a yellow oil (10.0 g, 93%). The product was used in the next step without further purification.

2'-Bromoethyl 2,3,4,6-tetra-O-acetyl-α-D-mannopyranoside. Boron trifluoride etherate (5.1 ml, 40.0 mmol) was added to a solution of 1,2,3,4,6-penta-Oacetyl-D-mannopyranoside (3.9 g, 10.0 mmol) and 2-bromoethanol (0.82 ml, 11.0 mmol) in dry $CH_2Cl_2$ (40 mL). The reaction mixture was stirred in dark under $N_2$ for 3 h, diluted with $CH_2Cl_2$ (50 mL), and quenched by saturated $NaHCO_3$ aqueous solution (100 mL). The organic phase was washed with water (3×50 mL), dried over $MgSO_4$, and concentrated in vacuo. The residue was purified by column chromatography over silica gel with ethyl acetate/hexane=2/1 as the eluent to give a white powder (1.81 g, 40%). $^1H$ NMR (400 MHz, $CD_3Cl_3$, δ): 5.33-5.26 (m, 3H), 4.87 (1H, s), 4.29-4.25 (m, 1H), 4.15-4.11 (m, 2H), 3.99-3.95 (m, 1H), 3.90-3.86 (m, 1H), 3.53 (t, J=8 Hz, 2H), 2.16 (s, 3H), 2.11 (s, 3H), 2.05 (s, 3H), 2.00 (s, 3H).

2'-Azidoethyl-2,3,4,6-tetra-O-acetyl-α-D-mannopyranoside. Sodium azide (1.625 g, 25 mmol) was added to a solution of 2'-bromoethyl 2,3,4,6-tetra-O-acetyl-α-D-mannopyranoside (1.81 g, 4.0 mmol) in anhydrous DMF (10 mL). The reaction mixture was stirred at 60° C. overnight. DMF was removed by rotary evaporation and the residue was dissolved in $CH_2Cl_2$ (100 mL). The $CH_2Cl_2$ solution was washed with water (4×50 mL), dried over $MgSO_4$, filtered, and concentrated in vacuo to give a white powder (1.72 g, 94%). $^1H$ NMR (400 MHz, $CD_3Cl_3$, δ): 5.37-5.27 (m, 3H), 4.87 (s, 1H), 4.30-4.27 (m, 1H), 4.14-4.10 (m, 1H), 4.01-4.03 (m, 1H), 3.90-3.84 (m, 1H), 3.69-3.64 (m, 1H), 3.52-3.41 (m, 2H), 2.16 (s, 3H), 2.11 (s, 3H), 2.05 (s, 3H), 2.00 (s, 3H).

Compound 6. Sodium methoxide (0.1 N, 0.82 mL, 0.082 mmol) in methanol was added to a solution of 2'-azidoethyl 2,3,4,6 tetra-O-acetyl-α-D-mannopyranoside (1.72 g, 4.1 mmol) in dry methanol (20 mL). After 2 h at room temperature, acidic ion-exchange resin (Dowex 50wx8-200) was added until pH=6-7. The resin was removed by filtration and the filtrate was concentrated in vacuo to give a white powder (1.0 g, 98%). $^1H$ NMR (400 MHz, $D_2O$, δ): 4.91 (d, J=1.6 Hz, 1H), 3.98-3.97 (m, 1H), 3.93-3.88 (m, 2H), 3.88-3.82 (m, 1H), 3.78-3.65 (m, 4H), 3.54-3.48 (m, 2H).

Preparation of alkynyl-SCMs. Compound 2a (3.45 mg, 0.02 mmol), $CuCl_2$ (10 µL of 6.7 mg/mL aqueous solution, 0.5 mmol), and sodium ascorbate (10 µL of 99 mg/mL aqueous solution, 5 µmol) were added to a micellar solution of 1 (10 9.73 mg, 0.02 mmol) in millipore water (2.0 mL). The reaction mixture was stirred slowly at room temperature for 24 h before propargyl alcohol (0.6 µL) was added. After another 12 h, the mixture was dialyzed against deionized water using a 500 Da molecular weight cut-off tubing.

Preparation of PEG-SCMs. Alkynyl-SCMs were prepared as above. After crosslinking, (without the addition of propargyl alcohol) 5 (81.0 mg, 0.04 mmol), $CuCl_2$ (10 µL of 6.7 mg/mL aqueous solution, 0.5 mmol), and sodium ascorbate (10 µL of 99 mg/mL aqueous solution, 5 mmol) were added. After another 12 h at room temperature, the mixture was dialyzed against deionized water using a 6-8 kDa molecular weight cut-off tubing.

Preparation of mannose-SCMs. Alkynyl-SCMs were prepared as above. After crosslinking, (without the addition of propargyl alcohol), 6 (15 mg, 0.06 mmol), $CuCl_2$ (10 µL of 6.7 mg/mL aqueous solution, 0.5 mmol), and sodium ascorbate (10 µL of 99 mg/mL aqueous solution, 5 µmol) were added. After another 12 h at room temperature, the mixture was dialyzed against deionized water using a 500 Da molecular weight cut-off tubing.

Synthesis of Alkynyl-Keto SCMs. Compound 2c (2.8 mg, 0.02 mmol), $CuCl_2$ (10 µL of 6.7 mg/mL aqueous solution, 0.5 µmol), and sodium ascorbate (10 µL of 99 mg/mL aqueous solution, 5 µmol) were added to a micellar solution of 1 (9.73 mg, 0.02 mmol) in millipore water (2.0 mL). The reaction mixture was stirred slowly at room temperature for 24 h before propargyl alcohol (0.6 µL) was added. After another 12 h, the mixture was dialyzed against deionized water using a 500 Da molecular weight cut-off tubing.

Example 2

Facile Preparation of Organic Nanoparticles by Interfacial Crosslinking of Reversed Micelles and Templated Synthesis of Sub-Nanometer Au—Pt Nanoparticles Surfactants can self-assemble into a rich array of ordered phases depending on their molecular structures, temperature, and amounts of polar, nonpolar, and surfactant ingredients. There has been a long-standing interest in capturing these noncovalently stabilized phases by covalent bonds to prepare ordered nanomaterials. Covalent fixing of these self-assembled phases not only enhances their stability but also enables them to be used as templates for further material synthesis.

Reversed micelles (RMs) are formed when a small amount of water is added to a mixture of a suitable surfactant in nonpolar solvent(s). RMs are widely employed as media for catalysis and templates to prepare inorganic nanomaterials. Nevertheless, the dimension of the inorganic materials obtained from the templated synthesis rarely correlates with the size of the RM templates. Collisions of these dynamic assemblies result in coalescence as well as rapid exchange of the entrapped water and dissolved contents, making it difficult to predict the size and morphology of the final materials. Although covalent fixing of the RMs might be expected to circumvent these problems, it is exactly the same problems one has to face when attempting to capture RMs of the original size. Earlier attempts to polymerize RMs produced objects much larger than the original assemblies. Recently, McQuade and co-workers reported the first example of capturing RMs by free radical polymerization (*J. Am. Chem. Soc.* 2003, 125, 5351-5355). A key to their success was the design of an AOT-like surfactant with two polymerizable groups near the head group.

This Example provides a method to use highly efficient thiol-ene "click" reactions to crosslink RMs exclusively at the interface. The synthesis of the starting materials and the crosslinking can be readily carried out using standard synthetic techniques. These interfacially crosslinked reversed micelles (ICRMs) can be used to template the synthesis of both small (3-4 nm) and ultrasmall (<1 nm) metal nanoparticles. Size control is controllable, based on the amounts of the metal precursor versus surfactant employed in the synthesis. Nanoalloys are obtained by simply combining two metal precursors in the same reaction. These features are the direct results of the covalent nature of the templates, which are difficult to obtain from conventional RMs.

Figure 8:
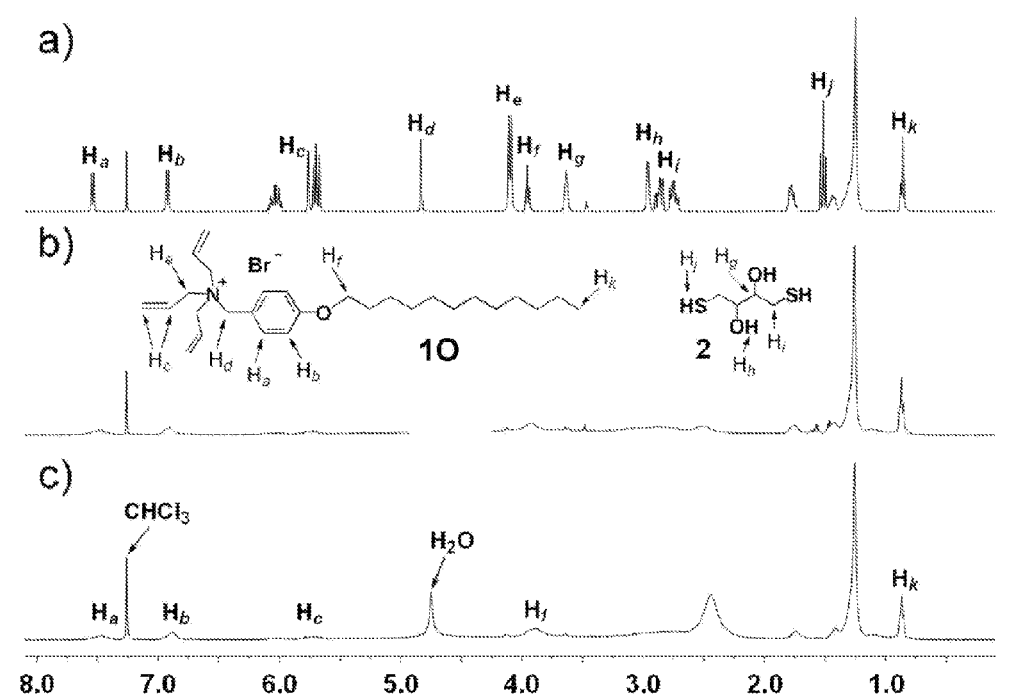
FIG. 8 illustrates $^1$H NMR spectra of a 2:3 mixture of 10 and 2 of Example 2: (a) before irradiation, (b) after UV irradiation for 10 hours, and (c) after washing with water.

Quaternary ammonium surfactant 10 (4-(dodecyloxy)benzyl-triallylammonium bromide) was prepared by alkylation of 4-hydroxy-benzaldehyde with 1-bromododecane, reduction of the aldehyde with sodium borohydride, bromination of the resulting alcohol with phosphorus tribromide, and nucleophilic displacement of the bromide with triallyl amine. Optically clear RM solutions were obtained in a 2:1 heptane/chloroform mixture with $W_0$<15 ($W_0$=[$H_2O$]/[1]). In FIG. 8, dithiol crosslinker 9 is crosslinker 2. Although RMs could form without chloroform, this solvent aided the dissolution of dithiol crosslinker 2 in the nonpolar mixture.

Crosslinking of the RMs was achieved by UV-irradiation of the solution ($W_0$=5) in the presence of 2,2'-dimethoxy-2-phenylacetophenone, a photoinitiator. After crosslinking, the sharp peaks in the $^1$H NMR spectrum of a 2:1 mixture of 10 and 2 (FIG. 8*a*) became broad and the alkenic protons ($H_c$) of 10 and those on the crosslinker disappeared almost completely (FIG. 8*b*). After evaporation of solvents and washing with water, the materials obtained were soluble in common organic solvents such as chloroform, tetrahydrofuran, and acetone, but insoluble in water and methanol. Notably, the methyl and methylene protons of the dodecyl chain were sharp and well-resolved, whereas the protons near the ammonium head group were broad and weak or absent (FIG. 8*c*). These results are consistent with crosslinking at the interface in the RM configuration, which constrains the movement of the ammonium head group but not that of the hydrocarbon tail pointing outward.

Figure 9A:
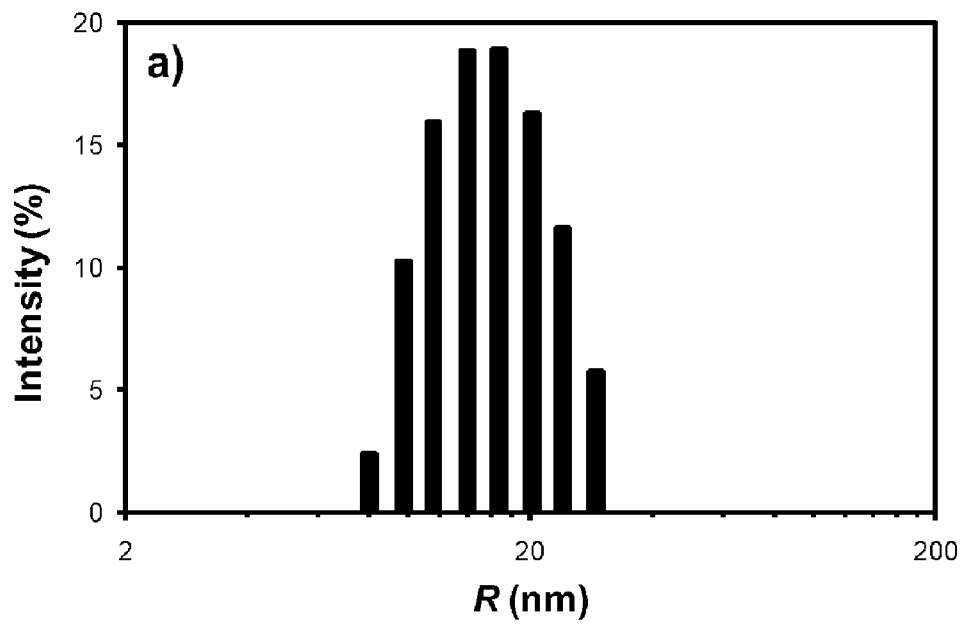
FIG. 9 illustrates the hydrodynamic radii of aggregates of CRMs determined by DLS in (a) acetone at 0 min, (b) acetone at 40 min, (c) butanone, (d) chloroform, and (e) THF before mass-normalization and (f) THF after mass-normalization.
Figure 9B:
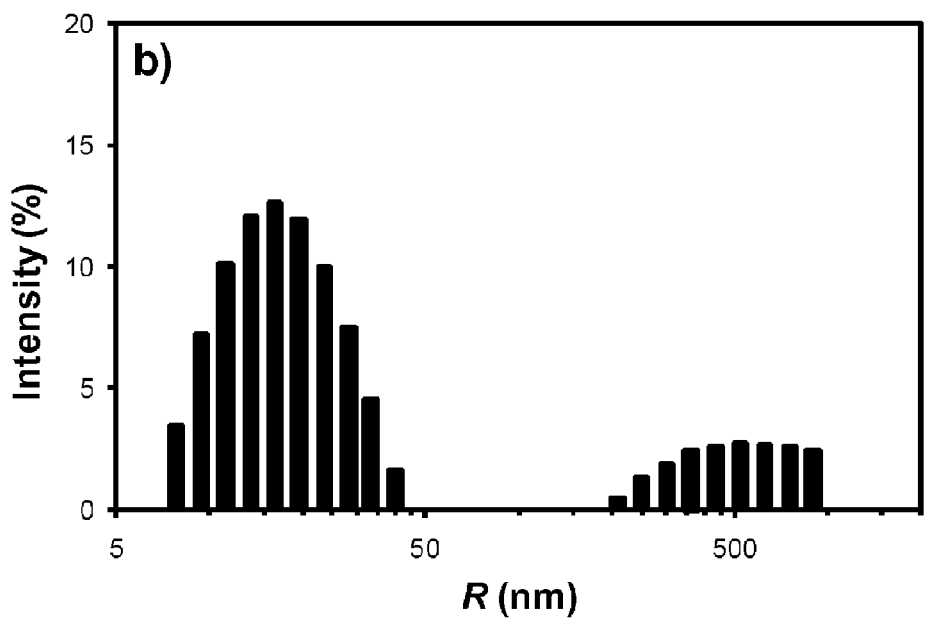

The CRMs were additionally characterized by dynamic light scattering (DLS) and transmission electron microscopy (TEM). Although the CRMs were soluble in many organic solvents (e.g., chloroform, methylene chloride, THF, acetone, butanone, DMF, DMSO), their sizes determined by DLS were quite different. TABLE 1 summarizes the hydrodynamic diameters of the RMs and ICRMs determined in various solvents. The RMs were captured in 2:1 heptane/$CHCl_3$. Instead of trying to obtain the refractive index and viscosity for the mixed solvent, the diameter of the RMs was calculated using the parameters of heptane (entry 1) and $CHCl_3$ (entry 2), respectively. The sizes (5-6 nm) obtained were indeed very close and compared favorably with those of conventional AOT RMs (2-3 nm), considering the (longer) dodecyl tail of 1 and the extra phenylene spacer. FIG. 9 shows the size-distribution of these nanoparticles in several organic solvents. The average hydrodynamic radius was 16 nm in both acetone (FIG. 9*a*) and butanone (FIG. 9*c*) for freshly made samples. Over time (about 1-2 hours), however, the scattered light intensity increased significantly for the acetone sample and large particles, hundreds of nanometers in radius, started to form (FIG. 9*b*, data collected at 40 minutes).

TABLE 1

Hydrodynamic Diameters of RMs and ICRMs Determined by DLS[a]

| Sample | Solvent | Diameter (nm) |
|---|---|---|
| RMs of Compound 1 | 2:1 heptane/$CHCl_3$ | 6[b] |
| RMs of Compound 1 | 2:1 heptane/$CHCl_3$ | 5[c] |
| ICRMs of Compound 1 | $CHCl_3$ | 190 |
| ICRMs of Compound 1 | THF | 13 |
| RMs of Compound 2 | 2:1 heptane/$CHCl_3$ | 5[b] |
| RMs of Compound 2 | 2:1 heptane/$CHCl_3$ | 4[c] |
| ICRMs of Compound 2 | $CHCl_3$ | 5 |
| ICRMs of Compound 2 | THF | 4 |

[a]The diameters were averages of five measurements. Each measurement was based on 20 accumulations of data collection. The relative standard deviations within the five measurements ranged from 1 to 9%.
[b]The diameter was calculated using the viscosity and refreactive index of heptane.
[c]The diameter was calculated using the viscosity and refractive index of $CHCl_3$.

Figure 9C:
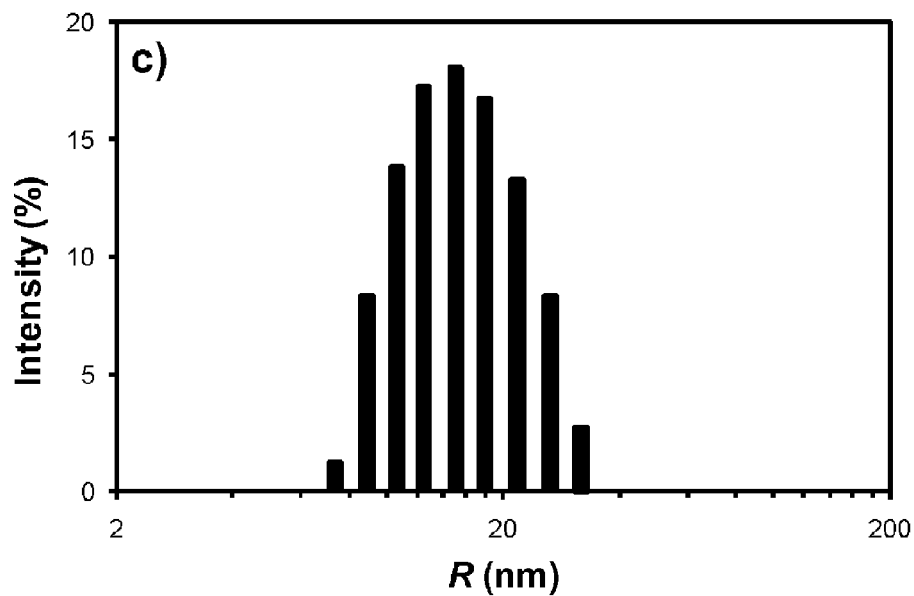
Figure 9D:
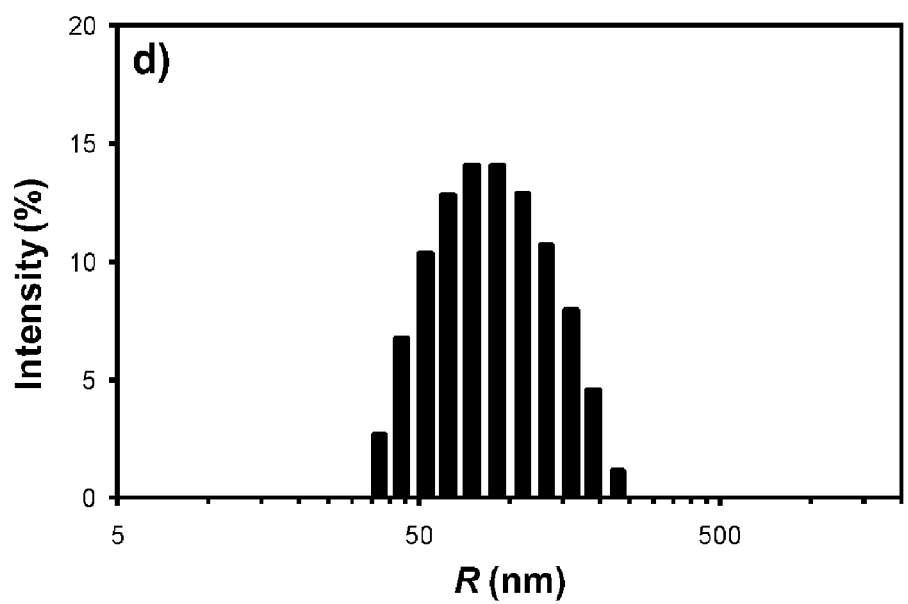
Figure 9E:
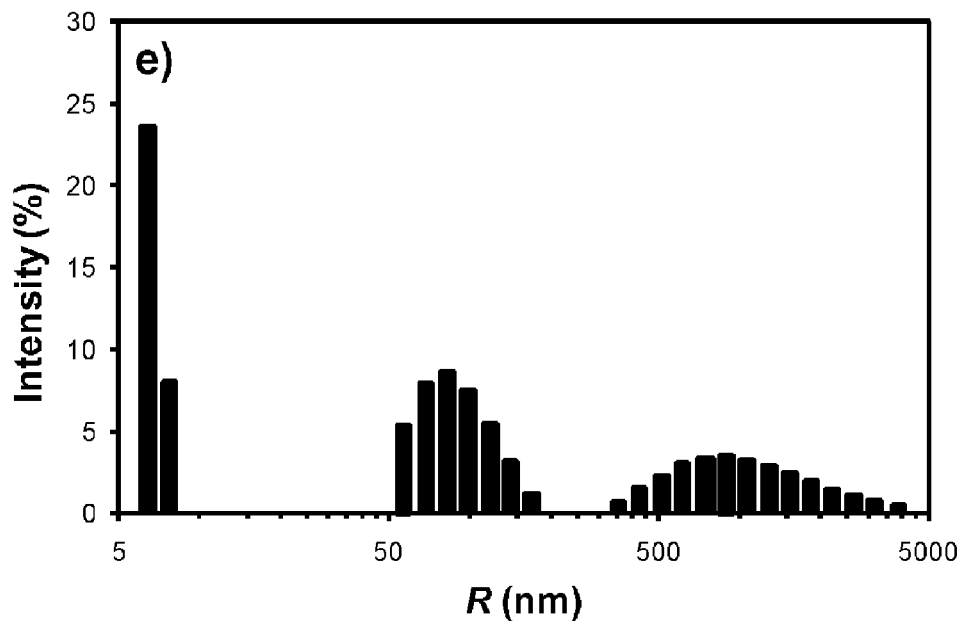
Figure 9F:
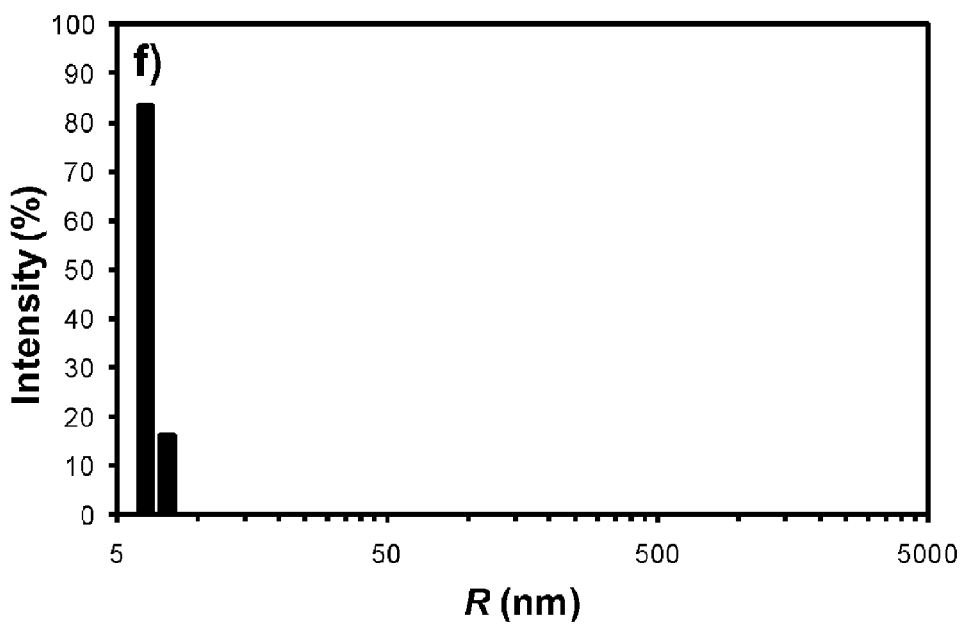

These large particles eventually became insoluble in acetone and precipitated out of the solution, at which time the scattered light intensity became extremely low (data not shown). These changes can be attributed to particle aggregation in the relatively polar acetone because the size stayed constant (about 16-20 nm) in the less polar butanone indefinitely (FIG. 9*c*). The size was different again in chloroform, about 95 nm in radius, and stayed unchanged over time (FIG. 9*d*). The particles were smallest in THF, only about 7 nm in radius, although some very large particle existed (FIG. 9*e*). Because large particles scatter light substantially more than small particles, the small particles were actually the dominant species, as shown by the mass-normalized size distribution (FIG. 9*f*).

Figure 10A:
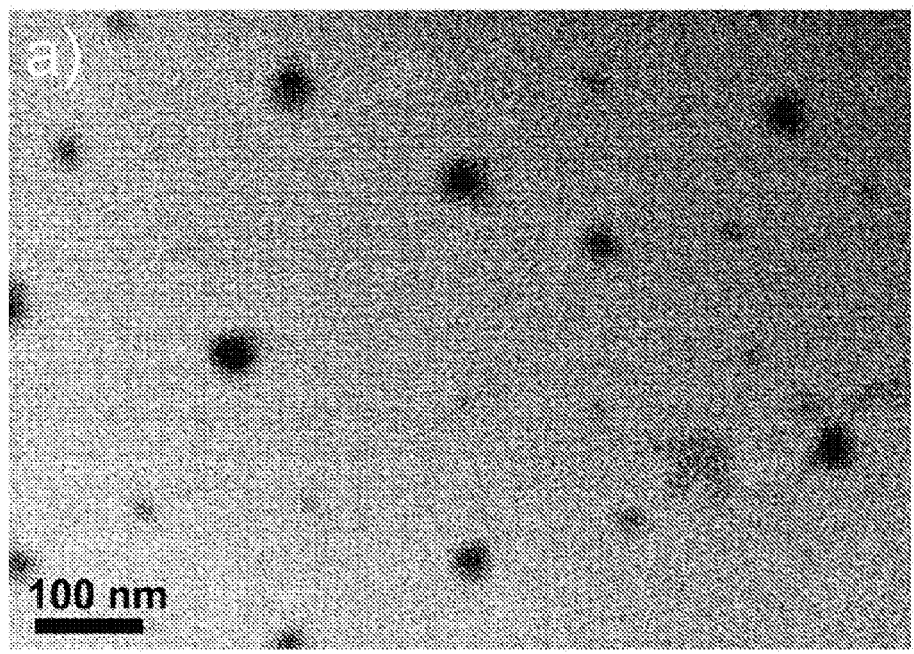
FIG. 10 illustrates TEM micrographs of (a) unstained CRMs and (b) CRMs stained with 2% phosphotungstic acid.
Figure 10B:
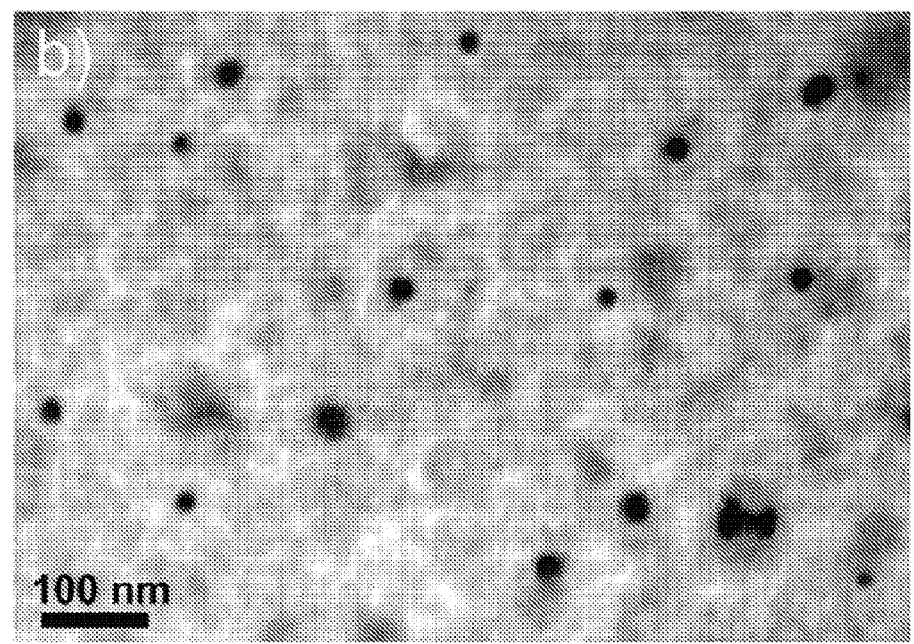

Because it appeared that aggregation could be significant in some solvents, TEM was used for further characterization of the CRMs. Transmission microscopy (TEM) allowed for visualization of the CRMs directly. Both small particles (R≈10 nm) and large particles (R=15-20 nm) could be found in a sample prepared from THF (FIG. 10a). These sizes were quite consistent with those obtained by DLS. It is possible that the large particles were simply aggregates of the small particles, as suggested by the DLS study. Alternatively, the large particles could result from coalescence of small particles during crosslinking and thus could be permanent. To further confirm the covalent capture, phosphotungstic acid-stained CRMs were examined, which displayed improved contrast under TEM (FIG. 10b). The TEM images showed many spherical particles 10-15 nm in radius. Interestingly, some larger particles, e.g., the one at upper right corner and the one near the lower right corner, were observed to form by aggregation.

With the introverted ammonium groups at the core, the ICRMs can extract anionic metal precursors, such as tetrachloroaurate ($AuCl_4^-$), from water to chloroform. Addition of sodium borohydride to the chloroform solution immediately turned its color from light yellow to purple. The choice of the crosslinker was important to the RM capture. Although organic-soluble materials could be obtained when a hydrophobic crosslinker such as 1,4-butanedithiol was used in the photocrosslinking, the materials were unsuitable for the templated synthesis and only bulk gold precipitate formed following the same procedures.

Figure 11:
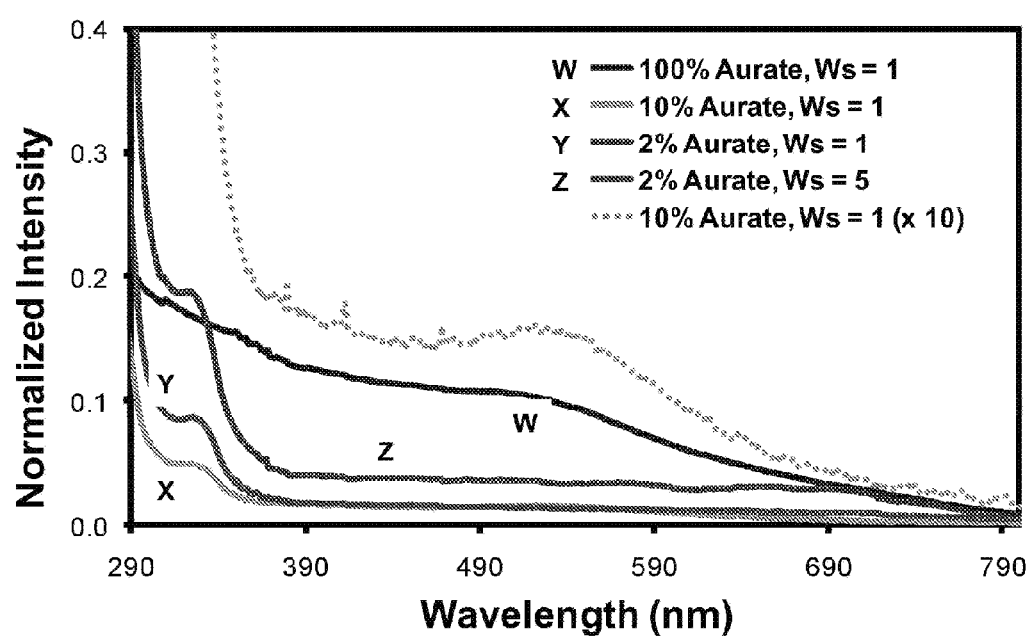
FIG. 11 illustrates UV-vis spectra of Au-CRMs prepared with $[AuCl_4^-]/[10]=1$ (line W), 0.1 (line X), and 0.02 (line Y), according to the procedures described in Example 2. The dotted spectral line is that of $[AuCl_4^-]/[10]=0.1$ multiplied by 10. $[10]=5\times10^{-4}$ M.

When equivalent amounts of aurate and surfactant 10 were used (i.e., $[AuCl_4^-]/[10]=1$), the UV-vis spectrum showed broad absorption with a peak at 520 nm (FIG. 11), indicating the formation of gold nanoparticles >2 nm in diameter. The solution was stable indefinitely in our hands, showing no signs of precipitation and/or aggregation. The surface plasmon absorption band at 520 nm became significantly weaker and a higher-energy peak appeared at about 330 nm when the $[AuCl_4^-]/[10]$ was reduced to 0.1, indicating formation of both large (>2 nm) and ultrasmall (<1 nm) nanoparticles under this condition. The amount of ultrasmall nanoparticles increased even more as the $[AuCl_4^-]/[10]$ ratio was reduced to 0.02. The absorption at 330 nm became stronger and that at 520 disappeared completely. These data indicate that the size of the gold nanoparticles was controlled by the amount of aurate used in the templated synthesis. Different amounts of water ($W_0=1$ or 5), for example, caused very little difference in the position of the absorption (FIG. 11).

TEM analysis gave results consistent with those from the UV-vis spectroscopy analysis. The particles obtained at $[AuCl_4^-]/[10]=1$ averaged about 3 nm. Similar sized nanoparticles were also observed at $[AuCl_4^-]/[10]=0.1$, but far fewer particles appeared in the micrograph even though the concentration of the sample was higher than what was used for $[AuCl_4^-]/[10]=1$. Presumably, subnanometer gold particles existed in sample at $[AuCl_4^-]/[10]=0.1$, but were undetectable by TEM. This trend continued as $[AuCl_4^-]/[10]$ was reduced to 0.02. Even fewer particles were observable in TEM and what could be seen were very small (1 nm or less).

Subnanometer gold and silver clusters have attracted interest in recent years as novel biolabels and optoelectronic emitters. As their size approaches the Fermi wavelength of electrons, noble metal clusters display dramatically different optical, electronic, and chemical properties, from either the bulk or the nanoscale metals. The photoluminescence of these materials agreed completely with the UV-vis and TEM data. Under a hand-held UV lamp (365 nm), the Au-ICRMs prepared with $[AuCl_4^-]/[10]=1$ gave no signs of luminescence. As the $[AuCl_4^-]/[10]$ ratio decreased, the sample became increasingly fluorescent, with the sample prepared with the lowest aurate giving the brightest blue light.

A unique property of subnanometer gold clusters is their atom-like properties. Indeed, the excitation/emission spectra of these Au-CRMs resembled those of molecular fluorophores, displaying the maximum at 315/354 nm. The electronic transition energy of Au clusters is known to scale with inverse cluster radius. The excitation/emission wavelengths for $Au_3$, $Au_4$, $Au_5$ clusters, for example, were reported to be 305/340, 313/371, and 330/385 nm, respectively. Comparison with the literature data suggests that the dominant fluorescent species in our Au-ICRMs is most likely $Au_4$ clusters, a reasonable result based on the $[AuCl_4^-]/[1]$ ratio of 0.02 and typical aggregation number of RMs.

Figure 12:
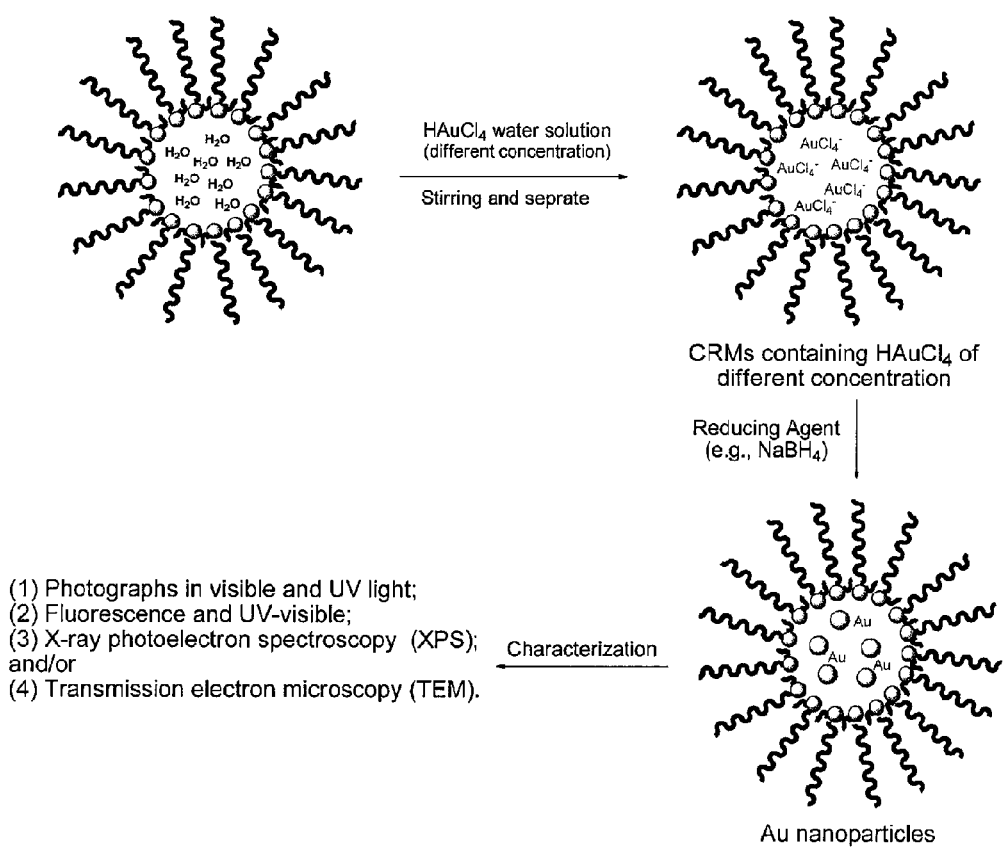
FIGS. 12 and 13 illustrate the templated synthesis of metal nanoparticles, according to various embodiments, including first extracting $AuCl_4^-$ (FIG. 12) or the mixture of $AuCl_4^-$ and $PtCl_6^{2-}$ (FIG. 13) into organic solvents, followed by reduction (e.g., with $NaBH_4$ or other reducing agents); the gold nanoparticles or Au—Pt alloy may be fluorescent, and can be characterized by DLS, fluorescence, or TEM.
Figure 13:
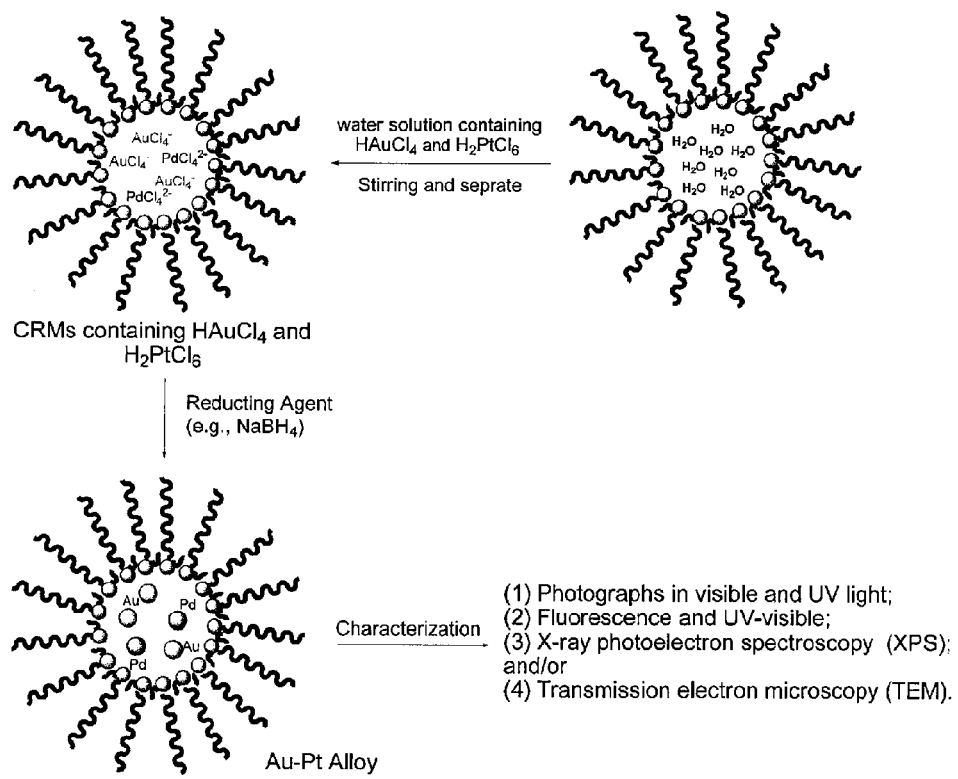

Thus, nanoalloys such as Au—Pt, were readily prepared via the templated synthesis described herein. Using $PtCl_6^{2-}$ or a 1:1 mixture of $AuCl_4^-$ and $PtCl_6^{2-}$ with 2 mol % of the total metal precursor, fluorescent Pt and Au—Pt clusters were obtained following similar procedures (FIGS. 12 and 13). The excitation/emission wavelengths of the Pt clusters were 346/399 nm. Interestingly, the Au—Pt clusters displayed an intermediate values (329/390 nm). The few metal atoms appeared to indeed exist as alloys instead of separate clusters.

In summary, a simple method to crosslink RMs at the interface using the highly efficient thiol-ene click reaction has been described. The method allowed covalent fixing of the dynamic surfactant assemblies and produced stable organic nanoparticles soluble in common solvents. These crosslinked RMs can be used to produce both nanometer and subnanometer metal particles by varying the ratio of metal precursor/surfactant used in the synthesis. Although dendrimers can also be suitable templates for subnanometer gold clusters, such reaction often take several days to complete, and post-purification (e.g., centrifugation) is needed to remove large particles formed during the synthesis. The straightforward synthesis of 10, the simplicity of the templated synthesis, and the many applications of the noble metal clusters in photonics and catalysis make the ICRMs highly attractive templates in advanced nanomaterials synthesis.

Experimental Details.

Synthesis of 10: Triallylamine (0.70 mL, 4.0 mmol) in acetone (2 mL) was slowly added to a solution of 4-(dodecyloxy)benzyl bromide (0.71 g, 2.0 mmol) in acetone (3 mL). After 3 d at room temperature, acetone was removed by rotary evaporation and the residue purified by column chromatography over silica gel with $CH_2Cl_2/MeOH=20/1$ to 10/1 as the eluents to give a white powder (0.63 g, 64%). $^1H$ NMR (400 MHz, $CDCl_3$, δ): 7.58 (d, J=8.4 Hz, 2H), 6.95 (d, J=8.8 Hz, 2H), 6.04-5.96 (m, 3H), 5.78-5.30 (m, 6H), 4.91 (s, 2H), 4.18 (d, J=7.2 Hz, 6H), 3.98 (t, J=6.4 Hz, 2H), 1.81-1.75 (m, 2H), 1.45-1.26 (m, 18H), 0.89 (t, J=6.8 Hz, 3H); $^{13}C$ NMR (100 MHz, $CDCl_3$, δ) 160.74, 134.34, 128.31, 125.06, 118.64, 114.95, 68.07, 63.58, 61.49, 31.74, 29.50, 29.47, 29.44, 29.41, 29.25, 29.18, 29.0, 25.87, 22.52, 22.27, 13.98; ESI-MS (m/z): $[M-Br]^+$ calcd for $C_{28}H_{46}NO^+$ 412. found 412.

Preparation of CRMs: Water (1.8 μL) was added to a solution of 10 (9.8 mg, 0.02 mmol) in heptane (1.0 ml) and $CHCl_3$ (0.5 ml). The mixture was hand shaken and sonicated at room temperature for 1 min to give an optically clear solution. After addition of 2 (4.6 mg, 0.03 mmol) and 2,2'-dimethoxy-2-phenylacetophenone (25.6 mg/mL in chloroform, 10 μL, 0.1 mmol), the mixture was irradiated in a Rayonet photoreactor for ca. 10 h until most alkenic protons in 10 were consumed. The organic solvents were removed by rotary evaporation and the residue was washed by water to give a white power (11.2 mg).

Preparation of Au-CRMs: A 5 mM aqueous solution of HAuCl$_4$ (2 mL) was added to a 10 mM RCM solution in chloroform (2 mL). The aqueous phase became colorless and the organic phase turned yellow upon stirring. A freshly prepared aqueous solution of sodium borohydride (0.2 M, 1 mL) was slowly to the vigorously stirred reaction mixture. The organic phase turned purple immediately and the color intensified over 2 h. The organic phase was washed with water three times and concentrated by rotary evaporation. The residue could be redissolved in common organic solvents and were stable over a period of several months.

Example 3

Reversible Crosslinkers

The SCMs and CRMs described herein can also be prepared with other reversible crosslinkers, such as diazido compounds 3 and 4.

Preparation of bis(2-azidoethyl)disulfide (3):

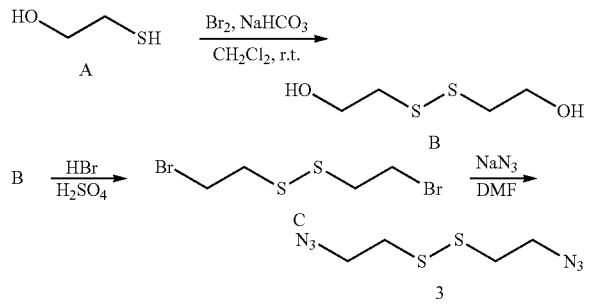

Preparation of bis-(2-hydroxy ethyl)disulfide (B): Aqueous sodium bicarbonate (10%, 40 mL) was added to a solution of 2-mercaptoethanol (A, 3.0 mL, 43 mmol) in dichloromethane (40 mL). A solution of bromine (2.0 mL, 39 mmol) in dichloromethane (10 mL) was slowly added while the mixture was stirred at 0° C. After addition, the organic phase was separated and the aqueous phase was extracted with dichloromethane (3×10 mL). The organic solvent was evaporated and the residual was purified by column chromatography (CH$_2$Cl$_2$:CH$_3$OH=3:1) to afford B as a colorless oil (0.34 g, 13%). $^1$H NMR (400 MHz, D$_2$O, δ): 3.81 (t, J=6.4 Hz, 4H), 2.85 (t, J=6.4 Hz, 4H).

Preparation of bis-(2-bromoethyl)disulfide (C): Concentrated H$_2$SO$_4$ (10 mL) was slowly added to a stirred 48% HBr aqueous solution (14 mL) at 0° C. Compound B (0.33 g) was added dropwise to the above mixture. After 24 hours at room temperature, the mixture was heated on a steam bath for 3 hours. Dichloromethane (10 mL) was added to the cooled reaction mixture. The organic layer was separated, washed with water and 10% Na$_2$CO$_3$ aqueous solution, dried over anhydrous Na$_2$SO$_4$, filtered, and concentrated to give compound C (0.48 g, 86%). $^1$H NMR (400 MHz, D$_2$O, δ): 3.63 (t, J=8 Hz, 4H), 3.12 (t, J=8 Hz, 4H).

Preparation of bis(2-azidoethyl)disulfide (3): Compound C (0.226 g, 0.95 mmol) was dissolved in DMF. To this solution was added sodium azide (0.31 g, 4.75 mmol) and the mixture was stirred at 80° C. for 10 hours. The product was extracted with ethyl ether three times. The combined organic layers were washed with brine, and dried over anhydrous Na$_2$SO$_4$. After filtration and evaporation, the product was dried under vacuum to give 3-1 as a yellow oil (0.162 g, 84%).

$^1$H NMR (400 MHz, CDCl$_3$, δ): 3.62 (t, J=6.8 Hz, 4H), 2.89 (t, J=6.8 Hz, 4H). See Rai et al., *Bioorg. Med. Chem.*, 2008, 16, 7301-7309.

Preparation of 1-(bis(2-azidoethoxy)methyl)-4-methoxybenzene (4):

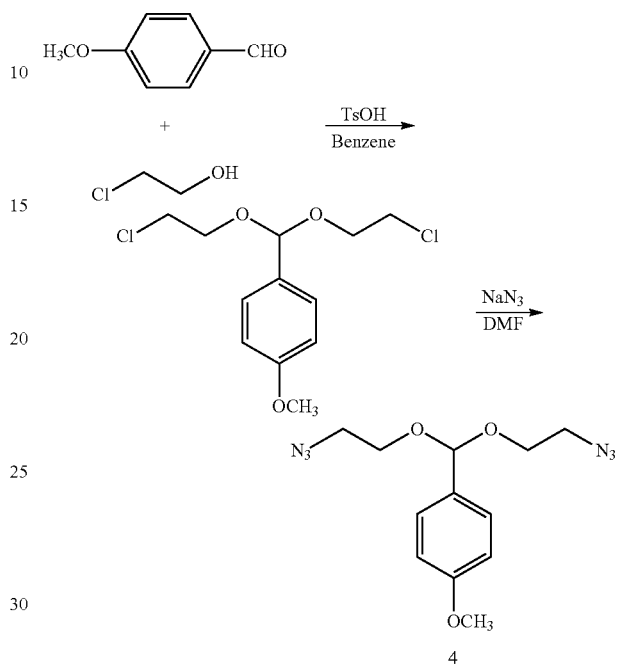

Preparation of 1-(bis(2-chloroethoxy)methyl)-4-methoxybenzene: 2-Chloroethanol (8.05 mL, 120 mmol), 4-methoxybenzaldehyde (6.07 mL, 50 mmol), benzene (25 mL), and p-toluenesulfonic acid (8.6 mg, 0.05 mmol) were combined and the mixture was heated to reflux. The water formed was removed by a Dean-Stark trap. When no additional water appeared in the Dean-Stark trap, the reaction mixture was cooled to room temperature and a solution of sodium methoxide (0.1 g) in 2 mL of methanol was added rapidly under stirring. The mixture was diluted with hexane, washed with brine, dried over anhydrous Na$_2$SO$_4$, filtered, and concentrated in vacuo. The crude product was used in the next step without further purification.

Preparation of 1-(bis(2-azidoethoxy)methyl)-4-methoxybenzene (4): Crude 1-(bis(2-chloroethoxy)methyl)-4-methoxybenzene (5.8 g) was dissolved in DMF. Sodium azide (13.5 g, 200 mmol) was added and the reaction mixture was stirred at 80° C. for 10 hours. The product was extracted with hexane three times. The combined organic layers were washed with brine, and dried over anhydrous Na$_2$SO$_4$. After filtration and evaporation, the product was dried under vacuum to give 4 as an oil. $^1$H NMR spectroscopy indicated that the oil was a 1:1 mixture of product and 4-methoxybenzaldehyde.

Example 4

Rapid Release of Entrapped Contents from Multi-Functionalizable, Surface Crosslinked Micelles It was surprisingly discovery that the SCMs can release entrapped contents extremely rapidly (<1 minute) upon cleavage of the crosslinkages. Because of the unparalleled tolerance of the click reaction to functional groups, SCMs were able to be prepared with a variety of crosslinkers and, as a result, different environmental stimuli can be used to trigger the release of the entrapped contents ("cargo"). This method combines the simplicity of physical entrapment with stimuli-triggered release of entrapped contents, making the SCMs highly useful in the delivery and controlled release of hydrophobic drugs.

Figure 14:
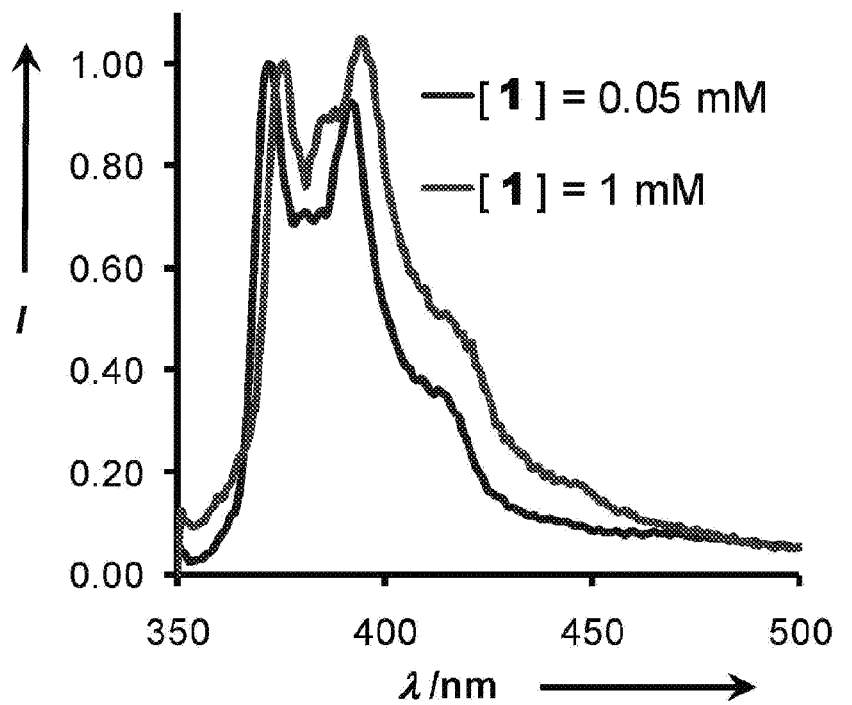
FIG. 14 illustrates normalized emission spectra of pyrene in the presence of surfactant 1 in water.

Pyrene was used as a surrogate for a hydrophobic drug because of its environmentally sensitive fluorescence. Pyrene has five vibronic bands that respond to environmental polarity differently. The intensity ratio between the third (~384 nm) and the first band (~372 nm), in particular, is sensitive to changes in the environment. As illustrated in FIG. 14, the emission spectrum of pyrene varies with the concentration of amphiphile 1. Changes in $I_3/I_1$ indicate that pyrene is in a more hydrophobic microenvironment in 1 mM aqueous solution of amphiphile 1 than in 0.05 mM. The CMC of the surfactant is about $1.4 \times 10^{-4}$ M according to surface tension measurement and $1.5 \times 10^{-4}$ M, according to FIG. 15.

Pyrene-containing SCMs were then prepared according to (FIG. 22), following similar procedures for the synthesis of SCMs described above. Briefly, an aqueous solution containing 38 μM pyrene and 10 mM of surfactant 1 was prepared. Because the solubility limit of pyrene in water is 0.67 μM, the majority of the dissolved pyrene resided within the surfactant micelles. Addition of a crosslinker (e.g., one or more of compounds 2-4) and $CuCl_2$/sodium ascorbate initiated the crosslinking and the reaction was allowed to continue for 12-24 hours at room temperature.

Entrapment of pyrene was confirmed by fluorescence spectroscopy. When the pyrene-containing SCMs were diluted by water so that the concentration of crosslinked 1 was below its CMC, $I_3/I_1$ of pyrene remained unchanged at 0.84-0.85 (the value above the CMC, see FIG. 15) for a period of more than six months. However, as soon as periodic acid ($HIO_4$) was added to the mixture to cleave the 1,2-diol group in the crosslinker, $I_3/I_1$ dropped quickly (FIG. 14). Remarkably, release of the pyrene was so rapid that, by the time $HIO_4$ was added and the solution was mixed by gentle vortexing (<1 minute), the change in $I_3/I_1$ was complete.

Figure 15:
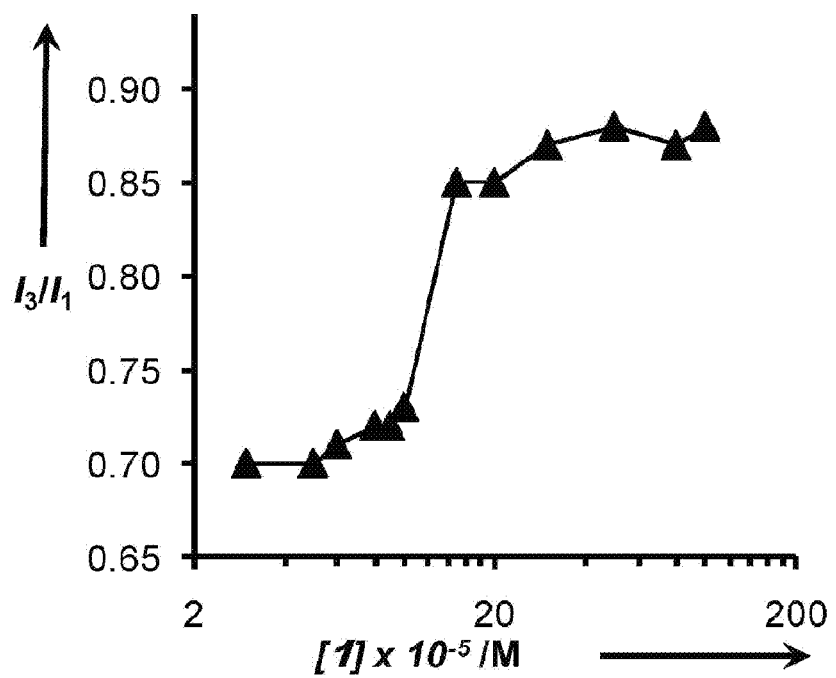
FIG. 15 illustrates pyrene $I_3/I_1$ ratio as a function of the concentration of surfactant 1.
Figure 16:
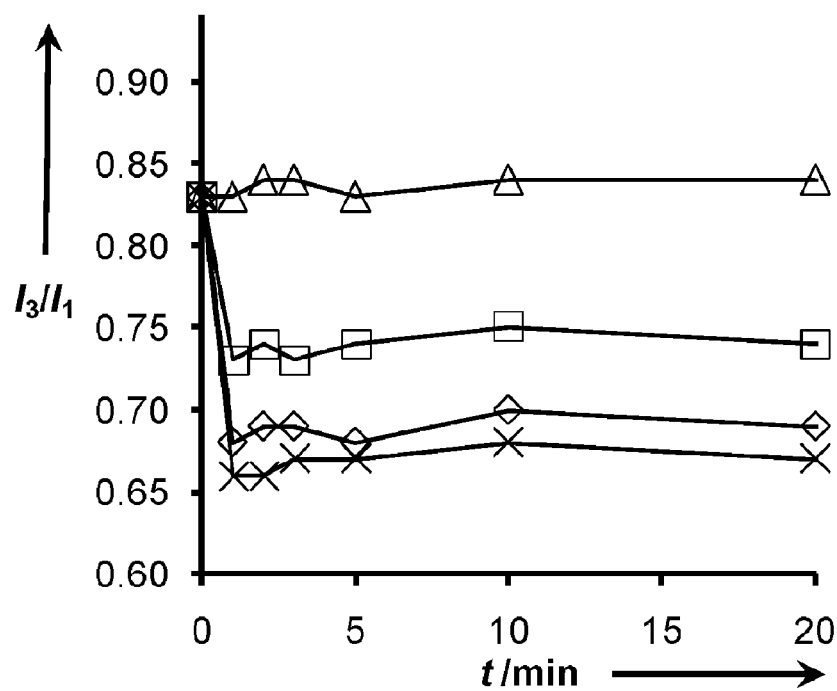
FIG. 16 illustrates the change of the pyrene $I_3/I_1$ ratio after addition of 0 (Δ), 1 (□), 10 (◇), and 100 (X) equivalents of cleaving agent to pyrene-containing SRMs. Crosslinker=2, cleaving agent=$HIO_4$.

The end $I_3/I_1$ value was somewhat dependent on the amount of $HIO_4$ added. One equivalent of the cleaving agent ($2 \times 10^{-5}$ M) reduced the $I_3/I_1$ to 0.74-0.75, higher than the 0.70 observed in the uncrosslinked surfactant below the CMC (FIG. 15). Some of the 1,2-diol groups may have been uncleaved under the latter conditions. The addition of 10 and 100 equiv of $HIO_4$ apparently disintegrated the SCMs quickly and completely (FIG. 16), as the final the $I_3/I_1$ was similar or even slightly lower than 0.70 in the uncrosslinked micelles. Incidentally, periodic acid at high concentration ($2 \times 10^{-3}$ M) was found to quench the fluorescence of pyrene significantly, which could explain why the $I_3/I_1$ ratio was even lower that the 0.70 observed for pyrene below the CMC of surfactant 1.

Figure 17:
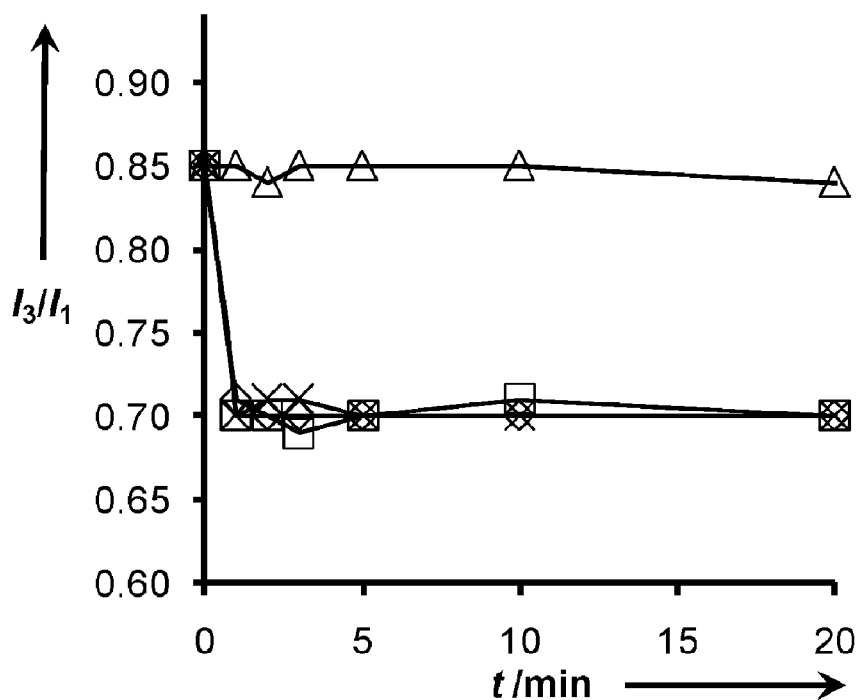
FIG. 17 illustrates the change of the pyrene $I_3/I_1$ ratio after addition of 0 (Δ), 1 (□), 10 (◇), and 100 (X) equivalents of cleaving agent to pyrene-containing SRMs. Crosslinker=3, cleaving agent=5; [1]=$2\times10^{-5}$ M.

The outstanding tolerance of the click reaction allowed for the incorporation of other stimuli-sensitive crosslinkers in the SCMs. Diazide 3, for example, contains a disulfide bond that can be cleaved by thiols such as dithiol 5. Release of pyrene was once again found to occur extremely fast after addition of 5 (FIG. 17). Excess 5 was not needed to reduce the $I_3/I_1$ ratio to 0.70 and 1 equiv of dithiol 5 was enough to completely release the entrapped pyrene.

Cleaving of 1,2-diol and disulfide bonds in crosslinked polymers was reported to take hours to days to complete and often require millimolar concentrations of reducing thiols (Sun et al., *Biomacromolecules* 2006, 7, 2871; Koo et al., *Chem. Comm.* 2008, 6570; Zhang et al., *Biomacromolecules* 2008, 9, 3321). In contrast, the SCMs expelled pyrene extremely rapidly. Considering the concentration ($2 \times 10^{-5}$ M) of the surfactant (in the pyrene-containing SCMs) and the releasing agent ($HIO_4$ or 5), the release was remarkably efficient. The electrostatic stress of the system likely speeds up the cleaving reaction compared to polymer micelle systems, resulting in rapid stimuli-triggered release by the SCMs.

Pyrene-containing the SCMs with acetal-containing 4 as the crosslinker were also prepared to evaluate the release of pyrene under acidic conditions because acid-triggered release is important in many delivery applications. For example, endosomes and liposomes are well known to be more acidic than the cytosols (Mellman et al., *Annu. Rev. Biochem.* 1986, 55, 663). Successful delivery by endocytosis often requires acid-triggered release, and cancerous and inflammatory tissues are also known to be more acidic than normal tissues (Helmlinger et al., *Clin. Cancer Res.* 2002, 8, 1284).

Initially, pyrene-containing SCMs prepared using acetal 4 showed no change in fluorescence at pH=5 over a period of 96 hours. The result was initially a surprise because the SCMs were surrounded by acidic water and the p-methoxybenzyl acetal group in 4 is highly prone to hydrolysis. The compound, for example, can undergo partial hydrolysis during water workup.

Figure 18:
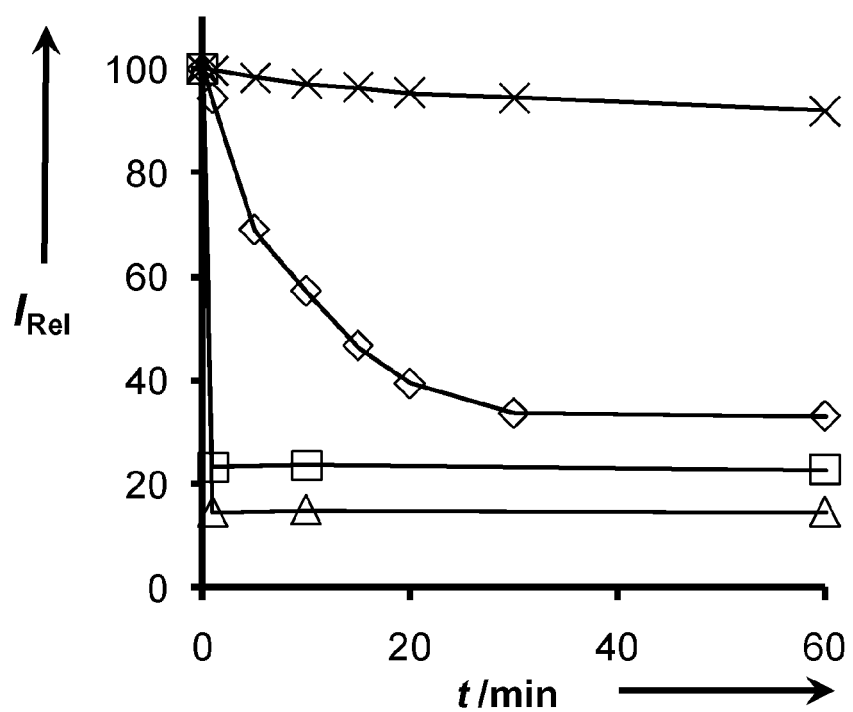
FIG. 18 illustrates the relative intensity of scattered light for the SRMs upon different stimulation. Stimulation was 1 equivalents of $HIO_4$ for SRMs crosslinked with 2 (Δ), 1 equivalents of acetal 4 for SRMs crosslinked with diazide 3 (□), and pH 5 (◇) and pH 7 (X) acetate buffer at 37° C. for SRMs crosslinked with dithiol 5.

Concerned that pyrene fluorescence did not directly monitor changes to the nanoparticles, dynamic light scattering (DLS) was employed. DLS correlates the scattered light with the diffusion coefficient of particulate species in the sample. FIG. 18 illustrates the percent change in the intensity of scattered light for various pyrene-containing-SCMs. Disintegration of the nanoparticles was once again found to be extremely rapid for SCMs prepared with 2 or 3 as the crosslinker (Δ and □, respectively). The intensity of scattered light dropped to 15 and 24% of the original value, respectively, when 1 equivalent of $HIO_4$ and dithiol 5 were added to the corresponding SCMs.

The change in light intensity was clearly slower for the acid-triggered disassembly. The nanoparticles prepared with acetal 4 as the crosslinker disintegrated gradually over the period of 60 minutes at 37° C., although the majority of the change occurred in the first 20 minutes. The intensity of scattered light dropped to 15% of the original value after 48-96 hours. In contrast, the nanoparticles at pH=7 displayed negligible changes in scattered light over 96 hours. A hydrogel crosslinked with a similar p-methoxybenzyl acetal was reported to release entrapped protein over several hours instead of 20 minutes (Murthy et al., *J. Am. Chem. Soc.* 2002, 124, 12398).

In summary, it was found that the SCMs could eject entrapped hydrophobic contents extremely rapidly upon cleavage of the surface crosslinkers. As indicated by Scheme 4-1 and demonstrated by the examples above, multivalent surface functionalization of these nanoparticles is readily accomplished by addition of azide-functionalized polymers and ligands. A combination of crosslinkers may be used and the acid- or redox-sensitivity of the SCMs can be tailored for specific applications.

This simple method combines the ease of physical entrapment and the preciseness of chemical ligation and therefore does not require any covalent modification of the entrapped agents. With the additional benefits of multivalent surface modification, tuning of surface charge (e.g., by using anionic, nonionic, or zwitterionic surfactants with multiple alkynyl groups), and outstanding tolerance of the click reaction for functional groups, the SCMs can be useful materials for active agent delivery and controlled release.

Example 5

Preparation of Phospholipid Vesicles by Extrusion

To prepare phospholipid vesicles by extrusion, phospholipids are first suspended in a buffered saline solution to give large, multilamellar vesicles. The vesicles are then repeatedly passed through a polycarbonate filter with 100 nm pores. The result is uniformly sized, unilamellar vesicles (large unilamellar vesicles, or LUV), approximately 100 nm in diameter. A LIPOSOFAST extruder from Avestin, Inc. (Ottawa, Ontario, Canada) is suitable for the extrusion. The LIPOSOFAST extruder is a syringe-based membrane extruder that is inexpensive and easy to use, and it allows one to prepare 0.5 to 1 mL batches of phospholipids at a time. Another suitable vesicle extruder, the Mini-Extruder, is available from Avanti Polar Lipids (Alabaster, Ala.).

Note that the phospholipids must be handled at a temperature above their transition temperature (Tc) from gel to liquid crystalline phase. The natural phospholipids are generally used, which are in the liquid crystal phase at room temperature. If other types of phospholipids are used, it may be necessary to carry out the preparatory procedures at a temperature above the Tc (not necessarily at room temperature). Alternative procedures to make unilamellar vesicles include sonication, detergent/dialysis and detergent/Bio-Beads.

Materials and Solutions: HEPES buffered saline (HBS): 100 mM NaCl; 20 mM Hepes/NaOH buffer, pH 7.5; 0.02% (w/v) sodium azide. Alternatively, 50 mM Tris buffer, pH 7.5, may be substituted for the Hepes buffer. The HBS should be stored at room temperature.

| Phospholipid Stock Solutions | | | |
|---|---|---|---|
| | Phospholipid name | Concentration | MW |
| PC | L-alpha-Phosphatidylcholine, egg | 10 or 25 mg/mL | 761 |
| PS | L-alpha-Phosphatidylserine, bovine liver-Na salt | 10 mg/mL | 810 |
| PE | L-alpha-Phosphatidylethanolamine, bovine liver | 10 mg/mL | 768 |

Phospholipid Stock Solutions can be purchased from commercial suppliers such as Avanti Polar Lipids (Alabaster, Ala.), dissolved in chloroform. Stock solutions should be stored at −20° C. under argon and should not be stored for more than 3 months (6 months for PC).

Methods:

1. Dispense 2.6 μmole total phospholipids (PL) in a glass test tube (a 13×100 mm tube is a convenient size). Examples of amounts of PL to use in making PCPS or PCPSPE vesicles include the following:

| For PC:PS vesicles (80:20 molar ratio) | | |
|---|---|---|
| 63 μL PC (at 25 mg/mL) (or 158 μL at 10 mg/mL) = | 1.58 mg = | 2.08 μmole |
| 42:L PS (at 10 mg/mL) = | 0.42 mg = | 0.52 μmole |
| For PC:PE:PS vesicles (40:40:20 molar ratio) | | |
| 32:L PC (at 25 mg/mL) (or 79 μL at 10 mg/mL) = | 0.79 mg = | 1.04 μmole |
| 80:L PE (at 10 mg/mL) = | 0.80 mg = | 1.04 μmole |
| 42:L PS (at 10 mg/mL) = | 0.42 mg = | 0.52 μmole |

The contents of the stock vials of phospholipid should be overlaid with argon gas before capping and returning them to the freezer.

2. In the fume hood, dry the PL mixture under a gentle stream of nitrogen or argon. When dry, speed-vac for an additional 1 hour to overnight under high vacuum, to remove any residual chloroform.

3. To the dried-down PL, add 2.6 mL room temperature HBS solution and cover the end of the tube, such as with parafilm. Incubate 1 hour at room temperature with intermittent agitation.

4. Vortex tube vigorously to completely resuspend the PL. The result should be a milky, uniform suspension. Freeze and thaw the suspension three to five times. For example, freeze in dry ice/alcohol bath; thaw rapidly at 37° C.

5. Clean the LIPOSOFAST device with ethanol and dry it well. Assemble the device with two membranes held between the two "O" rings and filter supports according to the manufacturer's directions. Two polycarbonate membranes with 100 nm pore size are generally suitable, although other pore sizes can also be used.

6. Load 0.5 mL of the lipid suspension into one of the two glass syringes and attach it to the Luer lock on one side of the device. Close the other (empty) syringe and attach it to the Luer lock on the opposite side of the device.

7. Press the loaded syringe to pass its entire contents through the filter and into the opposing syringe. Repeat this process alternately with the two syringes for a total of at least about 11 passes. It is important that an odd number of passes are employed, so that the final product ends up in what was originally the empty syringe. This will ensure that none of the starting multilamellar vesicles will contaminate the final product. In addition, it is important that this procedure be performed at a temperature that is above the Tc for your lipid mixture.

8. Remove the final product and repeat steps 6 and 7 for the remaining, unprocessed phospholipid suspension, until all of the suspension has been processed.

9. Store the final product at 4° C. The result is a uniform suspension of unilamellar vesicles (about 100 nm in diameter) containing a total of 1 mM phospholipid in HBS.

The final phospholipid concentration can be confirmed by assaying total phosphorus content. Additional description and techniques are described by Mui et al., *Extrusion technique to generate liposomes of defined size; Methods Enzymol.* (2003) 367:3-14. See also http://www.avantilipids.com/extruder.html;
http://www.avantilipids.com/ExtruderAssembly.html; and
http://www.avantilipids.com/LUVET.html.

Example 6

Crosslinked Organic Particles for Catalysis

Diminishing natural resources, deteriorating environmental conditions, and rising green-house gases in the atmosphere have placed great challenges for creating efficient catalytic processes. Development of energy-efficient and environmentally benign catalysis is important to a sustainable chemical industry. Due to its abundance, nonflammability, and nontoxicity, water is an attractive solvent for green chemical transformations. Although a number of organic reactions are being carried out in water on industrial scales, expanding the scope of aqueous-based industrial organic reactions requires fundamentally new concepts in catalytic technology.

This example provides methods to expand aqueous biphasic catalysis using hydrophobic organometallic catalysts entrapped within crosslinked micelles. The surface-crosslinked micelles (SCMs) can improve mass transfer and product separation of organic reactions in comparison to conventional technologies for aqueous biphasic catalysis.

Background. Aqueous biphasic catalysis is an attractive process for transition-metal catalyzed organic reactions. Water, as a green solvent, is abundant, nonflammable, and nontoxic. The high heat capacity of water is beneficial to the temperature control of a reaction. Recovery and recycling of the catalyst, as well as separation of products, are straightforward when they reside in two immiscible phases. In addition, water can speed up certain organic reactions by hydrophobic effects. Indeed, aqueous-based catalysis is being used in a number of industrial organic transformations, including hydroformylation of propene to butyraldehyde, hydrodimerization of butadiene, and the Wacker oxidation.

Expanding the scope of aqueous biphasic catalysis, however, faces significant challenges. Some approaches to aqueous-based organic reactions using transition metal catalysts attach water-soluble groups (e.g., sulfonate, sulfate, ammonium, carboxylate, phosphate, or hydroxyl) or polymers to the metal-binding ligands. Researchers have also anchored catalysts on insoluble solid supports such as silica. Over the last decades, a large number of ligands have been designed and synthesized, allowing aqueous-based catalysis successfully performed on the lab scale for a growing number of reactions, e.g., hydroformylation, hydrogenation, olefin polymerization, olefin metathesis, cross-coupling, and catalytic oxidation.

Scaling up these aqueous reactions to the industrial scale, however, remains highly challenging. Pulling transition metal catalysts into water, in fact, is the easier part of the problem. Getting the organic reactant to come in contact with the water-soluble catalyst is typically more challenging. Although there are methods to improve the solubility of organics in water, e.g., by adding water-miscible organic co-solvent or surfactants, these methods inevitably compromise product isolation. The presence of organic solvent will render both the reactant and product more soluble. Because of the high heat capacity of water, separation of the (water-miscible) organic solvent is energy-intensive and organic solvent-containing water is no longer nontoxic and creates an environmental hazard. Although surfactants can promote dissolution of organic molecules in water, their surface activity promotes emulsion formation, which is a significant problem in a chemical process in which good phase separation is important for product purification.

This example describes a method to trap unmodified or largely unmodified transition metal catalysts in highly crosslinked micelles. The overall structures have striking resemblance to enzymes in the sense that the catalytic site is located within a hydrophobic microenvironment suspended in the aqueous phase. The effective concentration of the substrate is enhanced by the hydrophobic micelle and mass transfer is facilitated by the fast exchange of organic reactant/product from micelle to micelle (and to the organic bulk phase). The straightforward synthesis of the crosslinkable surfactants and SCMs, as well as the ability of using unmodified or largely unmodified conventional ligands for the transition metal catalysts, makes the method practical and applicable to large industrial reactions.

The examples above describe a simple method to crosslink surfactant micelles. The reaction design includes, for example, a highly alkynylated surfactant 1, synthesized in a few simple steps from inexpensive, commercially available starting materials. Highly efficient click reactions (i.e., 1,3-dipolar cycloaddition between a terminal alkyne and an azide) were used for crosslinking, which occurs at room temperature in the presence of an azide-containing crosslinker (e.g., 1,4-diazidobutane-2,3-diol (2a)) and Cu(I) catalyst above the CMC of 1, $1.5 \times 10^{-4}$ M in water (FIG. 23). Although hydrophobic crosslinkers such as 1,4-bis(azidomethyl)benzene (2b) or 1,3-diazidopropan-2-one (2c) may be used as well, water-soluble crosslinkers such as 2a gave suitable results. The resulting nanoparticles were about 8-10 nm in diameter according to dynamic light scattering (DLS) and about 10 nm by TEM.

(1) Hydrophobic Organometallic Catalysts Entrapped within SCMs. A one-step synthesis of SCMs using the highly efficient click chemistry is discussed above. High surface-crosslinking density enabled physical entrapment of small hydrophobic guests (e.g., pyrene or drug molecules) within the core of the micelle even when the sample was diluted below the CMC of the surfactant. Water-soluble catalytic nanoparticles can be prepared by physically or chemically trapping phosphine- and salen-complexed transition metal catalysts inside the SCMs. The micellar environment not only allows direct solubilization of unmodified or largely unmodified hydrophobic catalysts in water but also can greatly facilitate mass transfer between the water-insoluble organic reactant and the catalyst in the aqueous phase. By covalently crosslinking the surfactants in the micellar configuration, the surface activity of the surfactant is eliminated and emulsion formation, a serious plague for the separation of products in traditional surfactant-assisted organometallic catalysis, can be avoided. Cooperative catalysis and site-isolation can be implemented, further improving the catalytic efficiency and selectivity.

(2) Increased Hydrophobic Free Volume within SCMs. The packing density of the hydrocarbon tails within the SCMs can be decreased, thereby providing increased voids or "hydrophobic free volume". These voids are typically currently filled with water but would readily accept organic compounds. In aqueous biphasic catalysis, the hydrophobic free volume of an SCM increases its affinity for the organic reactant. Three strategies can be used to decrease the hydrophobic packing density of the SCMs: (a) using crosslinkable surfactants with sacrificial hydrophobes, (b) using crosslinkable surfactants with removable, noncovalent or reversible covalent linkages, and/or (c) using uncrosslinkable diluents (organic solvent or amphiphiles). With larger hydrophobic free volume inside the SCM, the effective concentration of the substrate increases near the transition metal catalyst, thereby improving catalytic efficiency.

By trapping organometallic catalysts in crosslinked micelles, the need for ligand-modification for catalysts is eliminated and the approach avoids the dichotomy derived in conventional aqueous-based biphasic catalysis, i.e., efficient mass transfer between the reactant organic phase and the water-soluble catalyst prefers maximal miscibility of the organic and the aqueous phase, but efficient product separation prefers minimal miscibility.

These two approaches are complementary and synergistic. Suitable organometallic catalysts can be identified by the first approach and can be used to optimize key parameters such as surfactant structure, crosslinking density, catalyst loading, and reaction conditions. The second approach can be performed independent of the first, using fluorescent probe to monitor the hydrophobic free volume of the SCMs. The data obtained can be applied to catalysis directly to improve substrate binding and mass transfer. Application of this technology will expand the scope of aqueous based catalytic organic reactions.

Hydrophobic Organometallic Catalysts Entrapped within SCMs. The crosslinking method can be used to prepare water-soluble SCMs with phosphine- or salen-complexed transition metal catalysts trapped inside, for use with industrially important reactions such as hydrogenation, hydroformylation, and olefin epoxidation. Other reactions (e.g., palladium-catalyzed cross-coupling) may also be carried out using these procedures. The micellar environment not only allows solubilization of unmodified or largely unmodified hydrophobic catalysts in water but also greatly facilitate the mass transfer between the water-insoluble organic reactant and the catalyst. Crosslinking enables site isolation of the catalyst and may shut off certain catalyst decomposition/deactivation pathways. The catalyst can also be used at higher concentrations in the aqueous phase, thereby increasing the reaction rates. For catalysts that benefit from cooperative interactions of two or multiple metal centers, two or multiple catalysts can be trapped in the same SCM. The micellar body itself, with its surface charges, can also be useful in enhancing the catalytic efficiency.

Design and Preparation of SCM-Encapsulated Catalysts. Phosphine is an extremely versatile ligand in organometallic catalysis. Industrially important reactions such as hydrogenation, hydroformylation, and cross-coupling may be catalyzed by phosphine-complexed transition metals. Scheme 6-2 lists several commercially available phosphine ligands that can be entrap within the SCMs.

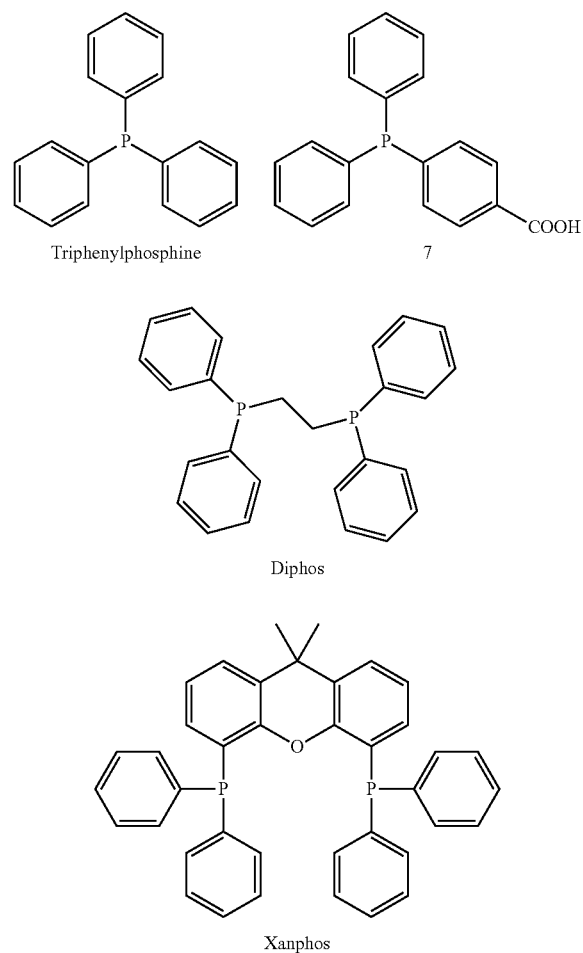

Scheme 6-2. Commercially available phosphine ligands trappable within SCMs

Triphenylphosphine

7

Diphos

Xanphos

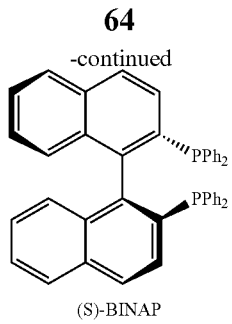

(S)-BINAP

Figure 19:
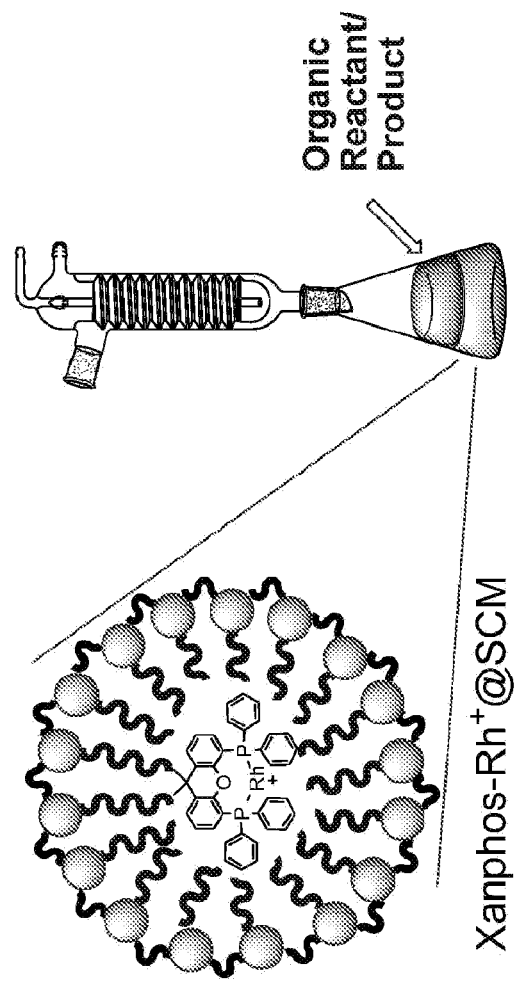
FIG. 19 illustrates the preparation of an SCM-encapsulated phosphine-rhodium catalyst.
Figure 19:
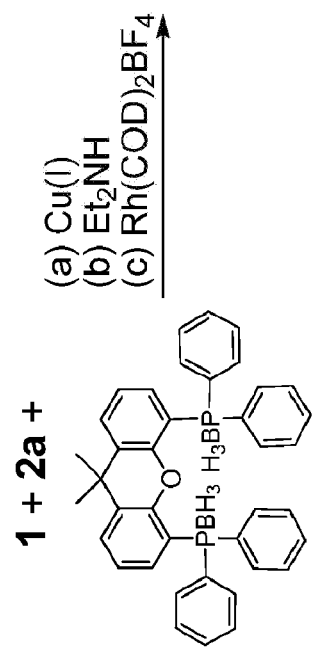

Preparation of a SCM-encapsulated phosphine-rhodium catalyst is shown by FIG. 19. The procedure is adapted from the pyrene-entrapment discussed above. As an example, a hydrophobic phosphine (e.g., Xanphos) can be first protected by borane in a well-established procedure (Brunel et al., *Phosphane-boranes: synthesis, characterization and synthetic applications. Coordin Chem Rev* 1998, 180, 665-698). Protection is important because phosphines (especially alkyl substituted) can be oxidized in air and readily react with azides via the Staudinger reaction. Protection with borane eliminates these problems and enables the phosphine-borane complex to be included inside the SCMs similarly to pyrene. After crosslinking, treatment with an amine (e.g., $Et_2NH$) can generate the free phosphine inside the SCM. The active catalyst can be prepared by combining the phosphine-containing SCMs and a Rh(I)-precursor, e.g., $Rh(COD)_2BF_4$. The biphasic catalysis is shown schematically by the two-layer mixture in FIG. 19. The top phase contains the water-insoluble organic reactant/product and the catalyst-containing SCMs are located in the bottom aqueous phase. Rapid stirring is important to phase-separated reactions.

(1) As shown in FIG. 19, the catalyst is located within a hydrophobic (top) micro-environment even though the surrounding SCM is in the aqueous (bottom) phase. This arrangement differs from conventional biphasic catalysis in which the catalyst is surrounded by water. Whereas the organic reactant will have difficulty approaching the catalyst in the conventional method, it can easily get into the hydrophobic micelle to come in contact with the catalyst. Because both the reactant and the catalyst are confined in a nanosized microenvironment, significant rate acceleration may be observed due to the higher effective concentration of the substrate near the catalyst.

Conventional micelles are dynamic assemblies of individual surfactants. For ionic surfactants, the typical residence time for a surfactant within a micelle is on the order of $10^{-6}$-$10^{-7}$ s. In an SCM, the surfactants are fixed by covalent bonds but the reactant and product are free to move about. Given the fast exchange of surfactant between micelles, even if the exchange of reactant is several orders of magnitude slower, it can still be a bottleneck to most organic reactions. If a surfactant with 12 to 16 carbons can move from one micelle to another quickly, organic molecules with fewer carbons should be able to do similarly because the barrier (i.e., exposure of hydrophobic surface to water) for a reactant/product to migrate from one SCM to another is the same as that for a surfactant to jump from one micelle to another.

(2) Surfactants have been used in aqueous-based organic reactions to solubilize the reactant and/or the catalyst. However, they promote emulsion formation between the organic and aqueous components and create enormous problems in product separation. Alternatively, one can enhance the solubility of the reactant by adding a water-miscible organic co-solvent, but the increased solubility is achieved at the expense of product separation and water-contamination. In our described method, the surfactants are fixed by crosslinking in the micellar configuration. Because the SCMs are completely hydrophilic on the exterior, the materials are not believed to have surface activity. In this way, fast mass transfer and good product separation can be achieved at the same time.

(3) The catalysts are encapsulated within the SCMs and isolated from one another. Site isolation may not only avoid certain pathways (e.g., dimerization or bridging) for catalyst decomposition, but can also allow their use at relatively high concentrations in the aqueous phase, both of which can speed up the reaction. Cascade reactions are achievable when different SCM-entrapped catalysts are present at the same time. Such reactions are frequently found in biological systems (e.g., metabolism) but are often hampered by catalyst incompatibility.

(4) Certain catalysis reactions (e.g., epoxide hydrolysis catalyzed by Co-Salen complexes) benefits from cooperativity between two metal centers. The methods described herein permit simultaneous trapping of two or multiple catalysts within an SCM. In typical homogeneous catalysis, the encounter between the reactant and the catalyst is collision-based. The time of encounter can be significantly shorter than in the SCM-based catalysis, where the organic reactant may stay in the same SCM for longer period of time, thereby increasing cooperativity.

(5) The affinity between the SCM and the organic reactant can be tuned in a rational fashion. As the affinity of the SCM for the reactant is increased, one can increase the effective concentration of the substrate near the catalyst.

(6) As shown by FIG. 19, preparation of the encapsulated catalysts involves simple synthesis with commercially available ligands. This translates to lower costs in the production of the catalysts. With excellent mass transfer and easy product separation, the method is applicable to large industrial reactions.

Alternative Embodiments. Many transition metals require more than one phosphine ligand for stabilization. The Wilkinson catalyst [RhCl(PPh$_3$)$_3$], which catalyzes homogeneous hydrogenation of unhindered alkenes, needs at least two phosphines in the active form. A simple way to achieve this is to trap a bisphosphine ligand such as Diphos inside the SCM. Another strategy is to employ commercially available acid-functionalized phosphine 7 (Scheme 6-2 above). With electrostatic interactions between the carboxylate form of 7 and cationic 1, one can include multiple molecules of compound 7 within an SCM. The triarylphosphine can be located inside the micelle instead of in the aqueous phase due to its hydrophobicity.

Most ligands discussed herein are large in comparison to common organic reactants and products. If a large ligand/catalyst can be physically trapped within the SCM without other adverse effects (e.g., in mass transfer), physical entrapment can be achieved. Pyrene trapped inside the SCMs stayed inside the micelle for more than 6 months when the SCM was diluted below the CMC of 1 and pyrene concentration was well below its solubility in water, indicating physical entrapment. In some embodiments, the crosslinking density for physical entrapment of a hydrophobic ligand/catalyst may be higher than the initially prepared particles described above. The organic reactant and product can pass in and out of the SCM. Thus, untrapped ligands/catalysts may be extracted and may leach into the organic phase. Two strategies can be used to address these issues.

(a) The crosslinking density of the SCMs can be increased. Instead of bis-azide such as 2a, tris-azide 8 or 9 can be used as a crosslinker. Data indicates that water-solubility is helpful to the crosslinking. In some embodiments, compound 9 can provide improved crosslinking than compound 8, which is less polar. Surfactant 10 can also be used as a crosslinker. Being very similar in structure, it can form mixed micelles with 1, which can be readily crosslinked to form highly crosslinked SCMs.

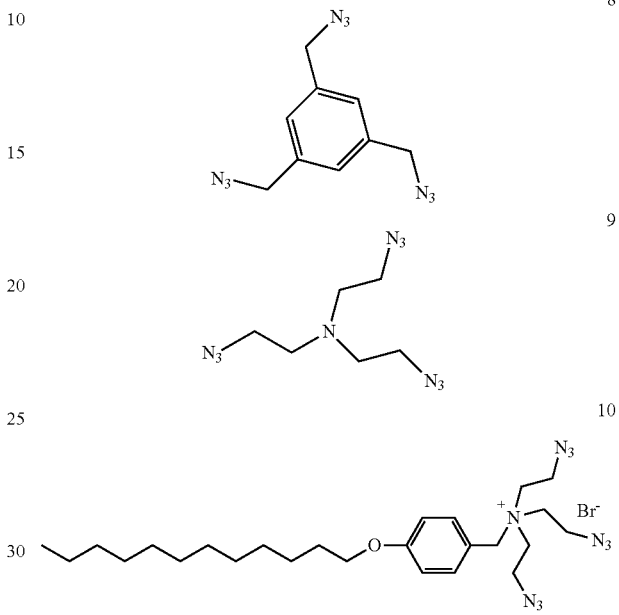

Triphenylphosphine-containing (or pyrene-containing) SCMs with different crosslinkers can be used to evaluate crosslinking density. The SCMs can be dried and stirred in a large amount of organic solvent (e.g., CHCl$_3$). The concentration of triphenylphosphine (or pyrene) can be determined by appropriate techniques (NMR or fluorescence) to identify potential leaching. Soxhlet extraction can also be used for evaluating crosslinking density. If the ligand/guest molecule within the SCMs can survive Soxhlet extraction using a range of solvent, e.g., EtOH, CHCl$_3$, hexane, the chance of leaching will be minimal.

(b) Covalent fixation of the ligand. Physical entrapment allows commercially available hydrophobic ligands such as Diphos, Xanphos, or BINAP to be directly used. Nonetheless, too high a crosslinking density may be detrimental if relative large reactants/products are involved and/or high mass transfer is critical. In some cases, it may be preferable to keep the crosslinking density relatively low while having the ligand covalently attached to the SCMs. Azide-functionalized phosphine-borane complexes 11-13 can be readily prepared using standard techniques All three ligands can be prepared in two to three simple steps from commercially available phosphines. The azide group allows their covalent attachment to the SCMs during crosslinking. As before, the borane can be removed by an organic base after the SCM preparation.

Organic Reactions Catalyzed by SCM-Containing Phosphine-Complexed Transitions Metals. A range of phosphine-containing SCMs can be prepared. Crosslinking density, mono- or bi-dentancy, physical or chemical entrapment, chirality (e.g., Diphos vs. BINAP), and bite angle (e.g., Diphos vs. Xanphos) can be varied during preparation. To evaluate the effectiveness of SCM-encapsulated catalysts, two industrially important reactions can be analyzed.

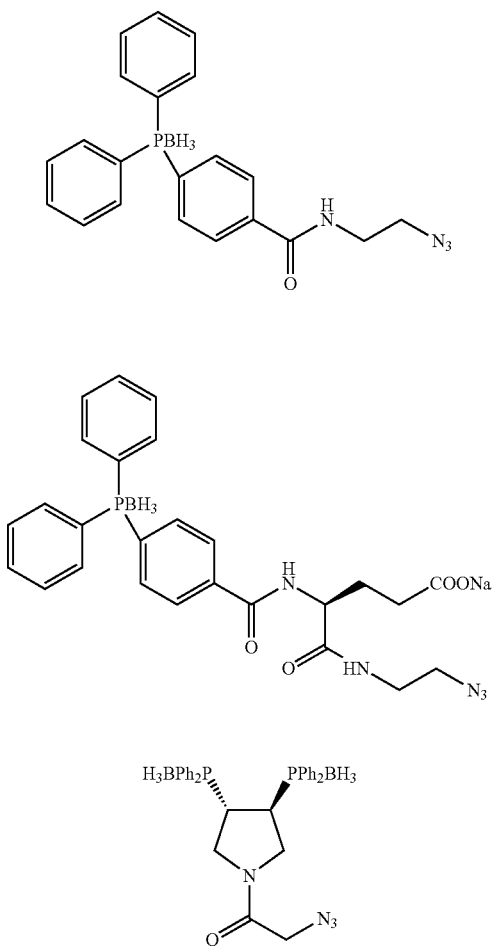

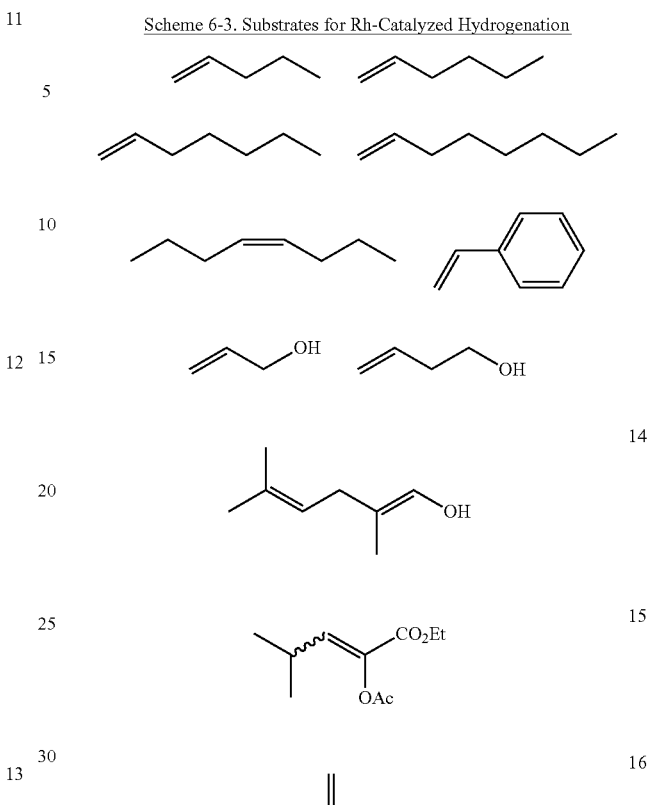

Scheme 6-3. Substrates for Rh-Catalyzed Hydrogenation (a) Rh-Catalyzed Hydrogenation. The reaction can be performed under standard literature conditions (see Joo, *Aqueous biphasic hydrogenations; Accounts Chem Res* 2002, 35, (9), 738-745). Briefly, the phosphine-containing SCMs and a Rh(I)-precursor, such as $Rh(COD)_2BF_4$, can be mixed in water to form the catalyst. The reaction can be carried out at room temperature and followed by NMR or GC analysis. Scheme 6-3 lists examples of the substrates that can be used in the biphasic hydrogenation. The results can then be compared with homogeneous catalysis using the same amount of catalyst. The benefit of biphasic catalysis is the ease of product separation and catalyst recovery. The reaction can be accelerated by higher pressure of hydrogen and/or larger concentration of catalyst.

Relatively hydrophilic substrates can be used in the reactions. Allyl alcohol, for example, is miscible with water. When hydrophilicity decreases from allyl alcohol to 3-buten-1-ol and then to geraniol (14), the reactivity can be closely monitored to determine relative reactivity. It Aromatic hydrocarbons are less hydrophobic than corresponding aliphatic compounds. Since 1 has an aromatic moiety in the structure, the aliphatic and aromatic olefins can have different affinities for the SCM. Finally, prochiral substrates such as 15 and 16 can be evaluated by these reactions. Micelles can increase the enantiomeric selectivity of transition metal catalysts and the SCMs can have a similar effect.

(b) Rh-Catalyzed Hydroformylation. Hydroformylation is an important industrial process because heterogeneous catalysis is challenging for this reaction (unlike hydrogenation). Water-soluble sulfonated phosphines have been used successfully for hydroformylation of low olefins. However, as the chain length increases, mass transfer becomes inefficient and the reaction rate becomes unacceptable. Hydroformylation of linear olefins (e.g., 1-pentene through 1-dodecene) can be performed with phosphine-containing SCMs. These olefins can enter the SCMs and be converted. As long as the reactant and product can quickly exchange with those in the bulk organic phase, reasonable reactivity can be maintained. Bite angle is known to be important to the activity of the Rh catalyst. Xanphos, for example, is particularly active. The linear/branched selectivity in these hydroformylation can be evaluated using the SCMs described herein.

Metallosalen Catalysts Encapsulated within SCMs. Metallosalens catalyze a wide variety of reactions including epoxidation, epoxide hydrolysis, cyclopropanation, and aziridation. These additional reactions and their unique features can open up new strategies in the catalyst design and allow testing of novel catalytic concepts. Chart 3 lists several metallosalens to be studied. Their sizes are comparable to the phosphines shown in Chart 2; thus the strategies mentioned above (i.e., higher crosslinking density and covalent fixation) should be useful for trapping the catalysts inside the SCMs. Unlike the phosphines, salen-metal complexes are compatible with the click chemistry and may be directly incorporated.

Scheme 6-4. Salen complexes to be trapped within SCMs

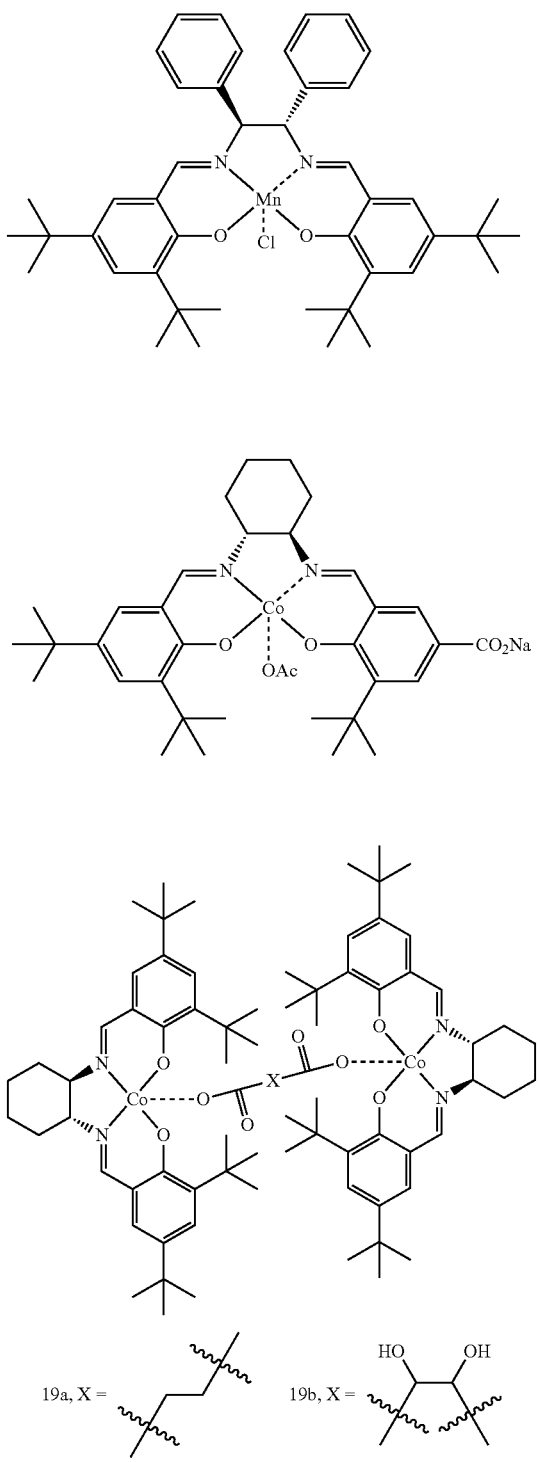

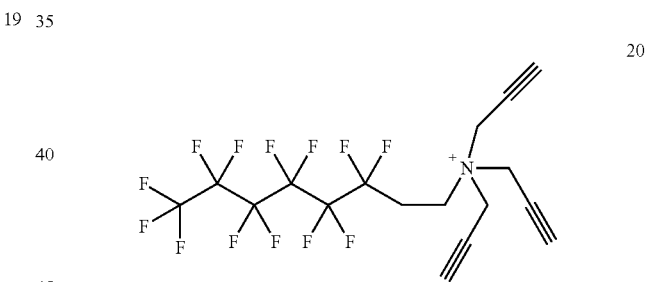

Two reactions catalyzed by metallosalen complexes-catalytic epoxidation of olefins by Mn(III)-salen (17) and epoxide hydrolysis[51-52] using Co(III)-salen (18 or 19) can be carried out using the particles described herein. Catalyst 17 is extremely effective at asymmetrical epoxidation of olefins. For the catalytic epoxidation, established substrates such as (Z)-prop-1-enylbenzene and cis-methyl cinnamate can be used to evaluate the biphasic catalysis. The reaction rates and enantiomeric selectivity can be compared with those in homogeneous reactions.

The cheapest and most effective oxidant for the metallosalen complexes-catalytic epoxidation of olefins is bleach (NaClO). Because the SCMs are positively charged on the surface, the hypochlorite (ClO$^-$) anion can be concentrated on the SCM surface. A rate acceleration, unavailable in a homogeneous system, may result. Also, the active catalyst is an oxo-Mn(V)-salen complex and tends to form unreactive μ-oxo-Mn(IV) dimers unless an additive such as 4-phenylpyridine N-oxide or N-methylmorpholine N-oxide is present. The catalyst of interest can be trapped inside the SCM. If the micelle/catalyst ratio is high during the crosslinking, a single catalyst within an SCM (although some SCMs may be empty) can be confirmed and can avoid the additive. Although an additive may not be a problem on a laboratory scale, its elimination in an industrial reaction represents a significant improvement, particularly for separating the product by decantation (as in biphasic catalysis).

One issue with of concern with epoxidation reactions is the strong oxidizing abilities of the oxo-Mn(V) species formed during the catalysis. Under certain conditions, the hydrocarbon chain of the crosslinked 1 may be oxidized over time. Oxidation may not be a problem when a large excess of the olefin substrate is present. However, any potential oxidation of the SCMs will affect the catalyst lifetime and recycling may become problematic. A solution to this potential problem is the preparation of a fluorocarbon version of the crosslinkable surfactant, e.g., 20. The Mn-salen complex inside the SCM in this case will be essentially in a Teflon-lined nanoreactor, which is highly stable toward oxidation.

Co(III)-salen complexes is efficient at catalyzing kinetic resolution of epoxide by hydrolyzing one enantiomer of a chiral epoxide faster than the other. The catalysis is known to operate through cooperation between two metallosalen complexes, with one activating the epoxide and the other water. The same strategies to incorporate multiple phosphines may be used with the methods described herein. For example, catalyst 18 has an anionic carboxylate; its electrostatic interactions with the cationic surfactant (1) can allow multiple Co-salen complexes to be included.

Another strategy to include two salen catalysts within a single SCM is to use a dicarboxylate ($^-$OOC—X—COO$^-$) as a ligand for the Co(III) species. Catalyst 19a (Scheme 6-4) can be prepared by ligand exchange of a monomeric Co(III)-salen complexes with a dicarboxylic acid. After its incorporation inside the SCMs, the dicarboxylate can be removed using a large excess of acetate. Such a step is important because the epoxide and the water molecule on opposite faces of the Co-Salen dimer will not be able to react easily. In the unlikely event that acetate is unable to displace the dicarboxylate, 19a can be used, which contains a germinal diol group.

The group can be readily cleaved by periodate, generating two Co(III)-salen complexes from the dimer.

Site isolation of catalyst is an important factor in the methods described herein. Site isolation of the catalysts can allow for cascade reactions catalyzed by two or more catalysts. The conversion of olefins to diols through the epoxide intermediate can therefore be evaluated. Because both Mn(III)-salen and Co(III)-salen catalysts can be prepared, the two SCM-encapsulated catalysts can be combined to perform epoxidation and hydrolysis in one pot. Chiral Co(III)-salen is no longer needed in this case, as the epoxide intermediate will be chiral from the asymmetric epoxidation.

fluorescent probe. When incorporated inside micelles, dansyl has been shown to be able to indicate the "wetness" of micelles. Ionic micelles, for example, have been demonstrated by dansyl probes to be "wetter" or more polar in the interior than nonionic micelles. To include a dansyl group in the interior of an SCM, an azide-containing dansyl derivative (e.g., 21) can be used, which can be synthesized from commercially available materials in two simple steps. Because of its hydrophobicity, 21 can be solubilized in the interior of the micelles and covalently crosslinked with 1 during the click-crosslinking.

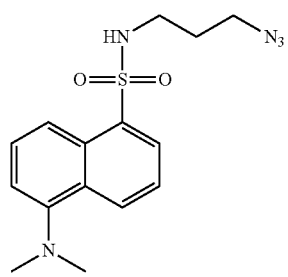
21

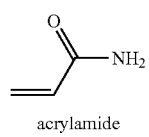
acrylamide

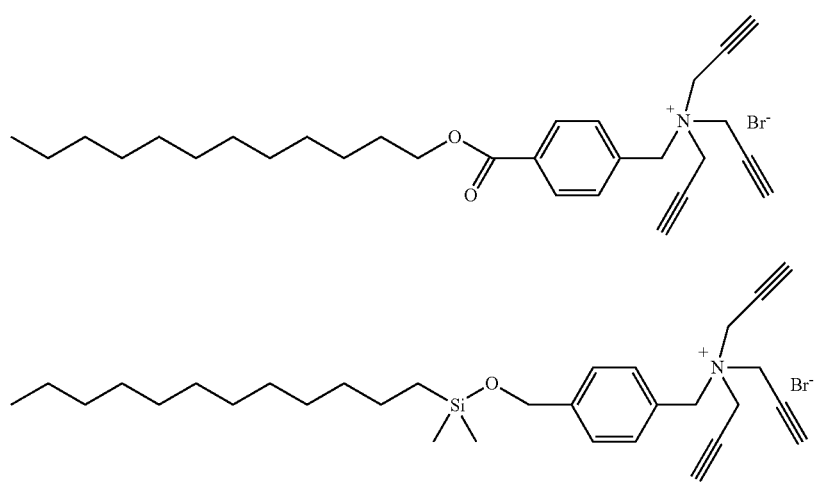
22

23

Increasing Hydrophobic Free Volume within SCMs. Ionic surfactants form micelles in a compromise between the hydrophobic interactions among the tails and the electrostatic interactions among the head groups. A significant amount of water can be present within the micellar core. In fact, ionic micelles are known to be "wetter" than nonionic micelles due to the strong repulsion among the head groups. The "hydrophobic free volume" of the SCMs can be systematically increased, thereby decreasing the packing density of the hydrophobic tails inside the SCMs. In the absence of organic reactant, these voids or hydrophobic free volume are typically filled with water, but placing water in a hydrophobic microenvironment is energetically unfavorable. As soon as such a (catalyst-containing) SCM is placed in a mixture containing organic reactant, the affinity hydrophobic free volume for the organic reactant drives the change. To increase the hydrophobic free volume of SCM, a polarity-sensitive fluorescent probe can be used to monitor the water-content inside the SCM.

Methods to Detect the Hydrophobic Free Volume Inside SCMs. Dansyl has been widely used as a polarity-sensitive The emission wavelength, emission intensity, and its accessibility by a small organic quencher (acrylamide) are three indicators for the hydrophobic free volume of a dansyl-containing SCM. In general, dansyl's emission wavelength moves to the red and its emission intensity decreases as its environment becomes more polar. When the micellar core of an SCM has a larger hydrophobic volume or contains more water, the dansyl probe can decrease in intensity and shift to red in emission. At the same time, if acrylamide is placed in the solution, the small organic quencher can enter the SCM and favorably displace the water molecules. Higher quenching is thus expected for a wetter SCM.

The hydrophobic free volume of an SCM can be increased with three different but complimentary methodologies:

Using Crosslinkable Surfactants with Sacrificial Hydrophobes. Surfactants 22 and 23 are similar to 1 in having three alkynyl groups for crosslinking through the click reaction. Instead of an ether linkage between the phenyl and the hydrocarbon tail, these two surfactants contain cleavable linkages such as ester (in 22) and siloxane (in 23). Micellization and crosslinking can be performed with these surfactants as before, except that the hydrocarbon tails can be removed by ester hydrolysis and fluoride treatment, respectively, after surface crosslinking. In some embodiments, an SCM can be prepared with 22 or 23 as the only surfactant after the hydrocarbon tails are removed. Core removal yields an empty nanocapsule. Without the hydrophobic interactions from the tails, such a structure can be unstable unless the shell is highly crosslinked. Enhanced crosslinking density can stabilize these particles. Both $^1$H NMR spectroscopy and TEM can be used to characterize such structures. The dansyl group is connected to the SCM through a sulfamide group, which is resistant to hydrolysis. As long as it is not removed during core-removal, its fluorescence can indicate an increase in polarity upon core removal.

Compounds 22 and 23 can be useful but are not necessary in the preparation of a catalyst-containing SCM. Mixing a "permanent" surfactant (e.g., 1) and a sacrificial surfactant (e.g., 22 or 23) gives SCMs with different amounts of removal hydrocarbon tails. Once the ester or siloxane linkages are cleaved, SCMs that remain hydrophobic inside can be obtained but that have different hydrophobic free volumes. Even if the catalyst is covalently attached to the SCM and leaching is not a concern, crosslinking density is important in maintaining the micellar configuration of the SCM.

Using Crosslinkable Surfactants with Noncovalent or Reversible Covalent Linkages. Surfactant 26 can be formed using the guanidinium-carboxylate salt bridge between 24 and 25. Although the hydrogen-bonded salt bridge is weak in water, it is very strong near the lipid-water and air-water interface. Micelle cores can be significantly hydrophobic microenvironments and hydrogen-bonded complexes have been shown to be stable in micelles. By using noncovalent surfactants such as 26 to form the SCM, the core removal can be much easier, e.g., washing with polar organic solvent such as methanol, and changing the hydrocarbon tail or mixing and matching multiple tails will not involve different syntheses.

Imines have been used to as the linkage to form micelle-forming, reversible surfactants. The advantage of using a reversible covalent linkage is that the hydrocarbon tails can be easily exchanged. Mixing and matching is also possible using several different amine and aldehyde precursors. This method allows one to functionalize the interior of the SCMs. Once the imine is hydrolyzed, the aldehyde groups can be used as anchors for additional functional groups. Reduction amination, for example, can easily place desired functional groups in the SCM core.

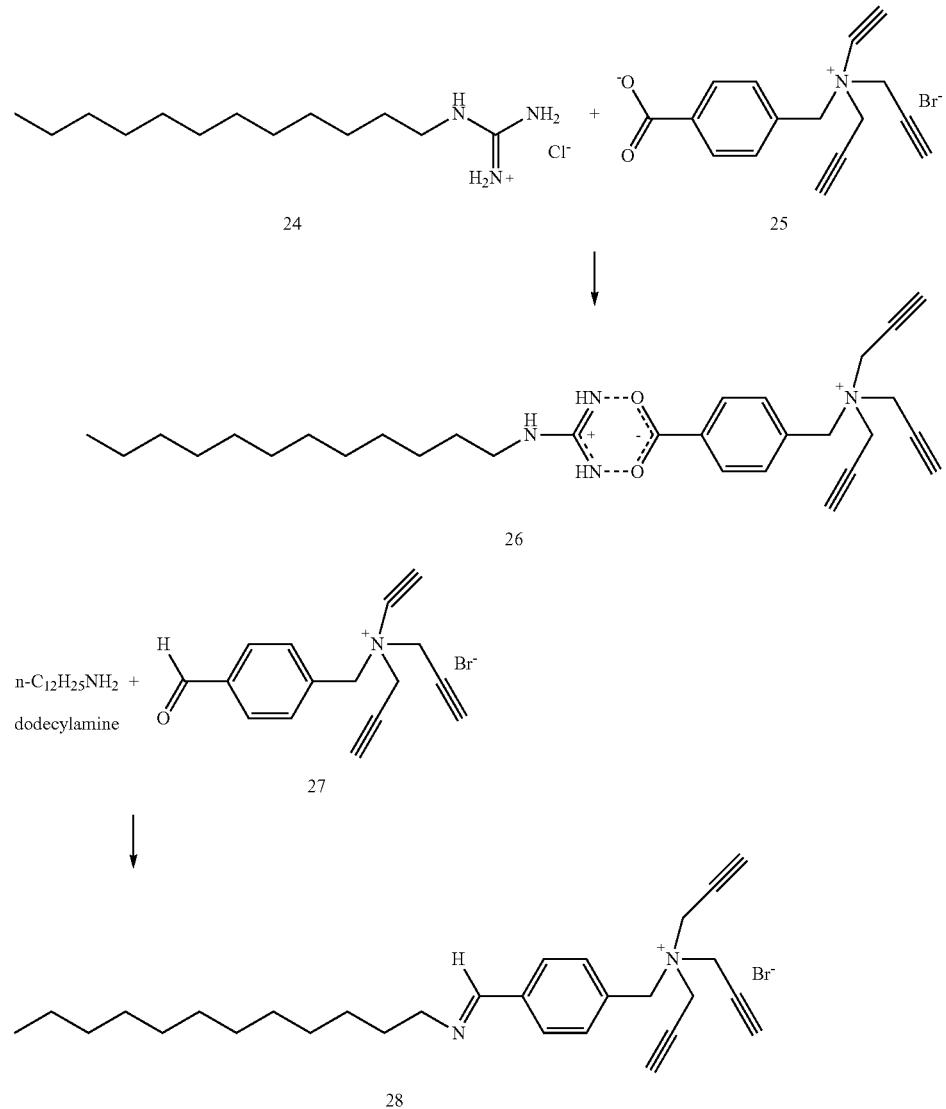

Using Noncrosslinkable Surfactants or Organic Additives in the SCM Preparation. Discussed above, the sacrificial surfactants are crosslinked in the head groups with the permanent surfactant. A noncrosslinkable surfactant such as 29, or even an organic additive such as toluene or xylene, can also be used during the SCM preparation. Surfactants 1 and 29 can form mixed micelles, which can be crosslinked through 1. Washing with methanol or dialysis can remove the uncrosslinked 29 from the SCM.

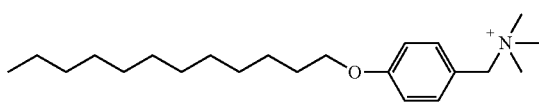

The surface crosslinking density of the SCM can be lower than those of the SCMs prepared as described above because part of the micellar surface can be occupied by the noncrosslinkable trimethylammonium. This approach is complimentary to those described above and can afford SCMs with quite different surface structure. Removal of 29 can create "pores" on the SCM surface, which can be useful to mass transfer in the catalysis.

Mixing a surfactant with an organic additive, such as toluene or xylene, is known to afford swollen micelles. "Swollen" SCMs can result if 1 and a small amount of an organic additive are used in the SCM preparation. Catalyst-containing SCMs prepared in this fashion obviate the need to hydrolyze tails or to wash the noncovalently linked tail. These SCMs may be used directly in the biphasic catalysis. The organic additive can be exchanged by the organic reactant, present in large excess. Another benefit of this approach is that, although the SCM has an increased hydrophobic free volume, the volume is occupied by hydrophobic molecules (first by the organic additive, then by the organic reactant) and instability of SCM caused by unsatisfied hydrophobic interactions is not a concern.

Example 7

Pharmaceutical Dosage Forms

The following formulations illustrate representative pharmaceutical dosage forms that may be used for the therapeutic or prophylactic administration of a composition described herein, (hereinafter referred to as 'Composition X', wherein the composition includes a drug or diagnostic agent):

| (1) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| Total | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| Total | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| Total | 600.0 |

| (iv) Injection 1 (1 mg/mL) | mg/mL |
|---|---|
| 'Composition X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

Additional Embodiments

1. An organic particle comprising surface crosslinked non-polymeric organic amphiphiles;
   wherein polar head groups of the amphiphiles are covalently crosslinked to each other at the surface of the particle through triazole groups or thioether groups, and tail groups of the amphiphiles are arranged toward the interior of the particle; and the particle is water-soluble.
2. The organic particle of embodiment 1 wherein the tail groups of the amphiphiles arranged toward the interior of the particle are non-polar hydrocarbon or fluorocarbon tail groups, polar tail groups, or a combination thereof.
3. The organic particle of embodiment 2 wherein the non-polar tail groups of the amphiphiles comprise one or more ($C_6$-$C_{22}$) alkyl groups, ($C_6$-$C_{22}$) fluoroalkyl groups, or a combination thereof, and wherein the non-polar tail groups optionally comprise one or more of ester, imine, boronate, disulfide groups or salt bridges linking a portion of the tail to a head group of the amphiphile or another portion of the tail that is linked to the head group of the amphiphile.

4. The organic particle of any one of embodiments 1-3 wherein the tail groups of the amphiphiles are non-polar and the particle has a hydrophobic core and a hydrophilic exterior; or the tail groups of the amphiphiles are polar and the particle has a hydrophilic core and a hydrophilic exterior.

5. The organic particle any one of embodiments 1-4 wherein the particle is in the form of a liposome comprising a bilayer of amphiphiles, and the bilayer comprises one or more water compartments between the bilayer of amphiphiles.

6. The organic particle of any one of embodiments 1-5 wherein the particle comprises one or more cargo molecules within the particle or at the surface of the particle.

7. The organic particle of embodiment 6 wherein the cargo molecules comprise one or more of a drug, an organic nanoparticle, an inorganic nanoparticle, a fluorophore, a diagnostic agent, and a catalysts.

8. The organic particle of any one of embodiments 1-7 wherein the surface of the particle comprises one or more surface groups comprising water-soluble polymers, fluorophores, biological ligands, nucleic acids, nucleic acid analogues, catalysts, or a combination thereof.

9. The organic particle of embodiment 8 wherein the surface groups are receptors or ligands for corresponding ligands or receptors on a biological host.

10. The organic particle of any one of embodiments 1-9 wherein the surface crosslinking can be cleaved by heat, by a change in pH, by a reducing agent, or by a combination thereof.

11. A delivery system comprising a plurality of particles of any one of embodiments 6-10, and a pharmaceutically acceptable diluent or carrier.

12. An organic particle comprising non-polymeric crosslinked amphiphiles;
wherein the amphiphiles comprise one or more nonpolar alkyl or fluoroalkyl chains and one or more polar head groups;
the nonpolar chains are located on the exterior of the particle and the polar head groups are oriented toward the interior of the particle; and
the amphiphiles are covalently crosslinked to each other near the head groups through triazole groups or thioether groups.

13. The organic particle of embodiment 12 wherein the particle comprises one or more metal salts or metal particles within the organic particle.

14. The organic particle of embodiment 12 or 13 wherein the particle comprises one or more catalytically active groups oriented toward the interior of the particle.

15. A method for preparing a surface-crosslinked organic particle comprising:
combining a plurality of non-polymeric amphiphiles and water to form a noncovalently associated self-assembled micellar structure;
wherein the non-polymeric amphiphiles have polar head groups and non-polar tail groups, and the polar head groups comprise two or more alkynyl groups or azido groups;
combining the self-assembled structure with a plurality of crosslinking agents, wherein the crosslinking agents comprise two or more azido groups or two or more alkynyl groups; and
inducing cycloaddition between the alkynes and azides, thermally or with a suitable catalyst, to covalently crosslink the amphiphiles to each other near the head groups through formation of triazole groups.

16. The method of embodiment 15 wherein the crosslinking agents comprise two or more azido groups when the polar head groups comprise alkynyl groups, or two or more alkynyl groups when the polar head groups comprise azido groups.

17. The method of embodiment 15 wherein the amphiphiles and water are in the presence of one or more cargo molecules, wherein the cargo molecules are thereby encapsulated in the hydrophobic core upon formation of the self-assembled structure.

18. The method of embodiment 17 wherein the cargo molecules comprise one or more drugs, organic nanoparticles, inorganic nanoparticles, fluorophores, diagnostic agents, catalysts, or a combination thereof.

19. The method of embodiment 15 wherein the amphiphiles and water are in the presence of one or more cargo molecules; the particles are in the form of vesicles; and the cargo molecules are encapsulated in water compartments of the vesicles.

20. The method of any one of embodiments 15-19 further comprising contacting the surface-crosslinked particle with one or more azido-containing or alkynyl-containing compounds comprising water-soluble polymers, fluorophores, biological ligands, nucleic acids or analogues thereof, or a combination thereof;
inducing cycloaddition between alkynes or azides on the surface of the particle with the azido-containing or alkynyl-containing compounds, wherein the cycloaddition is induced thermally or with a suitable catalyst;
to provide a water soluble multivalent particle that has a plurality of water-soluble polymers, fluorophores, biological ligands, nucleic acids or analogues thereof, or a combination thereof, linked to the surface of the particle through triazole groups.

21. A method for preparing a surface-crosslinked particle comprising:
combining a plurality of non-polymeric amphiphiles and water to form a noncovalently associated self-assembled structure;
wherein the non-polymeric amphiphiles have polar head groups and non-polar tail groups, and the polar head groups comprise two or more alkenyl groups;
combining the self-assembled structure with a plurality of crosslinking agents, wherein the crosslinking agents comprise two or more thiol groups; and
inducing thiol-ene addition between the alkenes of the amphiphiles and the thiol groups of the crosslinkers photochemically to covalently crosslink the amphiphiles to each other near the head groups through the formation of thioether groups.

22. The method of embodiment 21 wherein the amphiphiles and water are in the presence of one or more cargo molecules; and the cargo molecules are encapsulated in the hydrophobic core upon formation of the self-assembled structure.

23. The method of embodiment 21 wherein the amphiphiles and water are in the presence of one or more cargo molecules; the particles are in the form of vesicles; and the cargo molecules are encapsulated in water compartments formed within the vesicles.

24. The method embodiment 22 or 23 wherein the cargo molecules comprise one or more of drugs, organic nanoparticles, inorganic nanoparticles, fluorophores, diagnostic agents, and catalysts.

25. The method of any one of embodiments 21-24 further comprising contacting the surface-crosslinked particle with one or more thiol-containing compounds comprising water-soluble polymers, fluorophores, biological ligands, nucleic acids or analogues, or a combination thereof;

inducing thiol-ene addition reactions between the thiol groups of the thiol-containing compounds and alkene groups at the surface of the surface-crosslinked particle;

to provide a water soluble multivalent particle that has a plurality of functional group compounds linked to the surface of the particle through thioether groups.

26. A method for preparing an organic particle comprising:

combining a plurality of nonpolymeric amphiphiles, water, and one or more nonpolar organic solvents, wherein the amphiphiles comprise one or more ($C_6$-$C_{22}$) alkyl or fluoroalkyl chains and one or more polar head groups, to provide a noncovalently associated self-assembled structure;

wherein the amphiphiles comprise two or more alkenyl groups near the head group of the amphiphile, the alkyl or fluoroalkyl chains of the amphiphiles are oriented on the exterior of the self-assembled structure, and the polar head groups are oriented toward the interior of the self-assembled structure; and irradiating the self-assembled structures, in the presence of a plurality of crosslinking agents comprising two or more thiol groups, and a photoinitiator, to induce crosslinking at the interior of the structure;

to provide an organic particle comprising amphiphilic moieties crosslinked by thioether groups.

27. The method of any one of embodiments 15, 21, or 26, wherein the surface crosslinking is cleavable by heat, by a change in pH, by a reducing agent, or by a combination thereof.

28. A method of forming a metal nanoparticle comprising contacting a metal salt and a plurality of particles of embodiment 12 in an aqueous/organic solvent mixture, thereby extracting metal ions of the metal salt into the organic solvent, wherein the metal ions migrate to the interior of the particle, to provide a crosslinked organic particle encapsulating metal ions; and contacting the crosslinked organic particle encapsulating metal ions with a reducing agent, thereby reducing the metal ions in the interior of the crosslinked organic particle, to provide the metal nanoparticle.

29. The method of embodiment 28 wherein the metal salt comprises $AuCl_4^-$, $PtCl_6^{2-}$, $PdCl_4^{2-}$, or a combination thereof.

30. The method of embodiment 29 wherein more than one type of metal salt is contacted with the crosslinked organic particle and the metal nanoparticle formed is an alloy.

31. A therapeutic method comprising administering to a patient in need therapy an effective amount of the delivery system of embodiment 11, wherein the surface crosslinking of the particles encapsulate one or more drugs, the surface crosslinking of the particles is cleaved in vivo, and the drug of the particles is released into the body of the patient, thereby providing the drug to the patient.

32. The method of any one of embodiments 15-25 wherein one or more of the non-polar alkyl or fluoroalkyl groups at the interior of the particle are chemically degraded, shortened, or removed.

While specific embodiments have been described above with reference to the disclosed embodiments and examples, these embodiments and examples are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An organic particle comprising surface crosslinked nonpolymeric organic amphiphiles;
wherein polar head groups of the amphiphiles are covalently crosslinked to each other at the surface of the particle through triazole groups, and tail groups of the amphiphiles are arranged toward the interior of the particle; and the particle is water-soluble.

2. The organic particle of claim 1 wherein the tail groups of the amphiphiles arranged toward the interior of the particle are non-polar hydrocarbon or fluorocarbon tail groups, polar tail groups, or a combination thereof.

3. The organic particle of claim 2 wherein the non-polar tail groups of the amphiphiles comprise one or more ($C_6$-$C_{22}$) alkyl groups, ($C_6$-$C_{22}$) fluoroalkyl groups, or a combination thereof, and wherein the non-polar tail groups optionally comprise one or more of ester, imine, boronate, disulfide groups or salt bridges linking a portion of the tail to a head group of the amphiphile or another portion of the tail that is linked to the head group of the amphiphile.

4. The organic particle of claim 1 wherein the tail groups of the amphiphiles are non-polar and the particle has a hydrophobic core and a hydrophilic exterior; or the tail groups of the amphiphiles are polar and the particle has a hydrophilic core and a hydrophilic exterior.

5. The organic particle claims 1 wherein the particle is in the form of a liposome comprising a bilayer of amphiphiles, and the bilayer comprises one or more water compartments between the bilayer of amphiphiles.

6. The organic particle of claim 1 wherein the particle comprises one or more cargo molecules within the particle or at the surface of the particle.

7. The organic particle of claim 6 wherein the cargo molecules comprise one or more of a drug, an organic nanoparticle, an inorganic nanoparticle, a fluorophore, a diagnostic agent, and a catalysts.

8. The organic particle of claim 1 wherein the surface of the particle comprises one or more surface groups comprising water-soluble polymers, fluorophores, biological ligands, nucleic acids, nucleic acid analogues, catalysts, or a combination thereof.

9. The organic particle of claim 8 wherein the surface groups are receptors or ligands for corresponding ligands or receptors on a biological host.

10. The organic particle of claim 1 wherein the surface crosslinking can be cleaved by heat, by a change in pH, by a reducing agent, or by a combination thereof.

11. A delivery system comprising a plurality of particles of any one of claims 6, and a pharmaceutically acceptable diluent or carrier.

12. A therapeutic method comprising administering to a patient in need therapy an effective amount of the delivery system of claim 11, wherein the surface crosslinking of the particles encapsulate one or more drugs, the surface crosslinking of the particles is cleaved in vivo, and the drug of the particles is released into the body of the patient, thereby providing the drug to the patient.

* * * * *

UNITED STATES PATENT AND TRADEMARK OFFICE
CERTIFICATE OF CORRECTION

PATENT NO. : 8,790,621 B2
APPLICATION NO. : 13/640698
DATED : July 29, 2014
INVENTOR(S) : Yan Zhao It is certified that error appears in the above-identified patent and that said Letters Patent is hereby corrected as shown below:

In the Specification,

In column 1, line 7, delete "8Apr." and insert --8 Apr.--, therefor

In column 22-23, line 67, delete "crosslinkiner" and insert --crosslinker--, therefor In column 24, line 39, after "about", insert --10--, therefor (First occurrence)

In column 43, line 17, delete "1 1n" and insert --1 in--, therefor

In column 52, line 49 (Approx.), delete "refreactive" and insert --refractive--, therefor In column 54, line 56, delete "412." and insert --412,--, therefor (First occurrence)

Signed and Sealed this
Sixteenth Day of December, 2014

Michelle K. Lee
*Deputy Director of the United States Patent and Trademark Office*